United States Patent
Roquet et al.

(10) Patent No.: US 12,236,354 B2
(45) Date of Patent: Feb. 25, 2025

(54) SYSTEMS FOR NUCLEIC ACID-BASED DATA STORAGE

(71) Applicant: CATALOG TECHNOLOGIES, INC., Boston, MA (US)

(72) Inventors: Nathaniel Roquet, Boston, MA (US); Hyunjun Park, Boston, MA (US); Swapnil P. Bhatia, Boston, MA (US); Darren R. Link, Boston, MA (US)

(73) Assignee: CATALOG TECHNOLOGIES, INC., Boston, MA (US)

( * ) Notice: Subject to any disclaimer, the term of this patent is extended or adjusted under 35 U.S.C. 154(b) by 0 days.

(21) Appl. No.: 18/647,003

(22) Filed: Apr. 26, 2024

(65) Prior Publication Data

US 2025/0028974 A1    Jan. 23, 2025

Related U.S. Application Data

(63) Continuation of application No. 18/230,273, filed on Aug. 4, 2023, now Pat. No. 12,001,962, which is a (Continued)

(51) Int. Cl.
*G06F 16/00* (2019.01)
*C12N 9/22* (2006.01)
(Continued)

(52) U.S. Cl.
CPC ............. *G06N 3/123* (2013.01); *C12N 9/22* (2013.01); *C12N 15/1031* (2013.01);
(Continued)

(58) Field of Classification Search
CPC ...... G06F 16/2272; G06F 16/245; G06N 3/12
See application file for complete search history.

(56) References Cited

U.S. PATENT DOCUMENTS 5,821,886 A    10/1998  Son
6,187,537 B1    2/2001  Zinn et al.
(Continued)

FOREIGN PATENT DOCUMENTS

EP    1512749    3/2005
EP    2329425    7/2013
(Continued)

OTHER PUBLICATIONS

US 11,667,940 B2, 06/2023, Nguyen et al. (withdrawn)
(Continued)

*Primary Examiner* — Cheryl Lewis
(74) *Attorney, Agent, or Firm* — McDermott Will & Emery LLP

(57) ABSTRACT

Methods and systems for encoding digital information in nucleic acid (e.g., deoxyribonucleic acid) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool. But, more generally, specifying unique bytes in a bytestream by unique subsets of nucleic acid sequences. Also disclosed are methods for generating unique nucleic acid sequences without base-by-base synthesis using combinatorial genomic strategies (e.g., assembly of multiple nucleic acid sequences or enzymatic-based editing of nucleic acid sequences).

27 Claims, 21 Drawing Sheets

Related U.S. Application Data continuation of application No. 16/461,774, filed as application No. PCT/US2017/062106 on Nov. 16, 2017, now Pat. No. 11,763,169.

(60) Provisional application No. 62/466,304, filed on Mar. 2, 2017, provisional application No. 62/457,074, filed on Feb. 9, 2017, provisional application No. 62/423,058, filed on Nov. 16, 2016.

(51) Int. Cl.

| | | |
|---|---|---|
| *C12N 15/10* | (2006.01) | |
| *C40B 50/06* | (2006.01) | |
| *G06F 16/22* | (2019.01) | |
| *G06F 16/245* | (2019.01) | |
| *G06N 3/123* | (2023.01) | |
| *G11C 13/00* | (2006.01) | |
| *G16B 30/00* | (2019.01) | |
| *G16B 30/20* | (2019.01) | |
| *G16B 50/00* | (2019.01) | |
| *G16B 99/00* | (2019.01) | |

(52) U.S. Cl.
CPC .......... *C12N 15/1089* (2013.01); *C40B 50/06* (2013.01); *G06F 16/2272* (2019.01); *G06F 16/245* (2019.01); *G11C 13/0019* (2013.01); *G16B 30/00* (2019.02); *G16B 30/20* (2019.02); *G16B 50/00* (2019.02); *G16B 99/00* (2019.02); *C12N 2310/20* (2017.05)

(56) References Cited

U.S. PATENT DOCUMENTS

| | | |
|---|---|---|
| 6,221,653 B1 | 4/2001 | Caren et al. |
| 6,309,828 B1 | 10/2001 | Schleifer et al. |
| 6,384,210 B1 | 5/2002 | Blanchard |
| 6,419,883 B1 | 7/2002 | Blanchard |
| 6,446,642 B1 | 9/2002 | Caren et al. |
| 6,458,583 B1 | 10/2002 | Bruhn et al. |
| 6,537,747 B1 | 3/2003 | Mills et al. |
| 6,796,634 B2 | 9/2004 | Caren et al. |
| 7,176,297 B2 | 2/2007 | Li et al. |
| 7,306,316 B2 | 12/2007 | Doak |
| 7,491,422 B2 | 2/2009 | Zhang et al. |
| 7,600,840 B2 | 10/2009 | Kim et al. |
| 7,802,517 B2 | 9/2010 | Wessels et al. |
| 7,833,701 B2 | 11/2010 | Oshima |
| 7,909,427 B2 | 3/2011 | Kim et al. |
| 7,951,334 B2 | 5/2011 | Mirkin et al. |
| 8,071,168 B2 | 12/2011 | Cruchon-Dupeyrat |
| 8,114,207 B2 | 2/2012 | Sylvain et al. |
| 8,136,936 B2 | 3/2012 | Josten |
| 8,496,326 B2 | 7/2013 | Hook et al. |
| 8,735,327 B2 | 5/2014 | Macula |
| 8,769,689 B2 | 7/2014 | Hoglund |
| 8,806,127 B2 | 8/2014 | Brownell et al. |
| 8,835,358 B2 | 9/2014 | Fodor et al. |
| 8,856,940 B2 | 10/2014 | Kencl et al. |
| 8,937,564 B2 | 1/2015 | Aloni et al. |
| 9,061,494 B2 | 6/2015 | Rogers et al. |
| 9,062,218 B2 | 6/2015 | Oshima et al. |
| 9,187,777 B2 | 11/2015 | Jacobson et al. |
| 9,266,370 B2 | 2/2016 | Jung et al. |
| 9,317,664 B2 | 4/2016 | Ahuja et al. |
| 9,384,320 B2 | 7/2016 | Church |
| 9,403,180 B2 | 8/2016 | Ha et al. |
| 9,487,002 B2 | 11/2016 | Rogers et al. |
| 9,616,661 B2 | 4/2017 | Pierik et al. |
| 9,679,030 B2 | 6/2017 | Hatami-Hanza |
| 9,684,678 B2 | 6/2017 | Hatami-Hanza |
| 9,774,351 B2 | 9/2017 | Huetter et al. |
| 9,830,553 B2 | 11/2017 | Chen et al. |
| 9,904,734 B2 | 2/2018 | Murrah et al. |
| 9,928,869 B2 | 3/2018 | Church |
| 9,996,778 B2 | 6/2018 | Church |
| 10,020,826 B2 | 7/2018 | Gladwin et al. |
| 10,027,347 B2 | 7/2018 | Le et al. |
| 10,047,235 B2 | 8/2018 | Wilsher et al. |
| 10,050,959 B2 | 8/2018 | Soon-Shong et al. |
| 10,287,573 B2 | 5/2019 | Macula |
| 10,289,801 B2 | 5/2019 | Church |
| 10,370,246 B1 | 8/2019 | Milenkovic et al. |
| 10,387,301 B2 | 8/2019 | Goldman et al. |
| 10,417,457 B2 | 9/2019 | Peck |
| 10,423,341 B1 | 9/2019 | Kermani |
| 10,438,662 B2 | 10/2019 | Predki |
| 10,460,220 B2 | 10/2019 | Church |
| 10,566,077 B1 | 2/2020 | Milenkovic et al. |
| 10,640,822 B2 | 5/2020 | Predki et al. |
| 10,650,312 B2 | 5/2020 | Roquet et al. |
| 10,669,558 B2 | 6/2020 | Ganjam |
| 10,742,233 B2 | 8/2020 | Erlich |
| 10,754,994 B2 | 8/2020 | Peck |
| 10,774,379 B2 | 9/2020 | Chen et al. |
| 10,787,699 B2 | 9/2020 | Chen et al. |
| 10,793,897 B2 | 10/2020 | Chen et al. |
| 10,818,378 B2 | 10/2020 | Hutchison, III et al. |
| 10,838,939 B2 | 11/2020 | Walder et al. |
| 10,839,295 B2 | 11/2020 | Shen et al. |
| 10,853,244 B2 | 12/2020 | Petti et al. |
| 10,860,562 B1 | 12/2020 | Gupta et al. |
| 10,883,140 B2 | 1/2021 | Church et al. |
| 10,902,939 B2 | 1/2021 | Merriman et al. |
| 10,917,109 B1 | 2/2021 | Dimopoulou et al. |
| 10,929,039 B2 | 2/2021 | Kwon et al. |
| 10,936,953 B2 | 3/2021 | Peck et al. |
| 10,956,806 B2 | 3/2021 | Masuda et al. |
| 10,982,276 B2 | 3/2021 | Efcavitch et al. |
| 11,066,661 B2 | 7/2021 | Rausch et al. |
| 11,093,547 B2 | 8/2021 | Su et al. |
| 11,093,865 B2 | 8/2021 | Rubenstein et al. |
| 11,100,404 B2 | 8/2021 | Merriman et al. |
| 11,162,950 B2 | 11/2021 | Pfeiffer et al. |
| 11,164,190 B2 | 11/2021 | Pfeiffer et al. |
| 11,174,512 B2 | 11/2021 | Efcavitch et al. |
| 11,263,354 B2 | 3/2022 | Peck |
| 11,308,055 B2 | 4/2022 | Walder et al. |
| 11,326,161 B2 | 4/2022 | Church et al. |
| 11,339,423 B2 | 5/2022 | Bishop et al. |
| 11,365,411 B2 | 6/2022 | Chen et al. |
| 11,435,905 B1 | 9/2022 | Bahram |
| 11,485,965 B2 | 11/2022 | Strauss et al. |
| 11,495,324 B2 | 11/2022 | Yekhanin et al. |
| 11,507,135 B2 | 11/2022 | Cheung et al. |
| 11,538,554 B1 | 12/2022 | Milenkovic |
| 11,643,647 B2 | 5/2023 | Rausch et al. |
| 11,651,836 B2 | 5/2023 | Strauss et al. |
| 11,702,689 B2 | 7/2023 | Chen et al. |
| 11,704,575 B2 | 7/2023 | Strauss et al. |
| 11,720,801 B2 | 8/2023 | Nakamura et al. |
| 11,755,922 B2 | 9/2023 | Milenkovic et al. |
| 11,783,918 B2 | 10/2023 | Strauss et al. |
| 11,837,302 B1 | 12/2023 | Predki |
| 11,854,668 B2 | 12/2023 | Hayes et al. |
| 11,854,669 B1 | 12/2023 | Bachand |
| 11,873,484 B2 | 1/2024 | Chen et al. |
| 11,892,945 B2 | 2/2024 | Goldman et al. |
| 11,900,191 B2 | 2/2024 | Church |
| 11,923,004 B2 | 3/2024 | Predki et al. |
| 11,931,713 B2 | 3/2024 | Horton et al. |
| 11,943,940 B2 | 3/2024 | Hihath et al. |
| 11,961,008 B2 | 4/2024 | Bathe et al. |
| 11,970,696 B1 | 4/2024 | Haupt et al. |
| 11,928,603 B2 | 5/2024 | Ceze et al. |
| 11,989,216 B2 | 5/2024 | Ceze et al. |
| 11,990,184 B2 | 5/2024 | Mendonsa et al. |
| 12,009,062 B2 | 6/2024 | Ceze et al. |
| 12,040,055 B2 | 7/2024 | Vishwakarma et al. |
| 12,046,329 B2 | 7/2024 | Makarychev |
| 12,056,264 B2 | 8/2024 | Peck |
| 2003/0116630 A1 | 6/2003 | Carey et al. |

(56) References Cited

U.S. PATENT DOCUMENTS

| | | |
|---|---|---|
| 2004/0043390 A1* | 3/2004 | Stadler ............... G11C 13/0019 435/6.16 |
| 2004/0244623 A1 | 12/2004 | Hayashizaki |
| 2005/0019760 A1 | 1/2005 | Southern |
| 2005/0166782 A2 | 8/2005 | Hayashizaki |
| 2005/0243618 A1 | 11/2005 | Boland |
| 2006/0263534 A1 | 11/2006 | Laurent et al. |
| 2008/0252679 A1 | 10/2008 | Pierik et al. |
| 2008/0269152 A1 | 10/2008 | Verdine et al. |
| 2008/0303870 A1 | 12/2008 | Verbeek et al. |
| 2008/0309701 A1 | 12/2008 | Pierik et al. |
| 2009/0023607 A1 | 1/2009 | Rozhok et al. |
| 2009/0033690 A1 | 2/2009 | Pierik et al. |
| 2009/0062129 A1 | 3/2009 | McKernan |
| 2009/0253141 A1 | 10/2009 | Quake |
| 2010/0029490 A1 | 2/2010 | Pierik et al. |
| 2010/0056381 A1 | 3/2010 | Kurt et al. |
| 2011/0195850 A1 | 8/2011 | Rozhok et al. |
| 2011/0312779 A1 | 12/2011 | Silverbrook et al. |
| 2011/0312782 A1 | 12/2011 | Azimi et al. |
| 2011/0312847 A1 | 12/2011 | Silverbrook et al. |
| 2011/0312851 A1 | 12/2011 | Silverbrook et al. |
| 2011/0312853 A1 | 12/2011 | Azimi et al. |
| 2011/0312855 A1 | 12/2011 | Silverbrook et al. |
| 2011/0312856 A1 | 12/2011 | Silverbrook et al. |
| 2012/0164396 A1 | 6/2012 | Mirkin et al. |
| 2012/0329561 A1 | 12/2012 | Evans et al. |
| 2013/0231254 A1 | 9/2013 | Kawashima et al. |
| 2013/0233709 A1 | 9/2013 | Dunbar |
| 2013/0253839 A1 | 9/2013 | Friedlander |
| 2014/0065609 A1 | 3/2014 | Hicks et al. |
| 2014/0296087 A1 | 10/2014 | Verdine et al. |
| 2014/0371100 A1 | 12/2014 | Kawashima et al. |
| 2015/0083797 A1 | 3/2015 | Tran et al. |
| 2015/0261664 A1 | 9/2015 | Goldman et al. |
| 2015/0269313 A1 | 9/2015 | College |
| 2015/0312212 A1 | 10/2015 | Holmes et al. |
| 2015/0363550 A1 | 12/2015 | Green et al. |
| 2016/0007893 A1 | 1/2016 | Roberts |
| 2016/0051985 A1 | 2/2016 | Knight et al. |
| 2016/0168579 A1 | 6/2016 | Hutchinson et al. |
| 2016/0258939 A1 | 9/2016 | Morin |
| 2016/0304948 A1 | 10/2016 | Lee |
| 2016/0371434 A1 | 12/2016 | Strauss |
| 2017/0017436 A1 | 1/2017 | Church |
| 2017/0021611 A1 | 1/2017 | Jung et al. |
| 2017/0060924 A1 | 3/2017 | Fitzhardinge |
| 2017/0081716 A1 | 3/2017 | Peck |
| 2017/0093851 A1 | 3/2017 | Allen |
| 2017/0109229 A1 | 4/2017 | Huetter |
| 2017/0136452 A1 | 5/2017 | Niles et al. |
| 2017/0140095 A1 | 5/2017 | Kim |
| 2017/0151545 A1 | 6/2017 | Horton et al. |
| 2017/0175170 A1 | 6/2017 | Chen |
| 2017/0218228 A1 | 8/2017 | Jose et al. |
| 2017/0355982 A1 | 12/2017 | Derda et al. |
| 2017/0363953 A1 | 12/2017 | Steinhart et al. |
| 2018/0068060 A1 | 3/2018 | Ceze et al. |
| 2018/0086781 A1 | 3/2018 | Liss |
| 2018/0101487 A1 | 4/2018 | Peck |
| 2018/0121478 A1 | 5/2018 | Walder et al. |
| 2018/0137418 A1 | 5/2018 | Roquet et al. |
| 2018/0173710 A1 | 6/2018 | Maftuleac et al. |
| 2018/0173738 A1 | 6/2018 | Lopez-Ortiz et al. |
| 2018/0253563 A1 | 9/2018 | Peck et al. |
| 2019/0020651 A1 | 1/2019 | Soon-Shiong et al. |
| 2019/0040458 A1 | 2/2019 | Su et al. |
| 2019/0136307 A1 | 5/2019 | Predki |
| 2019/0138909 A1 | 5/2019 | Shen et al. |
| 2019/0142882 A1 | 5/2019 | Shepherd |
| 2019/0271032 A1 | 9/2019 | Owen |
| 2019/0325040 A1 | 10/2019 | Sagi |
| 2019/0344239 A1 | 11/2019 | Efcavitch et al. |
| 2019/0351673 A1 | 11/2019 | Roquet et al. |
| 2019/0355442 A1 | 11/2019 | Merriman |
| 2019/0383788 A1 | 12/2019 | Predki |
| 2020/0076798 A1 | 3/2020 | Lidsky |
| 2020/0185057 A1 | 6/2020 | Leake et al. |
| 2020/0193301 A1 | 6/2020 | Roquet et al. |
| 2020/0242482 A1 | 7/2020 | Merriman et al. |
| 2020/0357483 A1 | 11/2020 | Roquet et al. |
| 2021/0010065 A1 | 1/2021 | Salk |
| 2021/0050073 A1 | 2/2021 | Chen et al. |
| 2021/0074380 A1 | 3/2021 | Yekhanin |
| 2021/0108194 A1 | 4/2021 | Roquet et al. |
| 2021/0210171 A1 | 7/2021 | Stirparo et al. |
| 2021/0332426 A1 | 10/2021 | Puddu et al. |
| 2021/0348214 A1 | 11/2021 | Roquet et al. |
| 2021/0363570 A1 | 11/2021 | Mok et al. |
| 2022/0005870 A1 | 1/2022 | Hihath et al. |
| 2022/0012646 A1 | 1/2022 | Rubenstein et al. |
| 2022/0028497 A1 | 1/2022 | Keung et al. |
| 2022/0090157 A1 | 3/2022 | Mendonsa et al. |
| 2022/0179891 A1 | 6/2022 | Ceze et al. |
| 2022/0282243 A1 | 9/2022 | Chen et al. |
| 2022/0364991 A1 | 11/2022 | Wanunu et al. |
| 2022/0389483 A1 | 12/2022 | Chen et al. |
| 2023/0027270 A1 | 1/2023 | Rubenstein et al. |
| 2023/0073209 A1 | 3/2023 | Bathe et al. |
| 2023/0089824 A1 | 3/2023 | Diamanti et al. |
| 2023/0153452 A1 | 5/2023 | Peck et al. |
| 2023/0161995 A1 | 5/2023 | Masuda et al. |
| 2023/0185971 A1 | 6/2023 | Peck |
| 2023/0193383 A1 | 6/2023 | Peck |
| 2023/0207001 A1 | 6/2023 | Predki et al. |
| 2023/0215516 A1 | 7/2023 | Arsian et al. |
| 2023/0230636 A1 | 7/2023 | Gu et al. |
| 2023/0245720 A1 | 8/2023 | Strauss et al. |
| 2023/0257788 A1 | 8/2023 | Chen et al. |
| 2023/0257789 A1 | 8/2023 | Chen et al. |
| 2023/0274793 A1 | 8/2023 | Chen et al. |
| 2023/0279485 A1 | 9/2023 | Predki et al. |
| 2023/0281112 A9 | 9/2023 | Goldman et al. |
| 2023/0324822 A1 | 10/2023 | Keung et al. |
| 2023/0395198 A1 | 12/2023 | Strauss et al. |
| 2023/0419331 A1 | 12/2023 | Owen et al. |
| 2024/0011076 A1 | 1/2024 | Grass et al. |
| 2024/0035018 A1 | 2/2024 | Roselle et al. |
| 2024/0071574 A1 | 2/2024 | Bradl et al. |
| 2024/0095543 A1 | 3/2024 | Bar-Lev et al. |
| 2024/0132947 A1 | 4/2024 | Chiozzi |
| 2024/0152629 A1 | 5/2024 | Deshpande et al. |
| 2024/0168676 A1 | 5/2024 | Avraham et al. |
| 2024/0176733 A1 | 5/2024 | Avraham et al. |
| 2024/0182871 A1 | 6/2024 | Shepherd |
| 2024/0184666 A1 | 6/2024 | Oboukhov et al. |
| 2024/0185021 A1 | 6/2024 | Zamir et al. |
| 2024/0185959 A1 | 6/2024 | Oboukhov et al. |
| 2024/0193037 A1 | 6/2024 | Avraham |
| 2024/0201198 A1 | 6/2024 | Marcotte et al. |
| 2024/0229017 A1 | 7/2024 | Haupt et al. |
| 2024/0254548 A1 | 8/2024 | Strauss et al. |
| 2024/0266000 A1 | 8/2024 | Lee et al. |

FOREIGN PATENT DOCUMENTS

| | | |
|---|---|---|
| EP | 2983297 | 2/2016 |
| EP | 3067809 | 9/2016 |
| EP | 2856375 | 7/2018 |
| EP | 3346404 | 7/2018 |
| EP | 3810773 | 1/2024 |
| JP | 2009244996 | 10/2009 |
| WO | WO-03025123 | 3/2003 |
| WO | WO-2004009844 | 1/2004 |
| WO | WO-2006055943 | 5/2006 |
| WO | WO-2007135354 | 11/2007 |
| WO | WO-2012058638 | 5/2012 |
| WO | WO-2014014991 | 1/2014 |
| WO | WO-2015144858 | 10/2015 |
| WO | WO-2016015701 | 2/2016 |
| WO | WO-2016059610 | 4/2016 |
| WO | WO-2016081834 | 8/2016 |
| WO | WO-2016164779 | 10/2016 |
| WO | WO-2016182814 | 11/2016 |

(56) References Cited

FOREIGN PATENT DOCUMENTS

| | | |
|---|---|---|
| WO | WO-2017151195 | 9/2017 |
| WO | WO-2017189914 | 11/2017 |
| WO | WO-2017190297 | 11/2017 |
| WO | WO-2017192633 | 11/2017 |
| WO | WO-2018017131 | 1/2018 |
| WO | WO-2018049272 | 3/2018 |
| WO | WO-2018094108 | 5/2018 |
| WO | WO-2018094115 | 5/2018 |
| WO | WO-2018132457 | 7/2018 |
| WO | WO-2018148260 | 8/2018 |
| WO | WO-2018148458 | 8/2018 |
| WO | WO-2018213856 | 11/2018 |
| WO | WO-2019046768 | 3/2019 |
| WO | WO-2019053443 | 3/2019 |
| WO | WO-2019081145 | 5/2019 |
| WO | WO-2019178551 | 9/2019 |
| WO | WO-2019195479 | 10/2019 |
| WO | WO-2019222561 | 11/2019 |
| WO | WO-2019224544 | 11/2019 |
| WO | WO-2019246434 | 12/2019 |
| WO | WO-2020014478 | 1/2020 |
| WO | WO-2020028912 | 6/2020 |
| WO | WO-2020128517 | 6/2020 |
| WO | WO-2020132935 | 7/2020 |
| WO | WO-2020239806 | 12/2020 |
| WO | WO-2021108117 | 6/2021 |
| WO | WO-2022055885 | 3/2022 |
| WO | WO-2023026039 | 3/2023 |
| WO | WO-2024020395 | 1/2024 |
| WO | WO-2024163733 | 8/2024 |
| WO | WO-2024173908 | 8/2024 |

OTHER PUBLICATIONS

Scott E. Osborne et al., "Nucleic Acid Selection and the Challenge of Combinatorial Chemistry," 1997, American Chemical Society, pp. 349-370. (Year: 1997).*
U.S. Appl. No. 15/850,112, filed Dec. 21, 2017.
U.S. Appl. No. 16/847,064, filed Apr. 13, 2020.
U.S. Appl. No. 17/007,946, filed Aug. 31, 2020.
U.S. Appl. No. 18/230,382, filed Aug. 4, 2023.
U.S. Appl. No. 18/230,383, filed Aug. 4, 2023.
U.S. Appl. No. 18/230,385, filed Aug. 4, 2023.
U.S. Appl. No. 16/461,774, filed May 16, 2019.
U.S. Appl. No. 18/230,273, filed Aug. 4, 2023.
U.S. Appl. No. 17/012,909, filed Sep. 4, 2020.
U.S. Appl. No. 17/674,170, filed Feb. 17, 2022.
U.S. Appl. No. 18/230,296, filed Aug. 4, 2023.
U.S. Appl. No. 16/414,758, filed May 16, 2019.
U.S. Appl. No. 17/206,803, filed Mar. 19, 2021.
U.S. Appl. No. 16/532,077, filed Aug. 5, 2019.
U.S. Appl. No. 17/206,886, filed Mar. 19, 2021.
U.S. Appl. No. 16/872,129, filed May 11, 2020.
U.S. Appl. No. 18/107,851, filed Feb. 9, 2023.
U.S. Appl. No. 18/646,997, filed Apr. 26, 2024.
U.S. Appl. No. 17/069,420, filed Oct. 13, 2020.
U.S. Appl. No. 17/989,925, filed Nov. 18, 2022.
U.S. Appl. No. 17/317,547, filed May 11, 2021.
U.S. Appl. No. 17/693,705, filed Mar. 14, 2022.
U.S. Appl. No. 18/024,909, filed Mar. 6, 2023.
U.S. Appl. No. 18/027,524, filed Mar. 21, 2023.
U.S. Appl. No. 18/282,825, filed Sep. 19, 2023.
U.S. Appl. No. 17/990,255, filed Nov. 18, 2022.
U.S. Appl. No. 16/461,774, filed Sep. 18, 2024.
Al'Khafaji, A., et al., "High-throughput RNA isoform sequencing using programmable cDNA concatenation", bioRxiv, https://doi.org/10.1101/2021.10.01.462818; Oct. 1, 2021, 18 pgs.
Al'Khafaji, A., et al., "High-throughput RNA isoform sequencing using programmed cDNA concatenation", Nature Biotechnology, Jun. 8, 2023, 16 pgs.
Boneh, D., et al., "Breaking DES Using a Molecular Computer," in DIMACS Workshop on DNA Computing, 1995.
Bonnet et al., "Rewritable digital data storage in live cells via engineered control of recombination directionality," Proceeding of the National Academy of Sciences, vol. 109(23): 8884-8889 (2012).
Bornholt et al., "A DNA-Based Archival Storage System," International Conference on Architectural Support for Programming Languages and Operating Systems (ASPLOS), Apr. 2-6, 2016, Atlanta, GA, 637-649.
Braich RS, et al., "Solution of a 20-variable 3-SAT problem on a DNA computer". Science. Apr. 19, 2002;296(5567):499-502. doi: 10.1126/science.1069528. Epub Mar. 14, 2002. PMID: 11896237.
Burks et al., "The GenBank Nucleic Acid Sequence Database," Cabios Review, vol. 1(4): 225-233 (1985).
Buschmann, et al., "Levenshtein Error-Correcting Barcodes for Multiplexed DNA Sequencing", BMC Bioinformatics, vol. 14, No. 1., pp. 1-10 (2013).
Bystrykh, et al., "Generalized DNA Barcode Design Based on Hamming Codes", Plos One, vol. 7, No. 5, pp. 1-8, (May 2012).
Casini, A. "Advanced DNA assembly strategies and standards for synthetic biology," Thesis, Department of Life Sciences, Imperial College London: 1-178 (2014).
Clarke, et al., "Continuous base identification for single-molecule nanopore DNA sequencing" Nature Nanotechnology, vol. 4, pp. 265-270, (2009).
Click chemistry—Wikipedia, Wikipedia, Apr. 11, 2017, pp. 1-11; XP093142494, Retrieved from the Internet: URL:https://web.archive.org/web/20171104103152/https://en.wikipedia.org/wiki/Click_chemistry#Potential_applications [retrieved on Mar. 18, 2024].
Craig, et al., "Ordering of Cosmid Clones covering the Herpes Simplex Virus Type 1 (HSV-1) genome: a test case for fingerprinting by hybridisation", Nucleic Acids Research, vol. 18, pp. 2653-2660 (1990).
Cui, M., et al., "Nonlinear manipulation and analysis of large DNA datasets", Nucleic Acids Research, vol. 50, No. 15 , Aug. 10, 2022, pp. 8974-8985.
De Silva, et al., "New Trends of Digital Data Storage in DNA", BioMed Research International, vol. 2016, Article ID 8072463, 14 pages (Sep. 5, 2016) ps. 14.
Deorowicz et al., "Data compression for sequencing data," Algorithms for Molecular Biology, vol. 8(25): 1-13 (2013).
Design & Analysis of Algorithms, Lecture #25: Burrows-Wheeler Transform, pp. 1-8 (Year: 2018).
El-Sagheer, A., et al., "Click Nucleic Acid Ligation: Applications in Biology and Nanotechnology", Accounts of Chemical Research, vol. 45, No. 8, pp. 1258-1267. Dec. 12, 2011.
Engler et al., "A One Pot, One Step, Precision Cloning Method with High Throughput Capability," PLoS ONE, vol. 3(11): E3647 (2008) printed as pp. 1-7.
Engler et al., "Chapter 12: Combinatorial DNA Assembly Using Golden Gate Cloning," Karen M. Polizzi and Cleo Kontoravadi (eds.), Synthetic Biology, Methods in Molecular Biology, vol. 1073 , Springer Science+Business Media, New York: 141-156 (2013).
Erciyes, K., Distributed and Sequential Algorithms for Bioinformatics, Computational Biology, 2015, 23, Springer, Ed. A. Dress, 1-133. (Year: 2015).
Extended European Search Report for EP Application No. 17872172.6 dated Oct. 27, 2020 (10 pgs).
Supplementary European Search Report for EP Application No. 17872574.3 dated Sep. 14, 2020 (2 pgs).
Fogg et al., "New Applications for Phage Integrases," Journal of Molecular Biology, vol. 426(15): 2703-2716 (2014).
Gardner, et al., "Acyclic and dideoxy terminator preferences denote divergent sugar recognition by archaeon and Taq DNA polymerases", Nucleic Acids Res. Jan. 15, 2002;30(2):605-13.
Goldman et al., "Towards practical, high-capacity, low-maintenance information storage in synthesized DNA," Nature, vol. 494: 77-80 (2013).
Kivioja et al., "Counting absolute Nos. of molecules using unique molecular identifiers," Nature Methods, vol. 9(1): 72-74 (2011), including pp. 1-2 of Online Methods, and pp. 1-14 of Supplementary Information.

(56) References Cited

OTHER PUBLICATIONS

Lahr, et al., "Reducing the impact of PCR-mediated recombination in molecular evolution and environmental studies using a new-generation high-fidelity DNA polymerase", Biotechniques. Oct. 2009;47(4):857-66.
Langmead, Ben, Introduction to the Burrows-Wheeler Transform and FM Index, Department of Computer Science, JHU, pp. 1-12; Nov. 24, 2013.
Lee, et al, "Enzymatic DNA synthesis for digital information storage", bioRxiv, XP055603868, DOI: 10.1101/348987 Retrieved from the Internet: URL:https://www.biorxiv.org/content/biorxiv/early/2018/06/16/348987.full.pdf [retrieved on Nov. 20, 2019] abstract, pp. 31 pages (2018).
Lee et al, "DNA detection using commercial mobile phones", Biosensors and Bioelectronics, 2011, 26, 4349-4354 (Year: 2011).
Lee, et al., "Terminator-free template-independent enzymatic DNA synthesis for digital information storage", Nat Commun. Jun. 3, 2019;10(1): 12 pages.
Leier et al., "Cryptography with DNA binary strands," Biosystems, vol. 57: 13-22 (2000).
Li, H., et al., "Fast and accurate short read alignment with Burrows-Wheeler transform", Bioinformatics, vol. 25, Issue 14, pp. 1754-1760, Jul. 2009, https://doi.org/10.1093/bioinformatics/btp324 (Year: 2009).
Ligation (molecular biology) Wikipedia, Wikipedia, Oct. 10. 2016, pp. 1-5; XP093142492, Retrieved from the Internet: URL:https://web.archive.org/web/20161010083548/https://en.wikipedia.org/wiki/Ligation_(molecular_biology) [retrieved on Mar. 18, 2024].
Lipton RJ., "DNA solution of hard computational problems", Science. Apr. 28, 1995;268(5210):542-5. doi: 10.1126/science.7725098. PMID: 7725098.
Navarro, et al., "Compressed Full-Text Indexes", ACM Computing Surveys, ACM, New York, NY, vol. 39, No. Apr. 1, 12, 2007.
Nour-Eldin, H., et al., "Advancing uracil-excision based cloning towards an ideal technique for cloning PCR fragments", Nucleic Acids Research, 2006, vol. 34, No. 18, Sep. 26, 2006, 8 pgs.
Organick, et al., "Random access in large-scale DNA data storage", Nature Biotechnology, 36(3): 242-248, (2018).
Patrick, et al., DNA Assembly in 3D Printed Fluidics, PLOS One, 10(12): e014636 18 pages (2015).
PCT/US2017/062098 International Search Report and Written Opinion dated, Mar. 14, 2018 (20 pgs).
PCT/US2017/062106 International Search Report and Written Opinion dated, Feb. 22, 2018 (8 pgs).
PCT/US2019/022596 International Search Report and Written Opinion dated, Jun. 28, 2019 (14 pgs).
PCT/US2019/032756 International Search Report and Written Opinion dated, Sep. 4, 2019 (23 pgs).
PCT/US2019/045160 International Search Report and Written Opinion dated, Jan. 30, 2020 (19 pgs).
PCT/US2020/032384 International Search Report and Written Opinion dated, Jul. 30, 2020 (20 pgs).
PCT/US2020/055351 International Search Report and Written Opinion dated, Mar. 31, 2021 (20 pgs).
PCT/US2021/031865 International Search Report and Written Opinion dated, Aug. 13, 2021 (21 pgs).
PCT/US2021/049289 International Search Report and Written Opinion dated, Nov. 18, 2021 (13 pgs).
PCT/US2022/020949 International Search Report and Written Opinion dated, Jun. 23, 2022 (10 pgs).
PCT/US2022/050435 International Search Report and Written Opinion dated, May 11, 2023 (18 pgs).
PCT/US2023/15495 International Search Report and Written Opinion dated, May 23, 2023 (13 pgs).
Quetier et al., "The CRISPR-Cas9 technology: Closer to the ultimate toolkit for targeted genome editing," Plant Science, vol. 242: 65-76 (2015).
Roquet, et al, "DNA-based data storage via combinatorial assembly", bioRxiv 2021.04.20.440194; doi: https://doi.org/10.1101/2021.04.20.440194, Apr. 20, 2021, (15 pgs).
Roquet et al., "Synthetic recombinase-based state machines in living cells," Science, vol. 353(6297): 363, aad8559-1-aad8559-13 (2016).
Sands, et al, "Overview of Post Cohen-Boyer Methods for Single Segment Cloning and for Multisegment DNA Assembly," Current Protocols in Molecular Biology, vol. 113: 3.26.1-3.26-20 (2016).
Schlecht, U., et al., "ConcatSeq: A method for increasing throughput of single molecule sequencing by concatenating short DNA fragments", Scientific Reports, Jul. 12, 2017, 10 pgs.
Sorek et al., "CRISPR-Mediated Adaptive Immune Systems in Bacteria and Archaea," Annual Review of Biochemistry, vol. 82: 237-266 (2013).
Staden, R., "Nucleic Acids Research—Sequence Data Handling by Computer," vol. 4(11): 4037-4052 (1977).
Staden, R., "Computer Methods to Locate Signals in Nucleic Acid Sequences", Nucleic Acids Research, vol. 12, No., 1, Part 2, Jan. 11, 1984 (505-519).
Staden, R., "An Interactive Graphics Program for Comparing and Aligning Nucleic Acid and Amino Acid Sequences," Nucleic Acids Research, vol. 10, Issue 9, May 11, 1982 (2951-2061).
Sun et al., "Recent advances in targeted genome engineering in mammalian systems," Biotechnology Journal, vol. 7: 1074-1087 (2012).
Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).
Verardo, D., et al., "Multiplex enzymatic synthesis of DNA with single-base resolution", Science Advances, Jul. 7, 2023 (13 pgs).
Yang et al., "Permanent genetic memory with >1-byte capacity," Nature Methods, vol. 11(12): 1261-1266 (2014) including pp. 1-3 of Online Methods, and pp. 1-30 of Supplementary Figures and Text.
Yazdi et al., "A Rewritable, Random-Access DNA-Based Storage System," Scientific Reports, vol. 5(14138): 1-10 (2015), including pp. 1-19 of Supplementary Information.
Yazdi et al., "DNA-based storage: Trends and Methods," IEEE Transactions on Molecular, Biological, and Multi-Scale Communications, vol. 1(3): 230-248 (Sep. 1, 2015).
Yazdi, et al., "Portable and Error-Free DNA-Based Data Storage", bioRxiv preprint doi: https://doi.org/10.1101/079442 (2016).
Yim et al., "The essential component in DNA-based information storage system: robust error-tolerating module," Frontiers in Bioengineering and Biotechnology, vol. 2, Article 49: 1-5 (2014).
Yolov, et al., "Constructing DNA by polymerase recombination", Nucleic Acids Res. Jul. 11, 1990;18(13):3983-6.
Zhu et al., "High-throughput DNA sequence data compression," Briefings in Bioinformatics, 16(1): 1-15 (2015).

\* cited by examiner

| Original Words | | Expansion Codewords | | | | | | | |
|---|---|---|---|---|---|---|---|---|---|
| | | Cost of Recoding Word as Codeword | | | | | | | |
| Word | Count | 000 | 001 | 010 | 011 | 100 | 101 | 110 | 111 |
| 00 | 0 | 0 | 0 | 0 | 0 | 0 | 0 | 0 | 0 |
| 01 | 3 | 0 | 3 | 3 | 6 | 3 | 6 | 6 | 9 |
| 10 | 4 | 0 | 4 | 4 | 8 | 4 | 8 | 8 | 12 |
| 11 | 1 | 0 | 1 | 1 | 2 | 1 | 2 | 2 | 3 |
| Cost | 9 | New cost | | | | 4 | | | |

| Original Words | Uniform Weight Codewords |
|---|---|
| 00 | 0011 |
| 01 | 0101 |
| 10 | 0110 |
| 11 | 1001 |

SYSTEMS FOR NUCLEIC ACID-BASED DATA STORAGE

CROSS-REFERENCE

This application is a continuation of U.S. patent application Ser. No. 18/230,273 filed Aug. 4, 2023 (U.S. Pat. No. 12,001,962) which is a continuation of U.S. patent application Ser. No. 16/461,774 filed May 16, 2019 (U.S. Pat. No. 11,763,169), which is a United States National Stage filing under 35 U.S.C. § 371 of International Application No. PCT/US2017/062106, filed Nov. 16, 2017, and claims the benefit of U.S. Provisional Patent Application Ser. No. 62/423,058, filed Nov. 16, 2016, U.S. Provisional Patent Application Ser. No. 62/457,074, filed Feb. 9, 2017, and U.S. Provisional Patent Application Ser. No. 62/466,304 filed Mar. 2, 2017. The disclosures of the foregoing applications are hereby incorporated by reference in their entirety.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

To access digital data stored in nucleic acid molecules, the nucleic acid molecules may be sequenced. As such, nucleic acid digital data storage may be an ideal method for storing data that is not frequently accessed but has a high volume of information to be stored or archived for long periods of time.

Current methods rely on encoding the digital information (e.g., binary code) into base-by-base nucleic acids sequences, such that the base to base relationship in the sequence directly translates into the digital information (e.g., binary code). Sequencing of digital data stored in base-by-base sequences that can be read into bit-streams or bytes of digitally encoded information can be error prone and costly to encode since the cost of de novo base-by-base nucleic acid synthesis can be expensive. Opportunities for new methods of performing nucleic acid digital data storage may provide approaches for encoding and retrieving data that are less costly and easier to commercially implement.

SUMMARY

Methods and systems for encoding digital information in nucleic acid (e.g., deoxyribonucleic acid, DNA) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool. But, more generally, specifying unique bytes in a byte stream by unique subsets of nucleic acid sequences. Also disclosed are methods for generating unique nucleic acid sequences without base-to-base synthesis using combinatorial genomic strategies (e.g., assembly of multiple nucleic acid sequences or enzymatic-based editing of nucleic acid sequences).

In an aspect, the present disclosure provides a method for coding digital information into nucleic acid sequence(s), comprising: (a) coding the digital information into a sequence of symbols and converting the sequence of symbols into codewords using one or more codebooks; (b) parsing the codewords into a coded sequence of symbols; (c) mapping the coded sequence of symbols to a plurality of identifiers, wherein an individual identifier of the plurality of identifiers comprises one or more nucleic acid sequences; (d) enumerating an identifier library wherein each symbol of the coded sequence of symbols is encoded by one or more identifier(s); and (e) appending a description of the one or more codebooks and the plurality of identifiers to the identifier library.

In some embodiments, the coded sequence of symbols comprises symbols taken from a fixed alphabet of symbols. In some embodiments, the method further comprises converting the coded sequence into a second sequence of symbols. In some embodiments, the second sequence of symbols comprises a formal data structure. In some embodiments, the formal data structure comprises one or more members selected from the group consisting of a tree structure, a trie structure, a table structure, a key-value dictionary structure, and a set. In some embodiments, the formal data structure is queryable by range queries, rank queries, count queries, membership queries, nearest neighbor queries, match queries, selection queries, or any combination thereof.

In some embodiments, the method further comprising parsing the second sequence of symbols into a sequence of words. In some embodiments, the method further comprising converting the sequence of words into the sequence of codewords using the one or more codebooks. In some embodiments, the method further comprises converting the sequence of codewords into a third sequence of symbols. In some embodiments, converting the sequence of words into the sequence of codewords minimizes a number of one or more types of symbols in the third sequence of symbols.

In some embodiments, the coded sequence of symbols comprises one or more blocks of symbols. In some embodiments, converting the sequence of words into the sequence of codewords generates a fixed number of one or more types of symbols in each block of symbols of the one or more blocks of symbols in the third sequence of symbols. In some embodiments, a codebook appends one or more error protection symbols to individual codewords of the sequence of codewords. In some embodiments, the one or more error protection symbols are computed from one or more words of the sequence of words.

In some embodiments, the plurality of identifiers are selected from a combinatorial space of identifiers. In some embodiments, an individual identifier of the plurality of identifiers comprises one or more components. In some embodiments, an individual component of the one or more components comprises a nucleic acid sequence. In some embodiments, the nucleic acid sequence is a distinct sequence.

In some embodiments, each symbol in the string of symbols is one of two possible symbol values. In some embodiments, one symbol value at each position of the string of symbols may be represented by the absence of a distinct identifier in the identifier library. In some embodiments, the two possible symbol values are a bit-value of 0 and 1, wherein the individual symbol with the bit-value of 0 in the string of symbols may be represented by an absence of a distinct identifier in the identifier library, wherein the individual symbol with the bit-value of 1 in the string of symbols may be represented by a presence of the distinct identifier in the identifier library, and vice versa. In some embodiments, a presence of the individual identifier in the identifier library corresponds to a first symbol value in a binary string and an absence of the individual identifier from the identifier library corresponds to a second symbol value in a binary string. In some embodiments, the first symbol value is '1' and the second symbol value is '0'. In some embodiments, the first symbol value is '0' and the second symbol value is '1'. In some embodiments, the identifier library comprises supplemental nucleic acid sequences. In some embodiments, the supplemental nucleic acid sequences comprise metadata about the first sequence of symbols or an encoding of the first sequence of symbols. In some embodiments, the supplemental nucleic acid sequences do not correspond to digital information and wherein the supplemental nucleic acid sequences conceal the digital information encoded in the identifier library.

In some embodiments, the one or more identifier(s) are generated by combinatorial assembly of one or more components. In some embodiments, the method further comprises constructing a universal identifier library. In some embodiments, the identifier library is constructed from the universal identifier library by degrading or excluding the individual identifiers that are not present in the identifier library. In some embodiments, constructing the universal identifier library comprises using one or more reactions. In some embodiments, the one or more reactions that correspond to the individual identifier not present in the identifier library are removed, deleted, degraded, or inhibited. In some embodiments, the one or more reactions comprise components, templates and/or reagents and wherein the components, the templates, and/or the reagents are loaded on films, threads, fibers, or other substrates. In some embodiments, the components, the templates, and/or the reagents are disposed adjacent to one another by stamping, intertwining, braiding, pinching, or weaving the films, the threads, the fibers, or the other substrates.

In another aspect, the present disclosure provides a system for coding digital information into nucleic acid sequence(s), comprising: an assembly unit configured to generate an identifier library encoding a sequence of symbols, wherein the identifier library comprises at least a subset of a plurality of identifiers; and one or more computer processors operatively coupled to the assembly unit, wherein the one or more computer processors are individually or collectively programmed to (i) code the digital information into a sequence of symbols and convert the sequence of symbols into codewords using one or more codebooks, (ii) parse the codewords into a coded sequence of symbols, (iii) map the coded sequence of symbols to the plurality of identifiers, wherein an individual identifier of the plurality of identifiers comprises one or more nucleic acid sequences, (iv) direct the assembly unit to generate an identifier library, wherein each symbol of the coded sequence of symbols is encoded by one or more identifier(s), and (v) direct the assembly unit to append a description of the one or more codebooks and the plurality of identifiers to the identifier library.

In some embodiments, the one or more identifier(s) are assembled in one or more assembly reactions. In some embodiments, one or more products of the one or more assembly reactions are combined to generate the identifier library.

In some embodiments, the assembly unit comprises one or more vessels. In some embodiments, the one or more vessels are partitions. In some embodiments, the assembly unit comprises reagents, one or more layers of components, one or more templates, or any combination thereof. In some embodiments, the assembly unit is configured to receive reagents, one or more layer of components, one or more templates, or any combination thereof. In some embodiments, the assembly unit is configured to output the identifier library.

In some embodiments, the assembly unit comprises a reaction module. In some embodiments, the reaction module is configured to collect reagents, one or more layers, one or more templates, or any combination thereof. In some embodiments, the reagents comprise enzymes, one or more nucleic acid sequences, buffers, co-factors, or any combination thereof. In some embodiments, the reagents are combined into a master mix prior to entering the reaction module. In some embodiments, the reaction module is configured to incubate or agitate an assembly reaction and wherein the assembly reaction generates the one or more identifier(s). In some embodiments, the reaction module comprises a detector unit and wherein the detector unit monitors assembly of the one or more identifier(s).

In some embodiments, the system further comprises a storage unit and wherein the assembly unit transfers the generated identifier library to the storage unit. In some embodiments, the storage unit comprises one or more pools, vessels, or partitions. In some embodiments, the storage unit combines one or more identifier libraries into the one or more pools, the one or more vessels, or the one or more partitions.

In some embodiments, the system further comprises a selection unit configured to select the one or more identifier(s). In some embodiments, the selection unit comprises a size selection module, an affinity capture module, a nuclease cleavage module, or any combination thereof.

In some embodiments, the system further comprises a nucleic acid synthesis unit configured to synthesize the one or more nucleic acid sequences. In some embodiments, the one or more nucleic acid sequences are constructed with base-by-base synthesis.

In some embodiments, the assembly unit generates a plurality of reactions for assembling the one or more identifier(s). In some embodiments, the assembly unit selectively removes individual reactions from the plurality of reactions that do not generate the at least the subset of the plurality of identifiers in the identifier library.

In some embodiments, the assembly unit uses one or more of electrowetting, misting, printing, laser ablation, weaving or braiding or intertwining of nucleic acid sequence coated materials, slip technology, stamping, laser printing, or droplet microfluidics to generate the identifier library.

In some embodiments, the one or more computer processors are individually or collectively programmed to use heuristic techniques to minimize a number of reactions to generate the identifier library or to minimize the time it takes to set up a number of reactions to generate the identifier library. In some embodiments, the heuristic techniques comprise on-set covering heuristics or heuristics that minimize the traveling path of an apparatus.

In another aspect, the present disclosure provides an integrated nucleic acid-based storage system comprising: a data encoding unit configured to write digital information in one or more nucleic acid sequences, wherein the data encoding unit writes the digital information in the one or more nucleic acid sequences in the absence of base-by-base nucleic acid synthesis; a storage unit configured to store the one or more nucleic acid sequences encoding the digital information; a reading unit configured to access and read the digital information encoded in the one or more nucleic acid sequences; and one or more computer processors operatively coupled to the data encoding unit, the storage unit, and the reading unit, wherein the one or more computer processors are individually or collectively programmed to (i) direct the data encoding unit to encode the digital information into the one or more nucleic acid sequences, (ii) direct the storage unit to store the digital information encoded into the one or more nucleic acid sequences, and (iii) direct the reading unit to access and decode the digital information stored in the one or more nucleic acid sequences.

In some embodiments, the one or more computer processors parses the digital information into a plurality of symbols. In some embodiments, the plurality of symbols is mapped to a plurality of identifiers. In some embodiments, an individual symbol of the plurality of symbols corresponds to one or more identifiers of the plurality of identifiers. In some embodiments, the plurality of identifiers comprise a plurality of components. In some embodiments, an individual component of the plurality of components comprises a distinct nucleic acid sequence.

In some embodiments, the data encoding unit generates one or more identifier libraries comprising one or more sets of identifiers corresponding to the digital information. In some embodiments, reading the digital information comprises identifying the one or more sets of identifiers in the one or more identifier libraries.

In some embodiments, the system is automated. In some embodiments, the system is networked. In some embodiments, the system is configured to operate in a zero or low-gravity environment. In some embodiments, the system is configured to operate at pressures below atmospheric pressure, or under vacuum, or above atmospheric pressure. In some embodiments, the system comprises a power source or power generation method. In some embodiments, the system comprises a radiation shield.

In some embodiments, the identifier library generated is a universal library. In some embodiments, the system further comprises a plurality of modules. In some embodiments, a first module creates an identifier library. In some embodiments, a second module implements deletion of the individual identifiers or of an identifier reaction. In some embodiments, a third module separates the individual identifiers present in the identifier library from the individual identifiers not present in the identifier library. In some embodiments, a fourth module groups or pools the identifier library into one or more partitions. In some embodiments, the one or more partitions are stored separate from the system. In some embodiments, one or more reaction compartments, vessels, partitions, or substrates are mounted or stored on a disc, a plate, a film, a fiber, a tape, or a thread separate from the system before, after, or both before and after generation of the identifier library or a universal library.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 2A illustrates combining a rank object (or address object) with a byte-value object (or data object) to create an identifier; FIG. 2B illustrates an embodiment of the data at address method wherein the rank objects and byte-value objects are themselves combinatorial concatenations of other objects;

FIG. 3A illustrates encoding digital information using a rank object as an identifier; FIG. 3B illustrates an embodiment of the encoding method wherein the address objects are themselves combinatorial concatenations of other objects;

DETAILED DESCRIPTION

Figure 1:
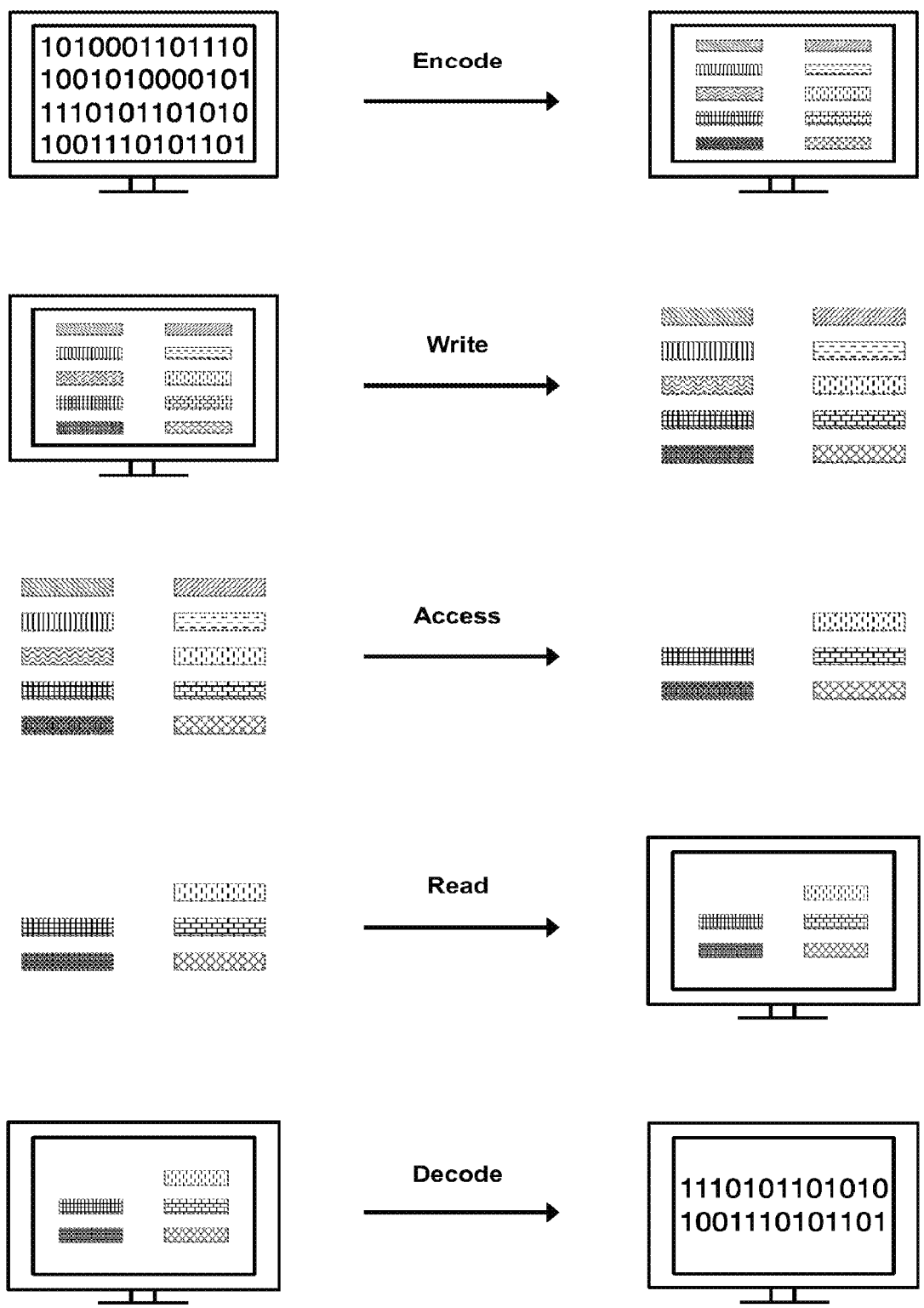
FIG. 1 schematically illustrates an overview of a process for encoding, writing, accessing, reading, and decoding digital information stored in nucleic acid sequences.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "digital message," as used herein, generally refers to a sequence of symbols provided for encoding into nucleic acid molecules. The digital message may be the original text that is written into nucleic acid molecules.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence. A component may be a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some embodiments, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol string representing digital information. In some embodiments, the absence of a given identifier in the identifier library may indicate a symbol value at a particular position. One or more identifier libraries may be combined in a pool, group, or set of identifiers. Each identifier library may include a unique barcode that identifies the identifier library.

The term "universal library," as used herein generally refers to a collection of identifiers corresponding to the set of all possible distinct identifiers that may be generated from a starting set of objects, such as components, and a permissible set of rules for how to modify those objects to form identifiers.

The term "word," as used herein, generally refers to a block of a string of symbols. The length of the block may be fixed or may not be fixed. A string of symbols may be divided into one or more words comprising a length of L symbols. In an example, a string of symbols sixteen (16) symbols in length may be divided into four (4) words, each four (4) symbols in length.

The term "codeword," as used herein, generally refers to symbol string that codes a word. The length of the string may be fixed or may not be fixed. A source bitstream may be parsed into words that are subsequently converted to codewords using a codebook. The codebook may correlate words to codewords. Codewords may be selected to reduce writing time, minimize identifier construction, or to detect writing errors.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that is specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid molecule is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. An oligonucleotide, as used herein, generally refers to a single-stranded nucleic acid sequence, and is typically composed of a specific sequence of four nucleotide bases: adenine (A); cytosine (C); guanine (G); and thymine (T) (uracil (U) for thymine (T) when the polynucleotide is RNA). The term "nucleic acid sequence" may refer to the alphabetical representation of a polynucleotide molecule; alternatively, the term may be applied to the physical polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at 3'-end of a primer attached to the DNA sample and copies the opposite strand.

The term "polymerase", or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof.

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Previous methods for encoding digital information into nucleic acids have relied on base-by-base synthesis of the nucleic acids, which can be costly and time consuming. Alternative methods may improve the efficiency, improve the commercial viability of digital information storage by reducing the reliance on base-by-base nucleic acid synthesis for encoding digital information, and eliminate the de novo synthesis of distinct nucleic acid sequences for every new information storage request.

New methods can encode digital information (e.g., binary code) in a plurality of identifiers, or nucleic acid sequences, comprising combinatorial arrangements of components instead of relying on base-by-base or de-novo nucleic acid synthesis (e.g., phosphoramidite synthesis). As such, new strategies may produce a first set of distinct nucleic acid sequences (or components) for the first request of information storage, and can there-after re-use the same nucleic acid sequences (or components) for subsequent information storage requests. These approaches can significantly reduce the cost of DNA-based information storage by reducing the role of de-novo synthesis of nucleic acid sequences in the information-to-DNA encoding and writing process. Moreover, unlike implementations of base-by-base synthesis, such as phosphoramidite chemistry- or template-free polymerase-based nucleic acid elongation, which require cyclical delivery of each base to each elongating nucleic acid, new methods of information-to-DNA writing using identifier construction from components are highly parallelizable processes that may not use cyclical nucleic acid elongation. Thus, new methods may increase the speed of writing digital information to DNA compared to older methods.

Methods for Encoding and Writing Information to Nucleic Acid Sequence(s)

In an aspect, the present disclosure provides methods for coding a sequence of symbols for writing into nucleic acid sequence(s). A method for coding a sequence of symbols for writing into nucleic acid sequence(s) may comprise (a) converting the sequence of symbols into codewords using one or more codebooks, (b) parsing the codewords into a coded sequence of symbols, (c) mapping the coded sequence of symbols to a plurality of identifiers, (d) generating an identifier library, and (e) appending a description of the one or more codebooks and the plurality of identifiers to the identifier library. Each symbol of the coded sequence of symbols may be encoded by one or more identifier(s).

FIG. 1 illustrates an overview process for encoding information into nucleic acid sequences, writing information to the nucleic acid sequences, reading information written to nucleic acid sequences, and decoding the read information. Digital information, or data, may be translated into one or more strings of symbols. In an example, the symbols are bits and each bit has a value of either '0' or '1'. Each symbol may be mapped, or encoded, to an object (e.g., identifier) representing that symbol. Each symbol may be represented by a distinct identifier. The distinct identifier may be a nucleic acid molecule made up of components. The components may be nucleic acid sequences. The digital information may be written into nucleic acid sequences by generating an identifier library corresponding to the information. The identifier library may be physically generated by physically constructing the identifiers that correspond to each symbol of the digital information. All or any portion of the digital information may be accessed at a time. In an example, a subset of identifiers is accessed from an identifier library. The subset of identifiers may be read by sequencing and identifying the identifiers. The identified identifiers may be associated with their corresponding symbol to decode the digital data. FIG. 1 illustrates an overview process for encoding information into nucleic acid sequences, writing information to the nucleic acid sequences, reading information written to nucleic acid sequences, and decoding the read information without using base-by-base synthesis. Digital information, or data, may be translated into one or more strings of symbols. In an example, the symbols are bits and each bit has a value of either '0' or '1'. Each symbol may be mapped, or encoded, to a physical object (e.g., identifier) representing that symbol. Each symbol may be represented by a distinct identifier. The distinct identifier may be a nucleic acid molecule made up of components. The components may be nucleic acid sequences. The digital information may be written into nucleic acid sequences by generating an identifier library corresponding to the information. The identifier library may be generated by assembling the identifiers that correspond to each symbol of the digital information. All or a portion of the digital information may be accessed at a time. In an example, a subset of identifiers is removed from an identifier library. The subset of identifiers may be read by identifying the identifiers. The identified identifiers may be associated with their corresponding symbol to decode the digital data.

A method for encoding and reading information using the approach of FIG. 1 can, for example, include receiving a bit stream. This may include mapping each one-bit (bit with bit-value of '1') in the bit stream to a distinct nucleic acid identifier using an identifier rank. Constructing a nucleic acid sample pool, or identifier library, comprising copies of the identifiers that correspond to bit values of 1 (and excluding identifiers for bit values of 0). Reading the sample can comprise using molecular biology methods (e.g., sequencing, hybridization, PCR, etc), determining which identifiers are represented in the identifier library, and assigning bit-values of '1' to the bits corresponding to those identifiers and bit-values of '0' elsewhere (again referring to the identifier rank to identify the bits in the original bit-stream that each identifier corresponds to), thus decoding the information into the original bit stream that was encoded.

Encoding a string of N distinct bits, can use an equivalent number of unique nucleic acid sequences as possible identifiers. This approach to information encoding may use de-novo synthesis of identifiers for each new item of information (string of N bits) to store. In other instances, the cost of newly synthesizing identifiers (equivalent in number to or less than N) for each new item of information to store can be reduced by the one-time de-novo synthesis and subsequent maintenance of all possible identifiers, such that encoding new items of information may involve mechanically selecting and mixing together pre-synthesized (or pre-fabricated) identifiers to form an identifier library. In other instances, both the cost of (1) de-novo synthesis of up to N identifiers for each new item of information to store or (2) maintaining and selecting from N possible identifiers for each new item of information to store, or any combination thereof, may be reduced by synthesizing and maintaining a number (less than N, and in some cases much less than N) of nucleic acid sequences and then modifying these sequences through enzymatic reactions to generate up to N identifiers for each new item of information to store.

The identifiers may be rationally designed and selected for ease of read, write, access, copy, and deletion operations. The identifiers may be designed and selected to minimize write errors, mutations, degradation, and read errors.

Figure 2A:
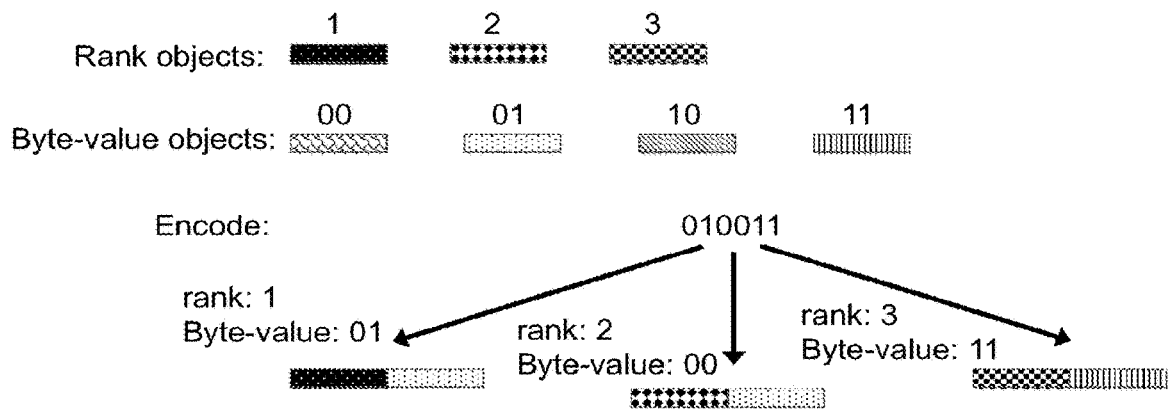
FIGS. 2A and 2B schematically illustrate a method of encoding digital data, referred to as "data at address", using objects or identifiers (e.g., nucleic acid molecules)
Figure 2B:
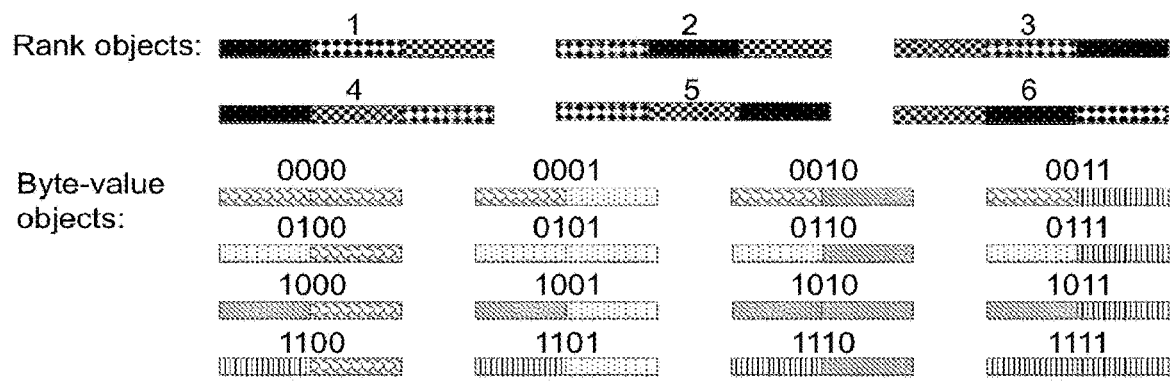

FIGS. 2A and 2B schematically illustrate an example method, referred to as "data at address", of encoding digital data in objects or identifiers (e.g., nucleic acid molecules). FIG. 2A illustrates encoding a bit stream into an identifier library wherein the individual identifiers are constructed by concatenating a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 2B illustrates an example of the data at address method wherein each rank object is combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 2A).

Figure 3A:
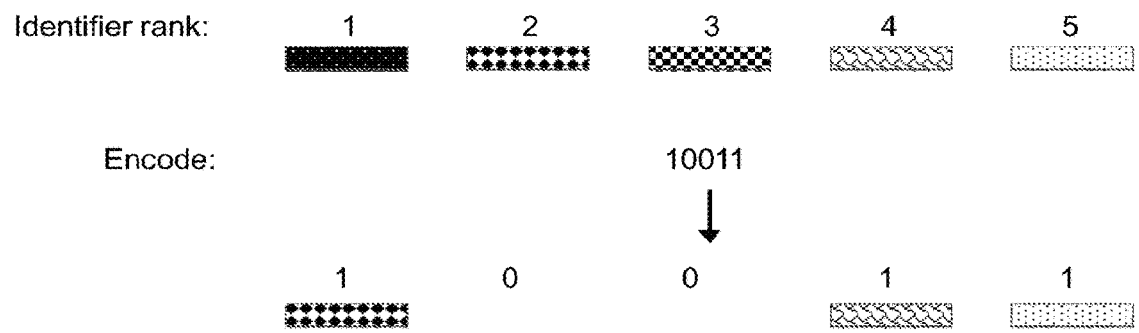
FIGS. 3A and 3B schematically illustrate an example method of encoding digital information using objects or identifiers (e.g., nucleic acid sequences)
Figure 3B:
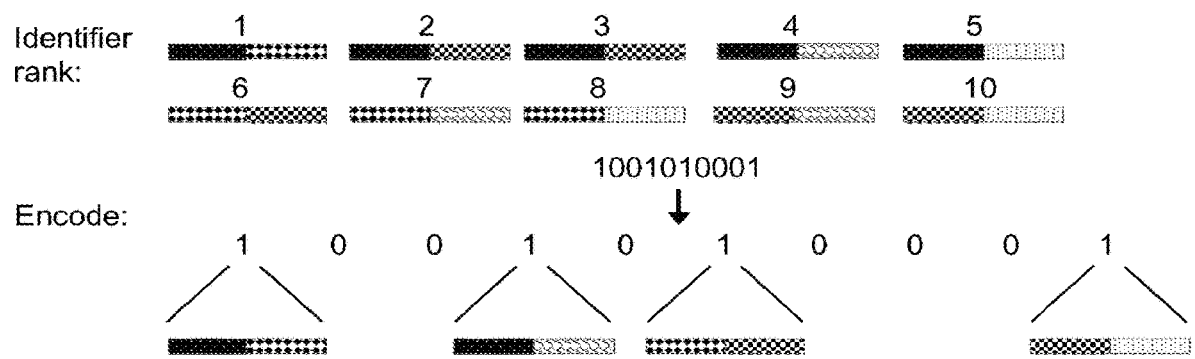

FIGS. 3A and 3B schematically illustrate another example method of encoding digital information in objects or identifiers (e.g., nucleic acid sequences). FIG. 3A illustrates encoding a bit stream into an identifier library wherein identifiers are constructed from single components that specify identifier rank. The presence of an identifier at a particular rank (or address) specifies a bit-value of '1' and the absence of an identifier at a particular rank (or address) specifies a bit-value of '0'. This type of encoding may use identifiers that solely encode rank (the relative position of a bit in the original bit stream) and use the presence or absence of those identifiers in an identifier library to encode a bit-value of '1' or '0', respectively. Reading and decoding the information may include identifying the identifiers present in the identifier library, assigning bit-values of '1' to their corresponding ranks and assigning bit-values of '0' elsewhere. FIG. 3B illustrates an example encoding method where each identifier may be combinatorially constructed from a set of components such that each possible combinatorial construction specifies a rank. Such combinatorial construction enables more information to be written into identifiers than if the identifiers where made from the single components alone (e.g., FIG. 3A). For example, a component set may comprise five distinct components. The five distinct components may be assembled to generate ten distinct identifiers, each comprising two of the five components. The ten distinct identifiers may each have a rank (or address) that corresponds to the position of a bit in a bit stream. An identifier library may include the subset of those ten possible identifiers that corresponds to the positions of bit-value '1', and exclude the subset of those ten possible identifiers that corresponds to the positions of the bit-value '0' within a bit stream of length ten.

Figure 4:
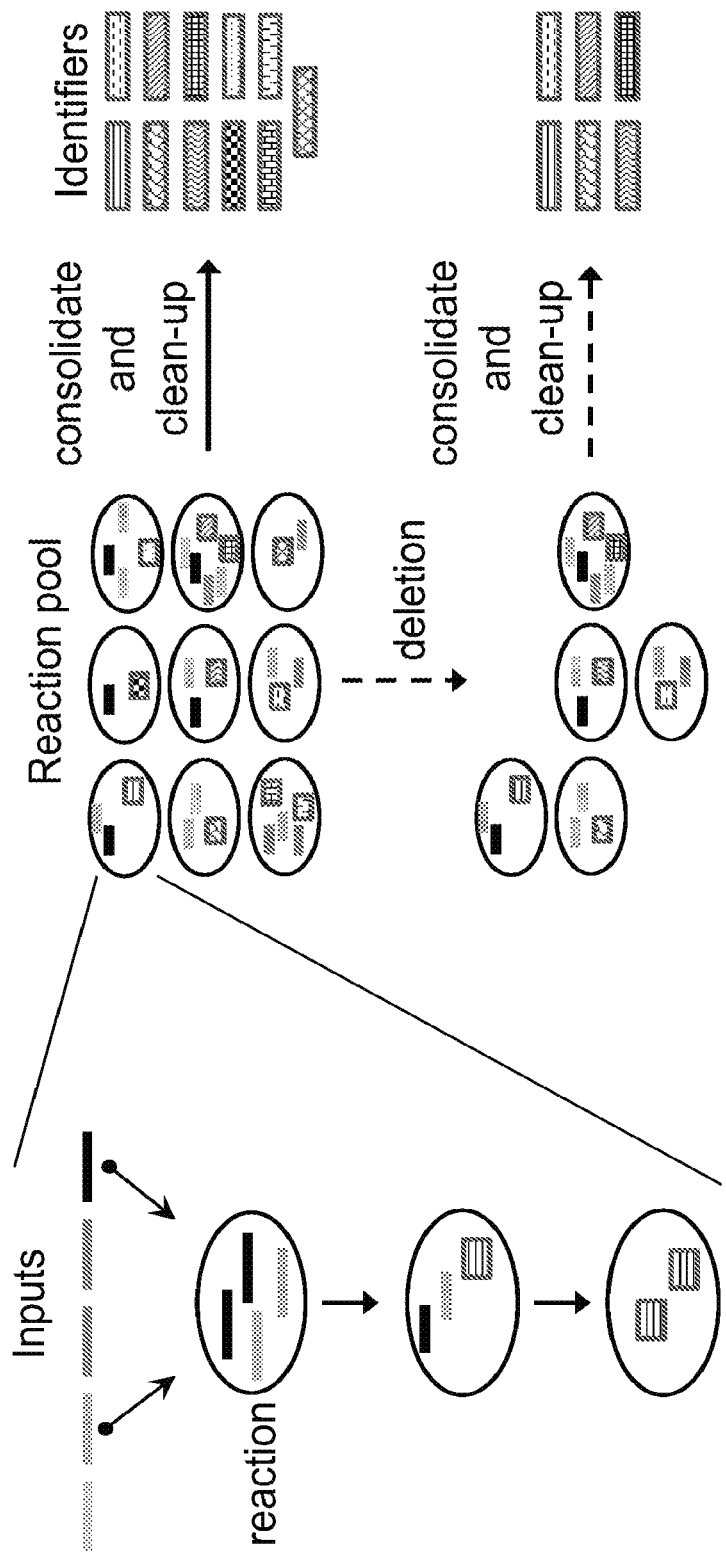
FIG. 4 schematically illustrates an overview of a method for writing information to nucleic acid sequences (e.g., deoxyribonucleic acid)

FIG. 4 shows an overview method for writing information into nucleic acid sequences. Prior to writing the information, the information may be translated into a string of symbols and encoded into a plurality of identifiers. Writing the information may include setting up reactions to produce possible identifiers. A reaction may be set up by depositing inputs into a compartment. The inputs may comprise nucleic acids, components, enzymes, or chemical reagents. The compartment may be a well, a tube, a position on a surface, a chamber in a microfluidic device, or a droplet within an emulsion. Multiple reactions may be set up in multiple compartments. In an example, one or more reaction may be set up to generate a universal library. Reactions may proceed to produce identifiers through programmed temperature incubation or cycling. Reactions may be selectively or ubiquitously removed (e.g., deleted). Reactions may also be selectively or ubiquitously interrupted, consolidated, and purified to collect their identifiers in one pool. Identifiers from multiple identifier libraries may be collected in the same pool. An individual identifier may include a barcode or a tag to identify to which identifier library it belongs. Alternatively, or in addition to, the barcode may include metadata for the encoded information. Supplemental nucleic acids or identifiers may also be included in an identifier pool together with an identifier library. The supplemental nucleic acids or identifiers may include metadata for the encoded information or serve to obfuscate the encoded information.

An identifier rank can comprise a method for determining the ordering of identifiers. The method can comprise a look-up table with all identifiers and their corresponding rank. The method can also comprise a look up table with the rank of all components that constitute identifiers and a function for determining the ordering of any identifier comprising a combination of those components. Such a method may be referred to as lexicographical ordering and may be analogous to the manner in which words in a dictionary are alphabetically ordered. In the data at address encoding method, the identifier rank (encoded by the rank object of the identifier) may be used to determine the position of a byte (encoded by the byte-value object of the identifier) within a bit stream. In an example encoding method, the identifier rank (encoded by the entire identifier itself) for a present identifier may be used to determine the position of bit-value of '1' within a bit stream.

Identifiers may be constructed by combinatorially assembling component nucleic acid sequences. For example, information may be encoded by taking a set of nucleic acid molecules (e.g., identifiers) from a defined group of molecules (e.g., combinatorial space). Each possible identifier of the defined group of molecules may be an assembly of nucleic acid sequences (e.g., components) from a prefabricated set of components that may be divided into layers. Each individual identifier may be constructed by concatenating one component from every layer in a fixed order. For example, if there are M layers and each layer has n components, then up to $C=n^M$ unique identifiers may be constructed and up to $2^C$ different items of information, or C bits, may be encoded and stored. For example, storage of a megabit of information may use $1 \times 10^6$ distinct identifiers or a combinatorial space of size $C=1 \times 10^6$. The identifiers in this example may be assembled from a variety of components organized in different ways. Assemblies may be made from $M=2$ prefabricated layers, each containing $n=1 \times 10^3$ components. Alternatively, assemblies may be made from $M=3$ layers, each containing $n=1 \times 10^2$ components. As this example illustrates, encoding the same amount of information using a larger number of layers may allow for the total number of components to be smaller. Using a smaller number of total components may be advantageous in terms of writing cost.

In an example, one can start with two layers, X and Y, each with x and y nucleic acid sequences (e.g., components), respectively. Each nucleic acid sequence from X can be assembled to each nucleic acid sequence from Y. Though the total number of nucleic acid sequences maintained in the two sets may be the sum of x and y, the total number of nucleic acid molecules, and hence possible identifiers, that can be generated may be the product of x and y. Even more nucleic acid sequences (e.g., identifiers) can be generated if the sequences from X can be assembled to the sequences of Y in any order. For example, the number of nucleic acid sequences (e.g., identifiers) generated may be twice the product of x and y if the assembly order may be programmable. This set of all possible nucleic acid sequences that can be generated may be referred to as XY. The order of the assembled units of unique nucleic acid sequences in XY can be controlled using nucleic acids with distinct 5' and 3' ends, and restriction digestion, ligation, polymerase chain reaction (PCR), and sequencing may occur with respect to the distinct 5' and 3' ends of the sequences. Such an approach can reduce the total number of nucleic acid sequences (e.g., components) used to encode N distinct bits, by encoding information in the combinations and orders of their assembly products. For example, to encode 100 bits of information, two layers of 10 distinct nucleic acid molecules (e.g., component) may be assembled in a fixed order to produce 10*10 or 100 distinct nucleic acid molecules (e.g., identifiers), or one layer of 5 distinct nucleic acid molecules (e.g., components) and another layer of 10 distinct nucleic acid molecules (e.g., components) may be assembled in any order to produce 100 distinct nucleic acid molecules (e.g., identifiers).

Nucleic acid sequences (e.g., components) within each layer may comprise a unique (or distinct) sequence, or barcode, in the middle, a common hybridization region on one end, and another common hybridization region on another other end. The barcode may contain a sufficient number of nucleotides to uniquely identify every sequence within the layer. For example, there are typically four possible nucleotides for each base position within a barcode. Therefore, a three base barcode may uniquely identify $4^3=64$ nucleic acid sequences. The barcodes may be designed to be randomly generated. Alternatively, the barcodes may be designed to avoid sequences that may create complications to the construction chemistry of identifiers or sequencing. Additionally, barcodes may be designed so that each has a minimum hamming distance from the other barcodes, thereby decreasing the likelihood that base-resolution mutations or read errors may interfere with the proper identification of the barcode.

The hybridization region on one end of the nucleic acid sequence (e.g., component) may be different in each layer, but the hybridization region may be the same for each member within a layer. Adjacent layers are those that have complementary hybridization regions on their components that allow them to interact with one another. For example, any component from layer X may be able to attach to any component from layer Y because they may have complementary hybridization regions. The hybridization region on the opposite end may serve the same purpose as the hybridization region on the first end. For example, any component from layer Y may attach to any component of layer X on one end and any component of layer Z on the opposite end.

Combinatorial assembly of two or more components, each from different layers (e.g., X, Y, or Z), to construct identifiers may be achieved using polymerase chain reaction (PCR), ligation, or recombination. In general, any methods for concatenating two or more distinct nucleic acid sequences may be used to construct identifiers in an identifier library. In some instances, all or a portion of the combinatorial space of possible identifiers may be constructed before digital information may be encoded or written, and then the writing process may involve mechanically selecting and pooling the identifiers (that encode the targeted information) from the already existing set. In other instances, the identifiers may be constructed after one or more steps of the data encoding or writing process has occurred (i.e., as information is being written). Methods for constructing identifiers include, but are not limited to, concatenating components with overlap extension PCR (or polymerase cycling assembly), sticky end ligation, recombinase assembly, template directed ligation (or bridge strand ligation), biobricks assembly, golden gate assembly, Gibson assembly, and ligase cycling reaction assembly. Methods for constructing identifiers may also include deleting nucleic acid sequence (e.g., components) from a parent nucleic acid sequence (or parent identifier), or inserting nucleic acid sequences (e.g., components) into a parent identifier. In an example, identifiers may be generated from a parent identifier made up of multiple components. Components may be cleaved from or inserted into a parent identifier to generate a unique identifier. Enzymes for modifying parent identifiers may include double-strand specific nucleases, single-strand specific nucleases, and Cas9.

Enzymatic reactions may be used to assemble components from the different layers. Assembly can occur in a one pot reaction because components of each layer have specific hybridization or attachment regions for components of adjacent layers. For example, a nucleic acid sequence (e.g., component) X1 from layer X, a nucleic acid sequence Y1 from set Y, and a nucleic acid sequence Z1 from set Z may form the assembled nucleic acid molecule (e.g., identifier) X1Y1Z1. Additionally, multiple nucleic acid molecules (e.g., identifiers) may be assembled in one reaction by including multiple nucleic acid sequences from each layer. For example, including both Y1 and Y2 in the one pot reaction of the previous example may yield two assembled products (e.g., identifiers), X1Y1Z1 and X1Y2Z1. This reaction multiplexing may be used to speed up writing time if a plurality of identifiers may be physically constructed. Assembly of the nucleic acid sequences may be performed in a time period that is less than or equal to about 1 day, 12 hours, 10 hours, 9 hours, 8 hours, 7 hours, 6 hours, 5 hours, 4 hours, 3 hours, 2 hours, or 1 hour. The accuracy of the encoded data may be at least about or equal to about 90%, 95%, 96%, 97%, 98%, 99%, or greater.

Writing information into nucleic acid sequences may comprise parsing the information into strings of symbols, mapping the string of symbols to unique identifiers, and generating an identifier library that comprises identifiers corresponding to the string of symbols. The identifier library may comprise an identifier for each identifier rank or it may exclude the identifier for an identifier rank if it corresponds to a selected symbol value (e.g., 0 or 1). Information may comprise a string of symbols. In an example, a string of symbols comprises symbols taken from a fixed finite alphabet of symbols. The string of may be converted to a second sequence of symbols. The second sequence of symbols may comprise a formal data structure. The second sequence of symbols may be parsed into words. The words may be converted into codewords using a codebook. The codebook may be an explicit codebook or an implicit codebook. The codewords may be parsed into a third string of symbols. Each symbol of the third string of symbols may be mapped to a unique identifier. A set of identifiers (e.g., an identifier library) may be enumerated or defined such that each symbol may be encoded in one or more identifiers. The set of identifiers (e.g., identifier library) may include, or have appended to it, information related to the one or more codebooks, data structure, and combinatorial space.

The formal data structure may include a tree, a trie, a table, set, a key-value dictionary, or a set of multidimensional vectors. The formal data structure may be able to be queried by one or more query types including, but not limited to, range queries, rank queries, count queries, membership queries, nearest neighbor queries, match queries, selection queries, or any combination thereof. The second sequence of symbols comprising the formal data structure may be parsed into a sequence of words to minimize the number of identifiers used to encode a bitstream. Each bit of a source bitstream may be associated with an identifier in a combinatorial space.

Figure 5:
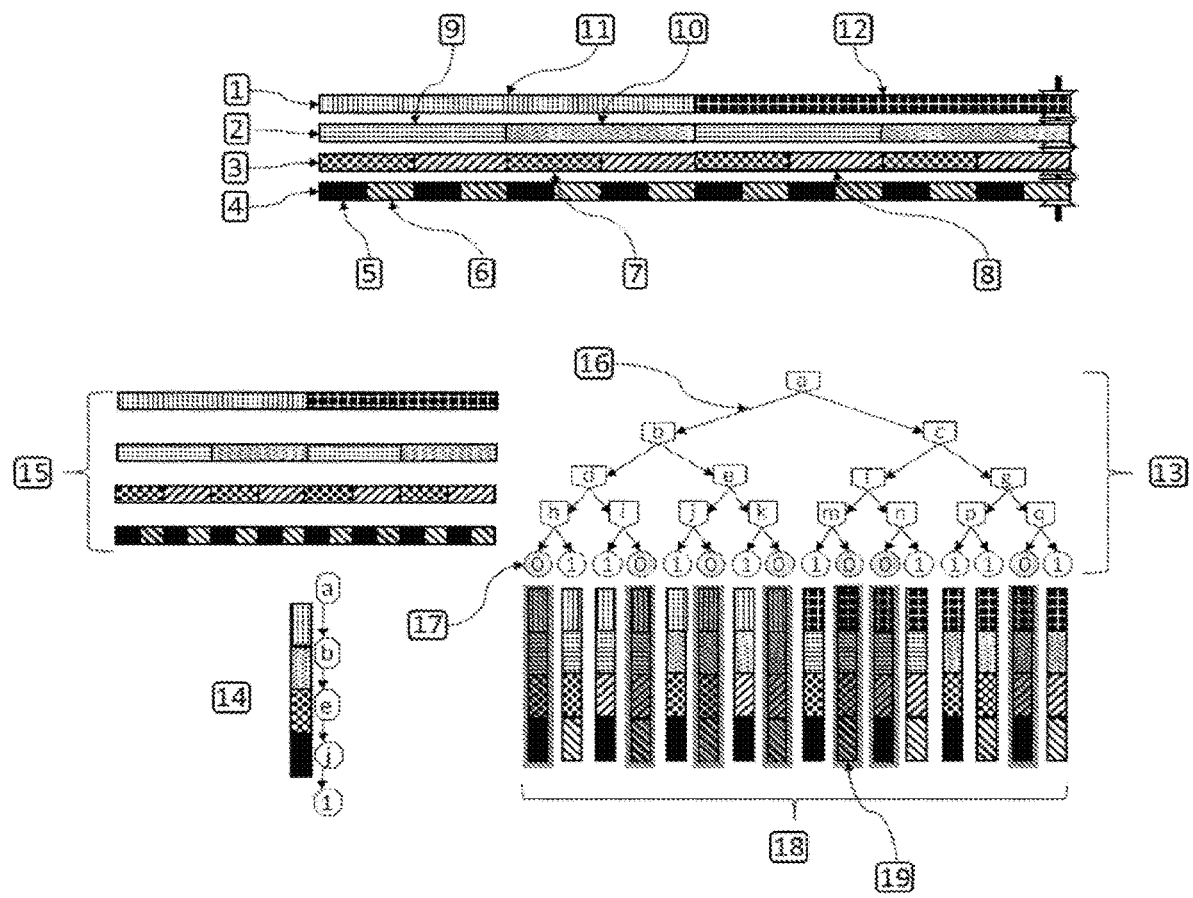
FIG. 5 schematically illustrates an example combinatorial space of identifiers organized as an n-ary tree of m levels.

The combinatorial space of identifiers may comprise the unique identifiers that may be produced by one or more construction algorithms from a library of T total components. In one embodiment, the construction algorithm may produce identifiers using a Cartesian product scheme comprising M layers where the i-th layer contains Ni components. The number of identifiers in a combinatorial space may be dependent upon the number of layers, the number of components in each layer, and the method used to assemble the identifiers. FIG. 5 illustrates an example combinatorial space of identifiers using a product scheme comprising M layers and N components in each layer. In this example, M=4 and N=2. Items 501-504 in FIG. 5 show the layers in this example. Items 511 and 512 show the two components in layer 1 in this example. Similarly, items 509-510, 507-508, and 505-506 show components belonging to layers 2, 3, and 4. The components are laid out in a repeating pattern so as to illustrate the combinatorial space of sixteen distinct identifiers arising from this scheme. The steps in an instance of the combinatorial algorithm for generating each identifier in the combinatorial space may be illustrated as a tree diagram, shown in item 513. The tree diagram may be divided into M layers. Each layer contains a node representing the choices available for a component in that layer. For example, in layer 1, the two arrows arising from the node labeled "a" illustrate the choice of two components in layer 1, shown by items 511 and 512. In layer 2, the arrows arising from node b represent the choice of components in layer 2, shown as elements 509 and 510, conditioned on the choice of component 511 in layer 1. The left and right arrows arising from each node correspond to the pattern of components illustrated in the layers in item 515. The arrows arising from each node are ordered according to the component ranking defined for the product scheme. Each path down the tree diagram, starting from the top most node labeled "a" to any of the bottom nodes corresponds to a distinct identifier. One such path is illustrated by item 514.

The combinatorial space of all identifiers, a total of 16 in this example, is shown by item 518. Item 517 shows one bit value in an example bitstream that may be encoded using this combinatorial space. Each bit in the bitstream corresponds to a distinct identifier, depicted under the bit. In one embodiment, the value of the bit is represented by the inclusion or exclusion of the identifier from a constructed identifier library. To encode the bitstream, all identifiers corresponding to bits having value "1" may be constructed and pooled, while those corresponding to bits with value "0" may be excluded. The excluded identifiers are marked with dark overlays: item 519 shows one such excluded identifier corresponding to the $10^{th}$ bit which has a value of "0."

Information may be encoded into identifiers with a data at address scheme, abbreviated as the DAA scheme. A source bitstream may be divided into words of a fixed length L. The bitstream may then be interpreted to be a symbol stream of L-bit symbols (e.g., each symbol comprises L-bits). A unique identifier may be constructed for each symbol in the symbol stream (i.e., for each symbol comprising L-bits) and pooled or grouped together. In one embodiment, the identifiers may be constructed using a product scheme comprising M layers with N components in each layer. Each identifier may be factored into two parts (or objects). The first part may comprise up to k<M layers and may provide information regarding the address of the symbol. The second part of the unique identifier may comprise components from M-k layers and may provide information regarding the value of the symbol. Alternatively, or in addition to, a source bitstream may be divided into a stream of words of L-bits in length. A codebook may be used to map the words to codewords over a nucleic acid alphabet comprising the four bases A, T, C, and G. Each codeword may be constructed of the four bases. The identifiers for each L-bit word may be constructed by assembling or concatenating the corresponding synthesized codewords to an assembly of components specifying the address of that codeword.

Figure 6:
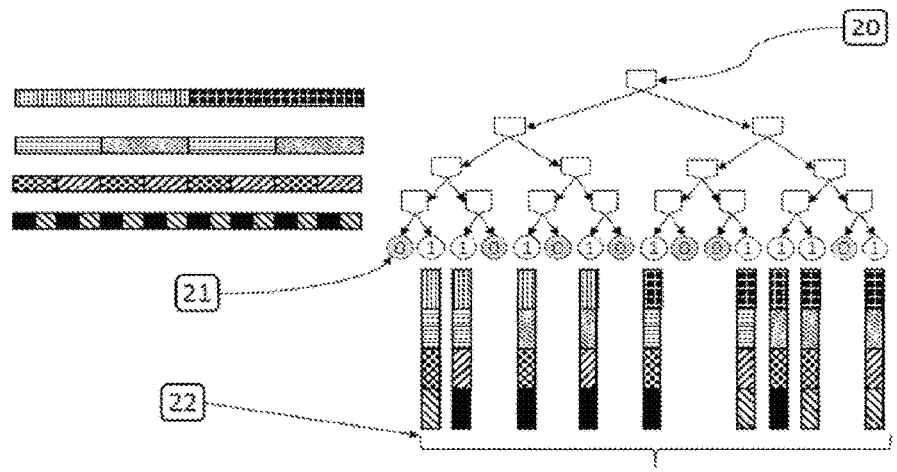
FIG. 6 schematically illustrates an example method for minimizing the number of identifiers to be constructed for writing a bitstream.
Figure 6:
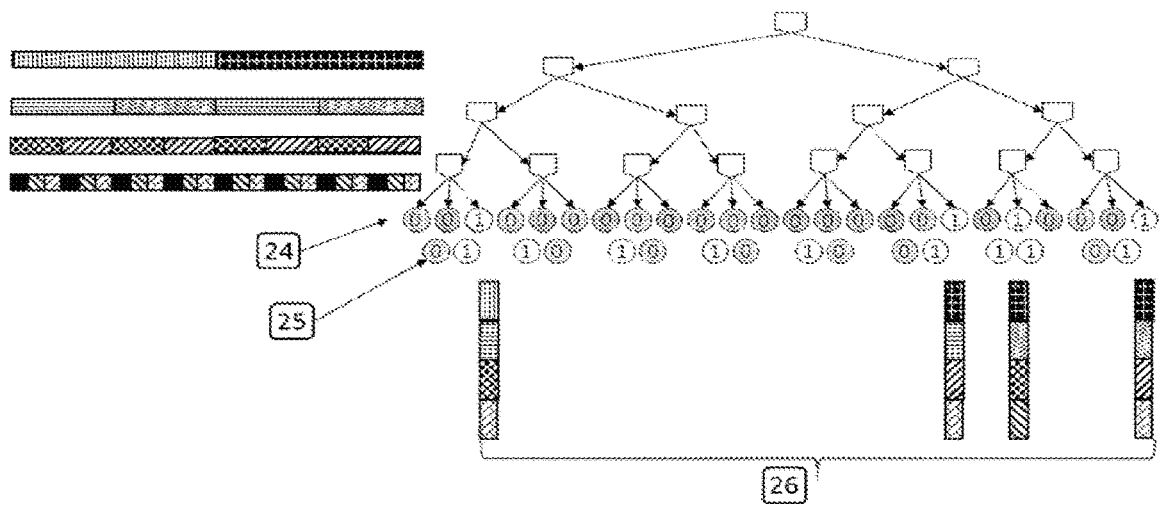

Prior to writing the source bitstream into an identifier library, the source bitstream may be encoded into an intermediate bitstream. The source bitstream may be divided into words. Another codeword may be chosen to replace the word. The length of the codeword may be greater than, equal to, or smaller than the length of the word it corresponds to. In one embodiment, each word X containing some number N(X) of Y symbols may be replaced with a codeword containing a smaller or larger number of Y symbols. For example, a word containing N(X) "1" symbols may be replaced with a codeword containing fewer than N(X) "1" symbols. In an example encoding method, this may result in a reduction of the identifier library size used to encode the given digital information. Minimizing the number of physically assembled identifiers may reduce the time to write information into identifiers and read information encoded in identifiers. FIG. 6 schematically illustrates an example method for minimizing the number of identifiers to be constructed in order to write a bitstream using expansion codewords. A bitstream may be divided into words, and in this example each word may be of a fixed length of two bits. The list of words comprising 2 bits includes '00', '01', '10', and '11'. Each word may appear in the bitstream zero or more times. For example, the bitstream '0110101010011101' may be divided into 2-bit words {01, 10, 10, 10, 10, 01, 11, 01} where the '00' word appears zero times, the '01' word appears three times, the '10' word appears four times, and the '11' word appears once. The total number of "1" symbols in this sequence of words is nine, indicating that the encoding method may necessitate the assembly of nine distinct identifiers to represent the bitstream. The words may be, however, recoded so that fewer identifiers may be used to encode the given bitstream.

Digital information to be encoded into nucleic acids may first be converted into a sequence of symbols, and then reorganized into a formal data structure amenable to one or more query types. This data structure may then be serialized into a second string of symbols. This second string of symbols may be coded using one or more codebooks for one or more purposes including error protection, encryption, write speed optimization, or identifier library size minimization. FIG. 6 shows an example method for minimizing the identifier library size. Item 620 shows the tree diagram representation of a combinatorial space, the notation for which was described in FIG. 5. In this example, item 621 shows a bit value from a bit stream of 16 bit values. Item 622 shows the set of identifiers corresponding to the bit values in the bitstream with value "1." Thus, as is, this encoding may require the assembly of nine distinct identifiers corresponding to the nine bits with value "1." The size of this identifier library, however, may be reduced by re-encoding the bitstream using a codebook that maps two-bit words to three-bit codewords, such that the new three-bit codewords have fewer "1" symbols, leading to a smaller identifier library.

In an example of this re-encoding method, the bitstream may be divided into eight sequential contiguous two-bit words, and the number of occurrences of each two-bit word may be recorded. In this example, these counts are shown in table 623, under the Count column. All of the possible three-bit codewords are listed as columns to form a matrix, where cell (i, j) contains the cost of mapping a two-bit word i to a distinct three-bit codeword j. This cost may be computed by taking the product of the number of "1" symbols in the codeword and the number of occurrences of the word in the original bitstream to compute the number of identifiers that may be used to be constructed using this word-to-codeword substitution. For example, the word "01" occurs thrice in the original bitstream. If it is mapped to the codeword "111," then the number of "1" symbols due to this substitution in the re-coded bitstream may increase to 12 from 3. These costs are calculated for all such possible substitutions. The matrix so obtained, shown by item 623, may be translated into a weighted bipartite graph and a minimal weight perfect matching may obtained using algorithms like the Kuhn-Munkres algorithm. The minimal perfect matching may be equivalent to choosing exactly one cell in each row and column in the matrix 623 such that the sum of all the chosen cells may be minimized. The cost of each cell in one such minimal re-encoding is shown in table 623 with shaded cells. In this minimal re-encoding, the word "00" is mapped to the codeword "011", "01" to "001", "10" to "000", and "11" to "010". The new bitstream so coded has a total of four "1" symbols. The cost may be thus reduced from nine in the original bitstream to 4 in the new re-encoded bitstream. The new bitstream comprises three-bit codewords shown in the tree diagram by item 624. Each three-bit codeword uniquely maps a two-bit codeword from the original set of two-bit codewords, depicted by item 625. Item 626 shows the new identifier library to be assembled.

Figure 7:
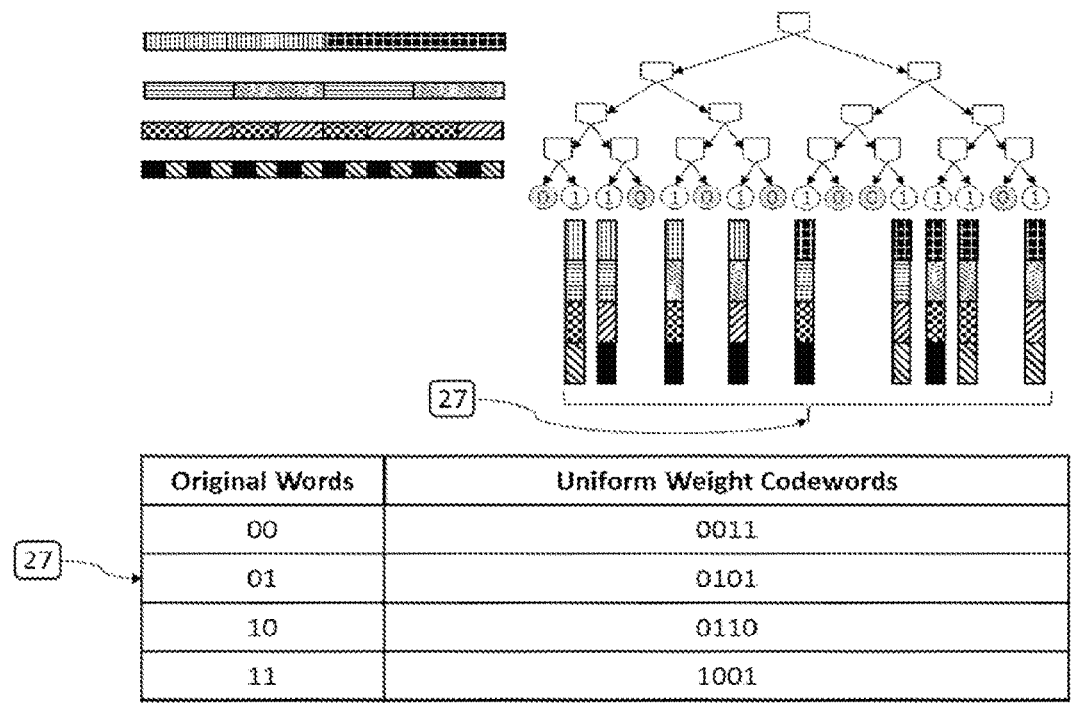
FIG. 7 schematically illustrates an example method for remapping words to codewords to ensure uniform weight codewords for error detection.
Figure 7:
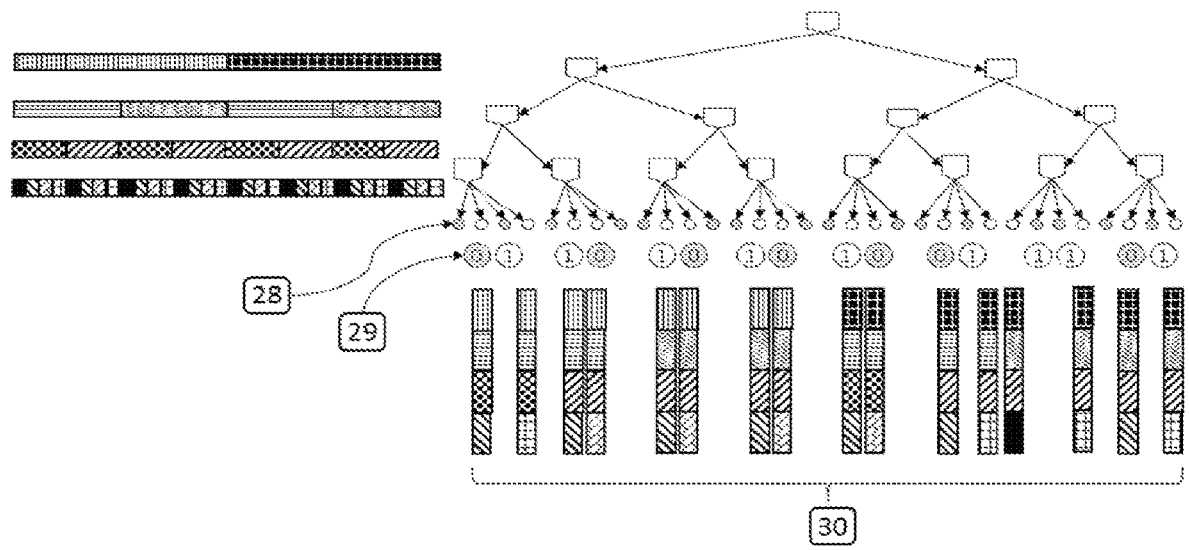

Choice of symbols encoding digital information can enable the detection and or correction of encoding errors. Re-encoding a symbol stream to include error protection symbols computed from the symbols in the original string can allow for detection or correction of errors encountered during the process of writing the symbol stream using nucleic acids. In one embodiment, the symbol stream may be divided into fixed length words and one or more error protection symbol strings may be computed from each such word and appended to the word to obtain a recoded string. For example, the number of identifiers to be constructed in a fixed length block of K identifiers may be counted. If this count is even, then an extra identifier may be added to the block, and if the count is odd, then no such extra identifier may be added. The combinatorial space may be chosen so that these extra identifiers can be accommodated. When such a block of identifiers is read, then any write errors where an identifier is erroneously omitted or where an extra identifier is erroneously added may be detected because such an event may negate the required property that each block have an odd number of identifiers. In another embodiment, the number of identifiers in any fixed length block of K identifiers is counted, and K minus the count is computed. This value, called the error protection value, may be appended to the block, and encoded. The combinatorial space may be chosen so that identifiers corresponding to these error protection values can be accommodated. In this case, when the block and the error protection value is read, then any errors where an identifier has been erroneously omitted may be detected. If the omitted identifier may be in the original block, then this may be reflected by the mismatched error protection value. If the omitted identifier is in the error protection value, then the lower value may indicate that the error may be in the error protection value. If there is an error in both the block and the value, then the mismatch may lead to the detection of the error. In another embodiment, the symbol stream may be divided into fixed length words of W symbols. Each word may then be remapped to a codeword such that each codeword leads to the construction of a fixed number V of identifiers. FIG. 7 schematically illustrates this uniform weight codeword error detection scheme. Item 727 shows the identifier library that may be constructed to encode the bitstream shown in the tree diagram in FIG. 7. In the original bitstream, for any fixed word length W, the number of identifiers is not constant: for W=2 for example, there may be one identifier in each of the first six words and two identifiers in the second word. Table 727 shows a re-encoding example codebook that maps words of length W=2 to codewords of length V=4. The example codebook maps words "00", "01", "10", and "11", to codewords "0011", "0101", "0110", and "1001", respectively. Because all codewords have exactly two "1" symbols, and because the word and codeword lengths are fixed, the resulting bitstream has exactly two "1" symbols in every codeword of length four symbols. This is illustrated in the example tree diagram for the re-encoded bitstream shown in 730. Item 729 shows the words that map to distinct codewords, such as the one shown by item 728. Because of the fixed rate and number of identifiers expected in the identifier library, any missing identifier errors can be detected at the time of decoding.

Writing time may be minimized by interpreting the input bitstream to be a multi-value boolean function. In one embodiment, the input bitstream may be divided into blocks of fixed length L before subjecting it to writing time minimization. The input bit stream may be subjected to a heuristic logic minimization algorithm, such as espresso-mv or mvsis, to obtain a multivalue algebraic expression representing the source bitstream. In one embodiment, the input bitstream may be encoded using an M-layer product scheme for constructing identifiers. In this embodiment, the input bitstream may be interpreted as an M-input multivalue Boolean function with a single Boolean output. For a Boolean function, the 1-set of the function may be defined as the set of all inputs to the function on which the function outputs a value of "1." Using techniques from logic minimization, the Boolean function may be transformed into an algebraic expression comprising a sum-of-products formula. The expression obtained includes every identifier in the 1-set of the source bitstream. Each term in the expression may be converted into a set of identifiers that may be executed (constructed in a multiplex fashion) in a single reaction compartment (e.g., partitions or reaction vessels). The expression obtained may be used to minimize the number of reaction compartments used and maximize the number of identifiers assembled in a single compartment. The expression may also be used to minimize the total time used to set up the identifier assembly reactions, for example if writing time may be proportional to the number of reaction compartments top set up. A similar method may be used to set up reactions used to query a subset of bits from the source bitstream.

Figure 8:
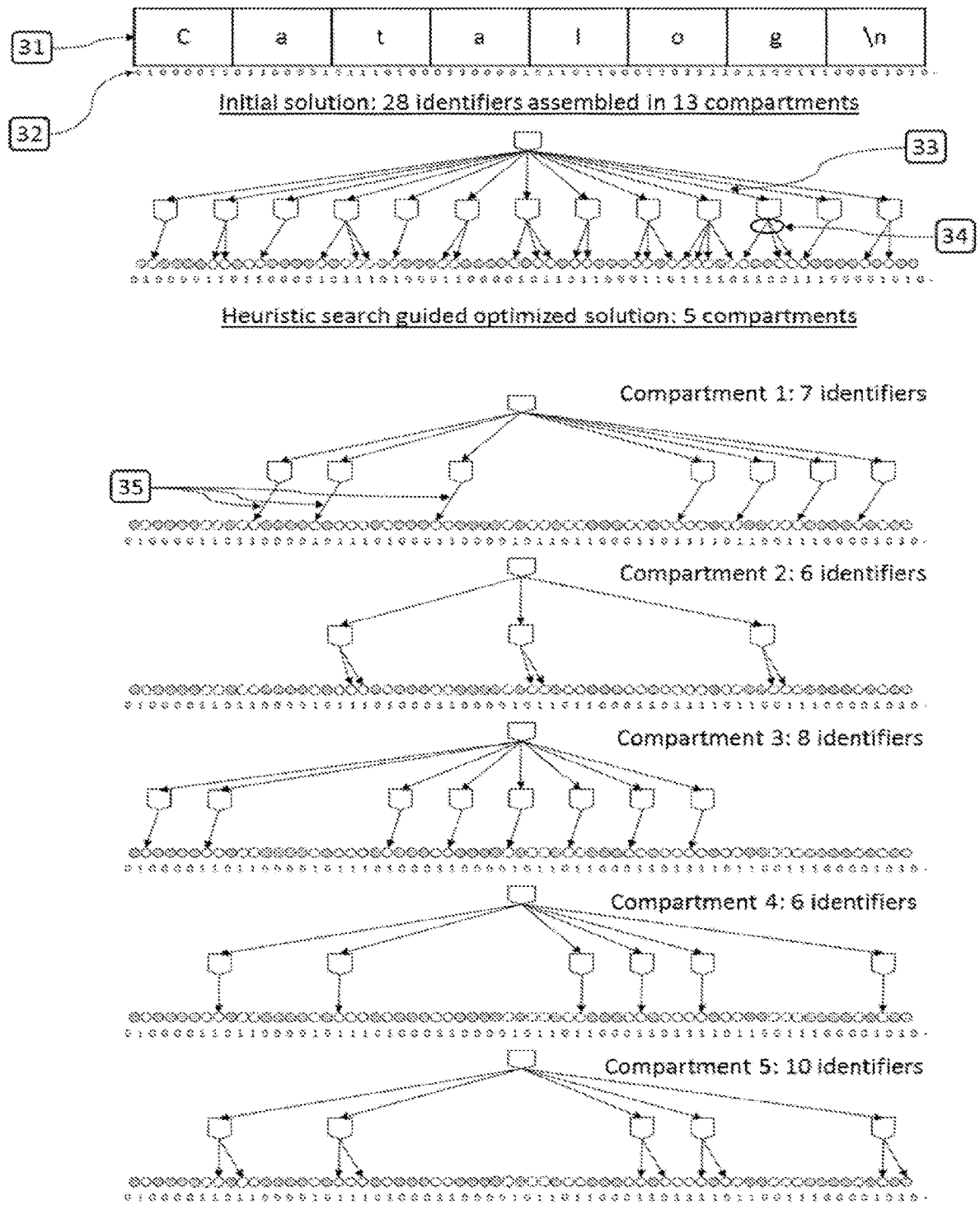
FIG. 8 schematically illustrates an example method for minimizing writing time by minimal reaction set generation.

FIG. 8 schematically shows the output of an example scheme for reaction set minimization. Consider a bitstream of length L and a Product scheme with M layers, where layer i has Ni components respectively, such that the product of all Ni is at least L. Each component in a layer may be labeled with an integer in the range 0 to Ni-1. The bitstream of length L may be interpreted as a Boolean function F of M variables, where each variable Vi may take one of Ni values, between 0 and Ni-1. All combinations of these variable-values may be represented as M-dimensional vectors, where the value of variable Vi may be represented as an integer in the i-th dimension of the vector. Using these vectors as inputs, and each bit value in the bitstream as the output, a Boolean function F may be defined. If a Product scheme has a combinatorial space of size larger than L, then the output of F at those additional input vectors may be defined to be a distinct "don't-care" value.

FIG. 8 shows an example where information depicted in item 831, representable as a bit stream of length 64 bits as shown in item 832, is encoded though a Product Scheme comprising two layers, with 13 and 5 components in each layer. The Boolean function F defined comprises 65 possible input vectors, where each vector may be two-dimensional. Each dimensional variable V1 and V2 takes 13 and 5 values, where V1 takes values in the range 0 to 12 and V2 takes values in the range 0 to 4. The set of all possible variable-value combinations may be depicted as a tree diagram. The cases where the output of the function F as defined above is a "1" may also be depicted as a tree diagram, comprising a subset of the arrows. This tree diagram is shown at the top in FIG. 8. The set of variable-value combinations where F takes value "1" coincides with the set of identifiers required to be constructed to encode the bitstream. Thus, the paths from the root of the tree diagram to the individual values depicted in the tree diagram coincide with the set of reactions required to assemble each identifier. In this example, the arrows indicated by item 833 and 834 show one set of paths corresponding to three bits in the bitstream to be encoded. These three paths also correspond to three identifiers required to be assembled to encode those three bits. Because the vectors describing these "1" values of F differ in their second dimension, taking values 0, 3, and 4, their corresponding identifiers also differ in the second layer, and take the zeroth, third, and fourth components in the second layer. All three identifiers have the same component, corresponding to the value V1=10, in their first layer. Consequently, all three identifiers may be assembled in a single reaction with component V1=10 and components V2 from the set {0, 3, 4}. The resulting set of combinations, (10, 0), (10, 3), and (10, 4) correspond to the correct set of identifiers to be constructed. From the tree diagram, 13 such reaction sets are required to encode the given bitstream. The tree diagram may, however, be factored into a set of tree diagrams, using heuristic-guided search, such that all identifiers in each of the factor trees may be assembled in single reactions. For example, a greedy heuristic may be used where all values of V1 for some value V2=v are grouped together, such that all identifiers assembled correspond to "1" values of F. Item 835 shows a set of values where V2=0 and V1={3, 4, 5}. In another embodiment, multiple heuristics may be combined to obtain a minimal set covering the "1" values of F. In another embodiment, heuristic techniques from logic minimization [Brayton et al. *Logic Minimization Algorithms for VLSI Synthesis* Kluwer Academic Publishers, which is entirely incorporated herein by reference] may be used to minimize the number of reaction sets. The five tree diagrams shown under the label "Heuristic search guided optimized solution" together cover all the "1" values of F. As a result, five reaction sets may be used to set up in five separate compartments, rather than 13 compartments in the original tree diagram.

Each symbol (e.g., bit in a bitstream) may be mapped to one or more of the unique identifiers in the combinatorial space. A set of identifiers may be determined and enumerated in computer memory or generated by combinatorially assembling the set of identifiers into an identifier library. When digital information is presented to be encoded into an identifier library, in one embodiment, each symbol in the digital information can be mapped to a distinct identifier in the combinatorial space. There may be a vast number of ways to map a given bitstream to a combinatorial space generated from a combinatorial scheme (e.g., product scheme or permutation scheme, or some other scheme), and comprising some chosen number of components. Some of these mappings may be beneficial in reducing the number of queries when the encoded data is later queried. Specifically, mappings that preserve locality of symbols in the original symbol stream after mapping the symbols into the combinatorial space may be useful in reducing the number of accesses used to answer a query. An access may be a request to select a set of identifiers from an identifier library, or pool of identifiers, described by a single nucleic acid sequence referred to as the access sequence. In one embodiment, when an identifier is assembled from components, one may access the set of all identifiers containing a particular component with a single access. The nucleic acid sequence of the component may be the access sequence in this example. The family of mappings that preserve locality of the original symbols are called isometric mappings. Moreover, a single digital message may be mapped to two orthogonal combinatorial spaces, each with its own component libraries, resulting in two orthogonal identifier libraries representing the same digital message. The two mappings may be beneficial in reducing the number of accesses to two sets of queries. This type of encoding using a plurality of mappings may be called multi-encoding, and may be called dual encoding when the number of mappings may be fixed to two mappings.

Figure 9:
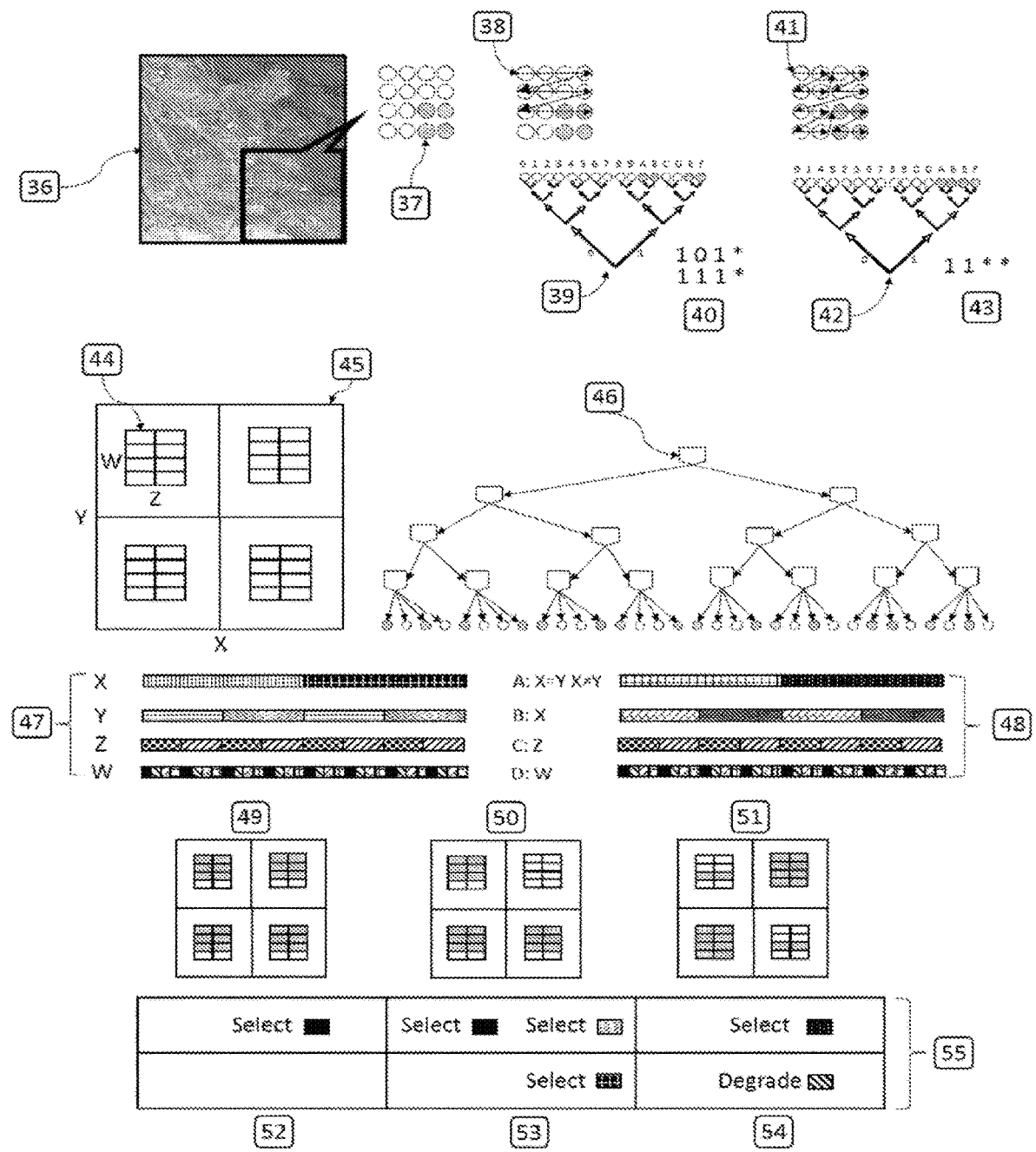
FIG. 9 schematically illustrates isometric mapping of addresses to identifiers and dual encoding of data.

FIG. 9 schematically illustrates isometric mapping of addresses to identifiers and dual encoding of data. The process of encoding a digital message may comprise converting the information into a sequence of symbols and converting the sequence of symbols into a second sequence of symbols with a formal data structure amenable to one or more query types. FIG. 9 shows an example where the digital information to be encoded may be a two-dimensional image shown in item 936. Item 937 shows a schematic of the image, where the shaded circles denote the lower right quadrant of the image. The original sequence of symbols, the bit values in this case, may be encoded in the order they are presented. This order is depicted in item 938 and the resulting tree diagram for a Product Scheme is depicted in item 939. If the lower right quadrant of the image is to be read, then this may result in querying the shaded circles in the encoded bitstream. In the combinatorial space, this may translate into a query for four identifiers. In this example, assuming each layer in the Product Scheme has two components each, two queries may be used: a query for all identifiers starting with the components 101* and all identifiers starting with the components 111*, where * denotes that an identifier with any component in that layer may be returned as an answer the query. Two queries are used because the lower quadrant of the image may be mapped to the combinatorial space in a way such that nearby regions of the image are mapped to identifiers that are not nearby in the combinatorial space.

Item 941 shows an alternative mapping where nearby regions of the image are mapped to nearby identifiers. This may be called an isometric (i.e., distance preserving) mapping. In this case, one query may be used: all identifiers starting with 11 are sufficient to answer the query. This may be generalized to multidimensional data structures, including multi-column tables, tries, trees, sets, and vectors. More generally, the product scheme encodes data in a uniquely multidimensional way, because of which the querying of many types of data may be optimized and parallelized. Item 945 shows a multidimensional data set comprising four dimensions X, Y, Z, and W. Each of X, Y, Z in this example take two values and the fourth dimension W takes four values. Each four-dimensional vector corresponds to a single bit value in this example. Generally, this may be extended to integer values. Item 946 shows a tree diagram for encoding this 32-bit bitstream using a four-layer product scheme. Specifically, the Product scheme structure preserves the dimensionality of the original data structure: the dimensions X, Y, Z, may be mapped to binary layers, and the dimension W which takes four values may be mapped to a layer with four components. Furthermore, items 947 and 948 show two mappings of the data set to the same combinatorial space. The two mappings differ in which regions of the data structure are mapped to proximal regions of identifiers in the combinatorial space. In the mapping of item 947, the data regions corresponding to X=0, Y=0 and X=1, Y=1 are mapped to identifiers that are not proximal, whereas in the mapping of item 948, they are mapped to proximal identifiers. Item 949 shows a possible query for the unshaded bit values. Item 952 shows the sequence of component accesses used to retrieve these bit values, using the mapping shown in item 947. In this example, the query may be answered using a single access for component 0 in layer W. Item 50 shows a more complex query, which may be answered by two parallel accesses for components W=0 and Y=1, followed by a serial access to component X=1. This answers the query for all unshaded values in item 950. Item 951 shows a more complex query. Using the mapping of item 947, this query may require more than four accesses. Using the mapping of item 948, however, this query may be answered using one access followed by a single degradation step. The degradation step deletes all identifiers that comprise a specific pattern. In this example, the pattern is component 1 from layer W. In this way, the mapping of the data structure to the combinatorial space may reduce the complexity of answering data queries. In some embodiments, multiple mappings of the same data structure may be encoded in a single pool of identifiers using an orthogonal or distinguishable set of components. This is depicted in the mappings shown in items 947 and 948: two identifier libraries may encode the data structure shown in item 945**, and queries may be answered using either mapping, depending on the number of accesses used by each mapping.

Digital information that is presented for encoding into an identifier library may contain information that may be protected from unauthorized decoding. The methods of writing information into DNA described herein may provide an additional level of protection against unauthorized decoding of the encoded information. Biochemical methods of encryption, authorization, obfuscation, and destruction may be used to protect the encoded information. In one embodiment, information may be encoded and obfuscated by inclusion of decoy identifiers into the identifier library. A decoy identifier may be an identifier that does not encode any information that is part of the original digital information presented for encoding and is included to make the process of decoding prohibitively expensive and intractable without possession of the decoy key. A decoy key may be a set of sequences of components such that selecting identifiers comprising the components can isolate some or all of the identifiers that constitute the original identifier library, or conversely such that deleting all identifiers comprising the components can delete some or all decoy identifiers.

Figure 10:
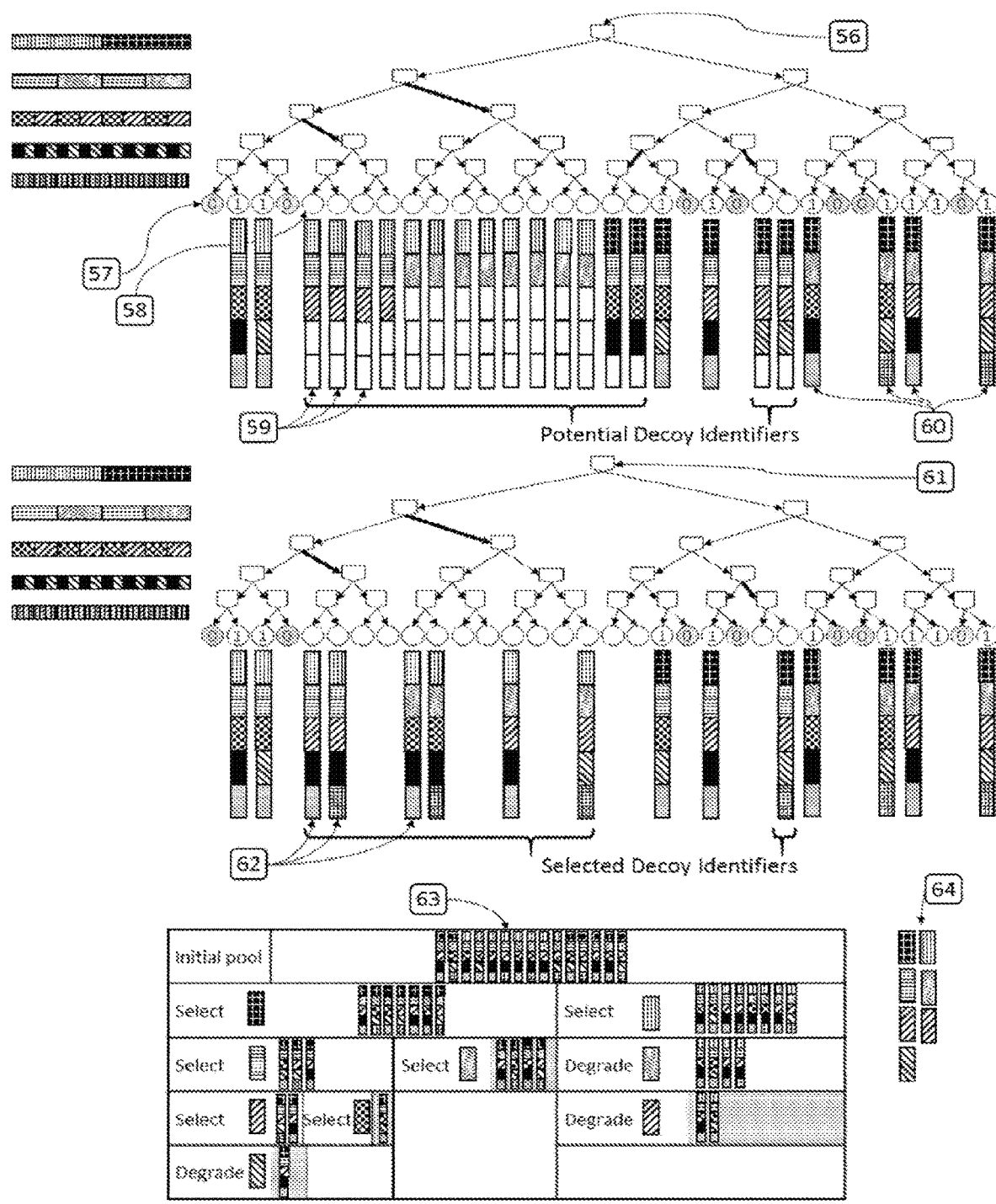
FIG. 10 schematically illustrates an example method for masking encoding and decoding for protection against unauthorized decoding.

FIG. 10 schematically illustrates an example method for masking encoding and decoding for protection against unauthorized decoding. A bitstream may be encoded into unique identifier and an identifier library may be assembled. Additional nucleic acid sequences may be added to the identifier library. The additional or supplemental nucleic acid sequences may be of similar length to and may be indistinguishable from the unique identifiers without a key to decode the information. Decoding the information may include subjecting the pool of identifiers to one or more selecting and/or degrading targeted nucleic acid sequences until the unique identifiers have been extracted from the supplemental nucleic acid sequences Item 1056 shows the tree diagram depicting the encoding of a bitstream using a five-layer Product Scheme, where each layer contains two components. The original bitstream is shown by item 1057, and comprises 16 bits, shown as circles circumscribing values. This bitstream is, however, encoded in a larger combinatorial space than used to encode 16 bits, with the remaining undefined symbols shown as empty circles, as indicated by item 1058, for example. The five-layer binary scheme shown enables a combinatorial space of 32 distinct identifiers. Some of the identifiers corresponding to the "1" bit values in the original bitstream are shown in item 1060. Some of the remaining identifiers that do not correspond to any bit values in the original bitstream are indicated by item 1059, and are labeled as "Potential Decoy Identifiers." These identifiers are shaded so as to show the minimal number of components that are sufficient to distinguish them from identifiers corresponding to bit values in the original bitstream. These identifiers are called potential decoy identifiers. The choice of which identifiers are chosen to be decoy identifiers and which identifiers are chosen to correspond to a bit value in the original bitstream may be arbitrary in this example, but may be governed by data structure of the bitstream, query constraints, and the strength of obfuscation or concealing used. From the set of potential decoy identifiers, some decoy identifiers are chosen to be included in the identifier library encoding the original bitstream, as shown in item 1062, and are labeled as "Selected Decoy Identifiers." The bitstream may be encoded into a pool of identifiers containing both identifiers corresponding to bit values and decoy identifiers that do not correspond to any bit value in the original bitstream. Thus, any unauthorized decoding of the pool may not be able to faithfully decode the original bitstream in the absence of information about the set of selected decoy identifiers. The set of sequences of components that describe the chosen set of decoy identifiers may be called the decoy key. The decoy key for this example is shown by item 1064 and contains two sequences of components: components 1, 0, 1, 1 from layers 0-4 and components 0, 1, 1 from layers 0-3. The decoy key may be interpreted in the following way. Each component in a sequence of components in the decoy key corresponds to an access query. All identifiers matching that component query are accessed from the current pool. The last component in the sequence of components may be not accessed; instead, it may be used to delete all identifiers that match that component from the current pool. Table 1063 shows the steps required to execute the decoy key shown in 1064. Starting from the pool of all identifiers depicted in the tree diagram 1061, a series of accesses followed by deletions result in the survival of the exact identifier library corresponding to the original bitstream: all decoy identifiers are removed. The surviving identifiers are shown in the shaded cells of Table 1063.

Systems for Encoding Information to and Decoding Information from Nucleic Acid Sequence(s)

A system for encoding digital information into nucleic acids (e.g., DNA) can comprise systems, methods and devices for converting files and data (e.g., raw data, compressed zip files, integer data, and other forms of data) into bytes and encoding the bytes into segments or sequences of nucleic acids, typically DNA, or combinations thereof.

In an aspect, the present disclosure provides systems for writing information into nucleic acid sequence(s). A system for writing information into nucleic acid sequence(s) may comprise an assembly unit and one or more computer processors. The assembly unit may be configured to generate an identifier library encoding a sequence of symbols. The identifier library may comprise at least a subset of a plurality of identifiers. The one or more computer processors may be operatively coupled to the assembly unit. The computer processors may be individually or collectively programmed to (i) convert the sequence of symbols into codewords using one or more codebooks, (ii) parse the codewords into a coded sequence of symbols, (iii) map the coded sequence of symbols to the plurality of identifiers, (iv) direct the assembly unit to generate an identifier library, and (v) direct the assembly unit to append a description of the one or more codebooks and the plurality of identifiers to the identifier library. Each symbol of the coded sequence of symbols may be encoded by one or more identifier(s), In another aspect, the present disclosure provides integrated systems for nucleic acid-based data storage. A integrated system for nucleic acid-based data storage may comprise a data encoding unit, a storage unit, a reading unit, and one or more computer processors. The data encoding unit may be configured to write digital information into nucleic acid sequences. The storage unit may be configured to store the nucleic acid sequence encoding the digital information. The reading unit may be configured to access and read the digital information encoded in the nucleic acid sequences. The one or more computer processors may be coupled to the data encoding unit, the storage unit, and the reading unit. The one or more computer processors may be individually or collectively programmed to (i) direct the data encoding unit to encode the digital information into the nucleic acid sequences, (ii) direct the storage unit to store the digital information encoded into the nucleic acid sequences, and (iii) direct the reading unit to access and decode the digital information stored in the nucleic acid sequences. The digital information may be encoded in nucleic acid sequences in the absence of base-by-base nucleic acid synthesis.

The system may comprise one or more computer processors and a human machine interface (HMI) to control and program the computer processors. The system may encode and recode digital information using any method as described elsewhere herein. The system may generate a list of identifiers that make up the identifier library. Alternatively, or in addition to, an external computer processing unit may generate a list of identifier sequences that make up the identifier library. The system may have an interface to receive the list of identifier sequences. The interface unit may convert the list of identifier sequences into instructions for downstream units or modules of the system to generate and pool the identifiers.

The system may have an assembly module. The assembly module may be configured to receive a plurality of substrates (e.g., components) and reactants (e.g., enzymes) and output a plurality of reactions to produce the identifiers that constitute one or more identifier libraries. One or more identifiers may be produced in a given reaction. One or more identifier(s) may be produced in the plurality of reactions. The plurality of reactions may comprise greater than or equal to about 1, 2, 4, 6, 8, 10, 20, 30, 50, 75, 100, 150, 200, 300, 400, 500, 750, 1000, 10000, $1 \times 10^5$, $1 \times 10^6$, $1 \times 10^7$, $1 \times 10^8$, $1 \times 10^9$, or more reactions. The plurality of reactions may comprise less than or equal to about $1 \times 10^9$, $1 \times 10^8$, $1 \times 10^7$, $1 \times 10^6$, $1 \times 10^5$, 10000, 1000, 750, 500, 400, 300, 200, 150, 100, 75, 50, 30, 20, 10, 8, 6, 4, 2, or less reactions. One or more reactions may be conducted simultaneously or sequentially. The one or more, or plurality of, reactions may be combined to generate the identifier library. The assembly unit may selectively remove one or more of plurality of reactions that does not generate the selected identifiers. The assembly unit may comprise one or more sections, vessels, or partitions. The assembly unit may comprise a plurality of sections, vessels, or partitions. Each section vessel, or partition may generate, store, maintain, facilitate, or terminate one or more assembly reactions.

The assembly unit may comprise a reaction module. The reaction module may collect reagents, one or more nucleic acid sequences, one or more components, one or more templates, or any combination thereof. The reaction module may be configured to incubate or agitate an assembly reaction to generate one or more identifiers. The reaction module may additionally comprise a detection unit. The detection unit may monitor the assembly of the identifiers. The reaction module may comprise a plurality of partitions. The plurality of partitions may each comprise one or more assembly reactions. The plurality of partitions may be wells or droplets of a chemically modified surface.

Substrates, or inputs, may comprise one or more, and as many as M, layers. Each layer may comprise one or more components. The components in each layer may be distinct from the components in the other layers. Substrates may also include assembly templates, primers, probes, and any other elements for directing and facilitating identifier assembly reactions. Reagents may include enzymes, buffers, nucleic acid sequences, co-factors, or any combination thereof. Enzymes may be produced by overexpression of a corresponding recombinant gene in living cells. Reagents may be combined in an individual assembly reaction or may be combined as a master mix prior to being added to an assembly reaction.

The system may further comprise a storage unit (e.g., database). The assembly unit may output one or more identifier libraries. The one or more identifier libraries may be received by the storage unit. The storage unit may comprise one or more pools, vessels, or partitions. The storage unit may combine an individual identifier library with one or more additional identifier libraries to form one or more pools of identifier libraries. Each individual identifier library may comprise barcodes or tags to enable identifiers from each library to be identified and distinguished from one another. The storage unit may provide conditions for long term storage of the identifier libraries (e.g., conditions to reduce degradation of identifiers). The identifier libraries may be stored in a powder, liquid, or solid form. The database may provide Ultra-Violet light protection, reduced temperature (e.g., refrigeration or freezing), and protection from degrading chemicals and enzymes. Prior to being transferred to a database, the identifier libraries may be lyophilized or frozen. The identifier libraries may include ethylenediaminetetraacetic acid (EDTA), other metal chelating agents, or other reaction-blocking reagents to inactivate nucleases and/or a buffer to maintain the stability of the nucleic acid molecules.

The system may further comprise a selection unit. The selection unit may be configured to select one or more identifiers from an identifier library or from a group of identifier libraries. The assembly unit may set up all possible reactions to generate a combinatorial space and the selection unit may selectively remove reactions that do not produce the target identifiers and preserve the reactions that do produce the target identifiers. The selection unit may comprise an optical or mechanical ablation module to remove reactions, a dispenser to deliver degradation enzymes to non-targeted reactions, or a dispenser to deliver primers or affinity tagged probes to targeted reactions. The selection unit may facilitate assessing stored data. Accessing information stored in nucleic acid molecules (e.g., identifiers) may be performed by selectively removing a portion of an identifier library or an identifier library from a group or pool of identifier libraries that are combined. Accessing data may be performed by selectively capturing or amplifying identifiers corresponding to data to be accessed, and/or removing identifiers that do not correspond to the data to be accessed. Methods for selecting identifiers may include using polymerase chain reaction, affinity tagged probes, and degradation tagged probes. A pool of identifiers (e.g., identifier library) may comprise identifiers with a common sequence at each end, a variable sequence at each end, or one of a common sequence or a variable sequence at each end. The identifiers may contain the same common sequence at each end or different common sequences at each end. An identifier library may comprise common sequences that are distinct to that library enabling a single library to be selectively accessed from a pool or group of more than one identifier libraries. The common sequences or variable sequences may be primer binding sites. One or more primers may bind to the common regions on the identifiers. The identifiers with primers bound may be amplified by PCR. The amplified identifiers may significantly outnumber the non-amplified identifiers.

The common sequence of the identifiers may share complementarity with one or more probes. The one or more probes may bind or hybridize to the identifiers to be accessed. The probe may comprise an affinity tag. The affinity tags may bind to a bead, generating a complex comprising a bead, at least one probe, and at least one identifier. The beads may be magnetic and the selection unit may comprise one or more magnetic or electronic areas. The beads may collect and extract the identifiers to be accessed. Alternatively, or in addition to, the beads may collect the identifiers not accessed. The identifiers may be removed from the beads under denaturing conditions prior to reading. The affinity tag may bind to a column and the selection unit may comprise one or more affinity columns. The identifiers to be accessed may bind to the column of the identifiers to be accessed may flow through the column and identifiers not accessed may bind to the column. Accessing identifiers bound to a column may be unbound or denatured from the column prior to reading. Accessing the identifiers may comprise applying one or more probes to an identifier library simultaneously or applying one or more probes to an identifier library/group of identifier libraries sequentially. In an example, one or more identifier libraries are combined and each identifier library comprises one or more distinct common sequences. One set of probes may be applied to the libraries to extract a first subset of identifiers. Subsequently, a second set of probes may be applied to the libraries to extract a second subset of identifiers. This operation may be repeated until all identifiers are extracted.

The common sequence of the identifiers may share complementarity with one or more probes. The probes may bind to or hybridize with the common sequence of the identifiers. The probe may be a target for a degradation enzyme. In an example, one or more identifier libraries may be combined. A set of probes may hybridize with one of the identifier libraries. The set of probes may comprise RNA and the RNA may guide a Cas9 enzyme. A Cas9 enzyme may be introduced to the one or more identifier libraries. The identifiers hybridized with the probes may be degraded by the Cas9 enzyme. The identifiers to be accessed may not be degraded by the degradation enzyme. In another example, the identifiers may be single-stranded and the identifier library may be combined with a single-strand specific endonuclease(s) that selectively degrades identifiers that are not to be accessed. Identifiers to be accessed may be hybridized with a complementary set of identifiers to protect them from degradation by the single-strand specific endonuclease(s). The identifiers to be accessed may be separated from the degradation products by size selection, such as size selection chromatography (e.g., agarose gel electrophoresis). The selection unit may be capable of performing one or more size selection techniques. Alternatively, or in addition, identifiers that are not degraded may be selectively amplified (e.g., using PCR) such that the degradation products are not amplified. The non-degraded identifiers may be amplified using primers that hybridize to each end of the non-degraded identifiers and therefore not to each end of the degraded or cleaved identifiers.

The individual nucleic acid sequences (e.g., components and templates) that constitute identifiers or assist the construction of identifiers may be synthesized by the system or may be synthesized and amplified external to the system. The system may further comprise a nucleic acid synthesis module. The nucleic acid synthesis module may perform base-by-base construction of the components and templates. The nucleic acid sequences (e.g., components and templates) may be constructed using phosphoramidite chemistry. The components may initially be constructed using phosphoramidite chemistry and then PCR may be used to replicate the original phosphoramidite template. The components may initially be constructed using phosphoramidite chemistry and then copies of the template may be produced by cloning the components into one or more high copy vectors. The vectors may be transformed into living cells where the vectors, along with the embedded nucleic acid sequences, may be replicated during cell growth. The vectors may be isolated from the cell culture and the components may be isolated from the vectors using a restriction digest. Double-stranded nucleic acid sequences may be converted into single-stranded nucleic acid sequences by using affinity tagged probes that share complementarity with one of the two nucleic acid strands.

The system may use techniques to minimize the number of reactions used to generate an identifier library and, therefore, writing time. The one or more techniques may include heuristic techniques. A heuristic technique may minimize the set of compartmentalized sets of reactions used to construct a given set of identifiers from components. The heuristic technique may include on-set covering heuristics. The physical distance traveled by the writing apparatus may also be minimized to reduce write time. FIG. 8 illustrates an example method for minimizing writing time by minimal reaction set generation.

The system may transfer fluid (e.g., reagents, components, templates) using pressure, vacuum, or suction. The assembly unit may combine one or more nucleic acid sequences with one or more reagent mixtures. The assembly unit may use one or more of electrowetting, misting, printing, laser ablation, weaving or braiding of materials coated in nucleic acid sequences, slip technology, stamping, laser printing, or droplet microfluidics to combine substrates (e.g., enzymes, components, and templates) into reactions. The assembly unit may co-locate biomolecules to generate a plurality of co-located sets of biomolecules. The co-located sets of biomolecules may generate the identifiers. For example, by assembling a distinct component from each layer to a shared substrate, such as a bead, instead of concatenating the components to each other. Various techniques may be used to co-locate sets of biomolecules. As an example, instead of constructing an identifier by concatenating a set of distinct components to each other, an identifier may be constructed by associating the components to a shared substrate such as a bead. As another example, instead of constructing an identifier by concatenating a set of distinct components to each other, an identifier may be constructed by assembling the components each to a barcode sequence that identifies the association of the components.

Figure 11:
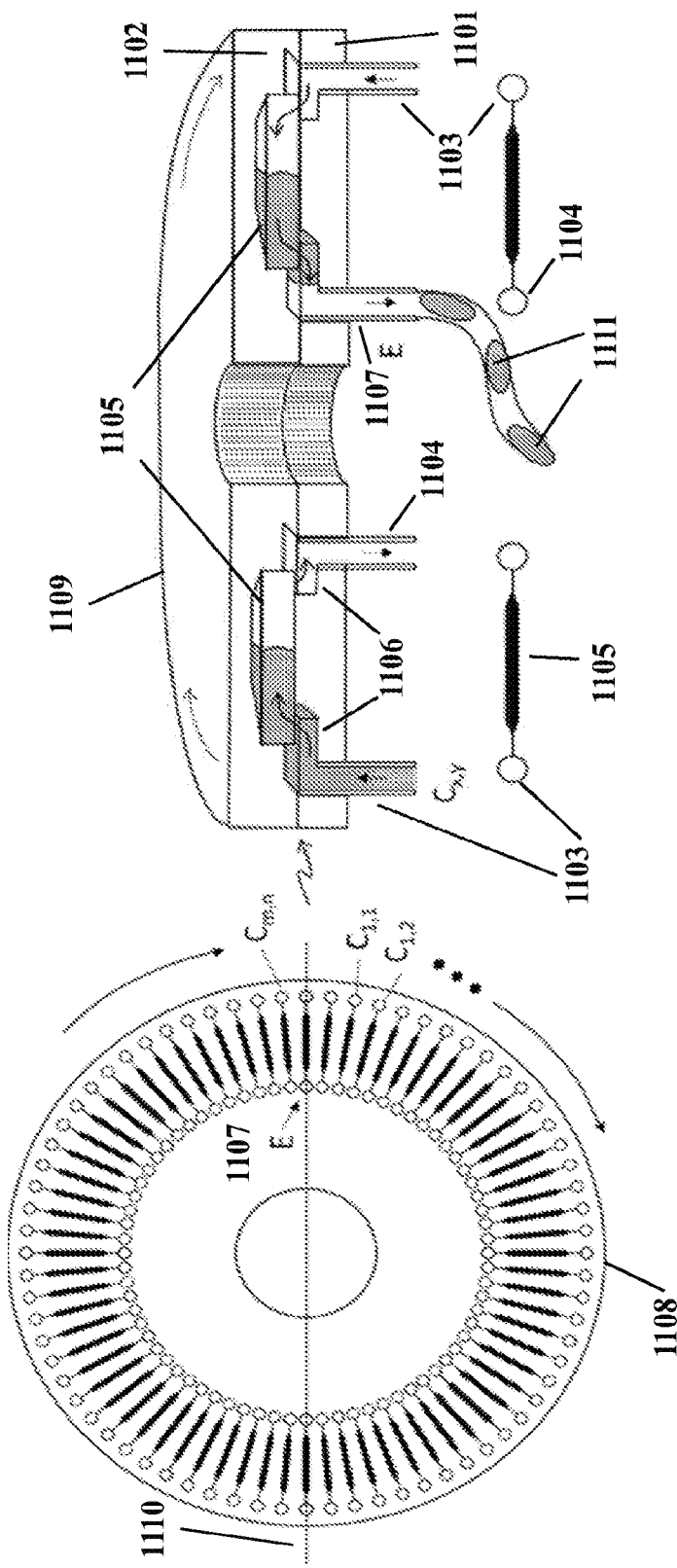
FIG. 11 shows an example component carousel.

A component carousel may be used to co-locate sets of biomolecules. FIG. 11 shows a top down view 1108 of an example component carousel and the cross-sectional view 1109 of a component carousel along the line 1110 of the top view 1108. In this example, the component carousel comprises a plurality of inlet ports and a plurality of outlet ports. The inlet ports may be on an outer circumference of the carousel and the outlet ports may be on an inner circumference of the carousel. Each inlet port may selectively introduce a single input (typically a component, but possibly also a nucleic acid, enzyme, or reaction mix) into a reaction chamber connected to an outlet port. After introducing one input the carousel may shift one position over to selectively introduce the adjacent input to the reaction chamber. This process may repeat until the selected number of inputs may be combined.

A component carousel may be comprised of two substrates 1101 and 1102 with flat surfaces configured to face each other. In the embodiment shown in FIG. 11, the two surfaces are configured to rotate with respect to one another. In some cases, it is advantageous to introduce an oil or another lubricant between the two surfaces to reduce the sliding friction. While any lubricating fluid can be used, a fluorinated oil may be used to minimize the movement of biological materials into the oil or between chambers. In this example, the inlet 1103 and outlet 1104 ports consist of through-holes arranged in pairs in one of the substrates 1101. The second substrate 1102 has one chamber 1105 for each pair of through-holes. When the surfaces of the two substrates are placed in contact facing each other the chamber 1105 in the second substrate 1102 aligns with a grove or channel 1106 in the first substrate to complete a flow path between the pairs of through-holes. The two substrates are designed to slide with respect to each other in such a way that sequentially each flow path is connected through every chamber as the two surfaces slide past each other through a complete rotation. In this way all inputs can be selectively added to each chamber. For example, in one embodiment there are 72 pairs of through-holes in the first substrate and 72 chambers in the second substrate. The system is configured such that a different component can be selectively introduced into the chamber every time the surfaces are indexed through five degrees. At the end of a complete rotation, an exit port 1107 allows for the reaction mix to be driven from the chamber as a bolus 1111. After purging a reaction from the chamber, it can be reused for a subsequent reaction. Typically, one path is used for removing the reaction bolus 1111 and the following flow path is used to clean the reaction chamber, introduction of the master mix into the reaction chamber can optionally have a separate flow path or the master-mix may be introduced along with each input. In this example, the remaining 70 flow paths allow for 70 unique inputs to be sequentially introduced into a given reaction chamber. If the inputs are components distributed in 22 layers of 3 components and one layer of 4 components, the combinatorial space of the product scheme is sufficient to generate $4*3^{22}=1.2\times10^{11}$ identifiers. With a slight increase in the number of flow paths to facilitate 96-components, it is possible to arrange 96 components into 32 layers with 3 components per layer to generate up to 1.8e15 unique identifiers. In some embodiments the chambers are filled with an oil or gas prior to introducing the first input. In some embodiments an oil or gas is used to drive the reaction from the reaction chamber after the last input and reaction master-mix have been introduced. There is no limitation on the number of chambers or inputs that can be introduced. In some embodies 10 or fewer chambers are used, in some embodiments 10 to 100 chambers are used, in other embodiments 100 to 1000 chambers are used. In other embodiments more than 1000 chambers are used. There is no limitation on the types of biological materials that can be introduced into the chambers. In some instances, the inputs can be amino acids or factors for peptide synthesis, in other cases the inputs can be reactants for synthesizing small molecules, in other cases, the inputs may comprise a cell, bacteria, virus, droplet or other particle, or a lysis buffer, or reagents for tagging, amplifying, binding, or identifying biological materials within the cell lysate or on the surface of a cell, bacteria, virus or other particle. In some instances, the chambers are indexed between pairs of ports at a rate of several times per hour or several times per minute. However, this indexing frequency can be of arbitrary timing and may be selected to be fast. In some cases, once per second or 10 times per second or 100 times per second or 1,000 times per second or 10,000 per second or more. External fluidic control may be used to selectively introduce inputs into the chambers on demand.

Figure 12:
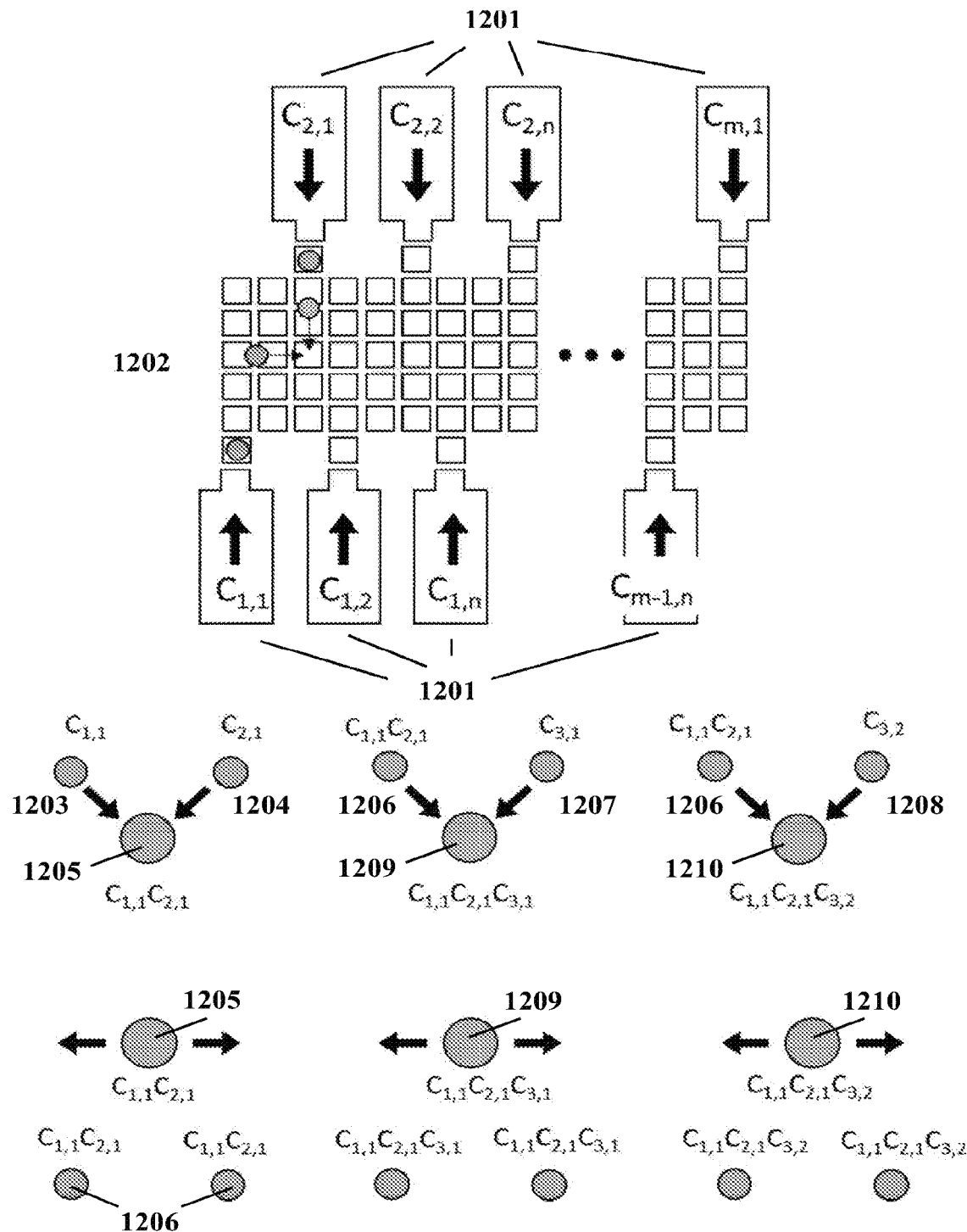
FIG. 12 schematically illustrates a method of using electrowetting for component operations.

Electrowetting may be used to co-locate sets of biomolecules. FIG. 12 illustrates a method of electrowetting for input operations. Inputs (e.g., nucleic acids, components, templates, enzymes, or reaction mix) may be introduced through separate ports 1201. Each port 1201 may introduce one input or a mixture of inputs. Droplets may be generated using electrowetting and combined to bring together the selected inputs for assembling identifiers. Droplets are made, combined, mixed and split by selectively applying voltage to electrode patches 1202. In some embodiments those electrode patches are arranged in square array. Patches are typically configured so as to be separated from the droplets by an insulating coating with a low electrical conductivity. The electrowetting device may be open on top or closed on top. The electrowetting chamber may contain an insulating fluid such as an oil. Any oil may be used such as silicon oils, mineral oil or hydrocarbon oils. In an example, fluorinated oils are used. Surfactants mixtures of other additives may be utilized to improve device performance by modifying the surface energy at either the droplet oil interface or at the interface with the chamber walls.

Electrowetting approaches can be utilized to make and manipulate small volumes of fluid ranging from sub-picoliter to nanoliters. For example, FIG. 12 illustrates an electrowetting device configured to selectively combine inputs in a programmable way. Systems are readily configured to simultaneously process 10s, 100s, 1000s, 10,000s, millions or more droplets simultaneously using electrowetting approaches. In some embodiments it can be advantageous to combine droplets and then split the combined droplet into two mixed droplets. In some cases, mixing can be enhanced by combing and splitting in roughly orthogonal directions. The split droplets can than each receive different subsequent inputs. The process may be repeated until all required inputs for identifier construction are introduced into the droplets. For example, a droplet 1203 containing component $C_{1,1}$ (component 1 of layer 1) and a droplet 1204 containing component $C_{2,1}$ (component 1 of layer 2) are combined into a mixed droplet 1205 $C_{1,1}C_{2,1}$ wherein the mixed droplet has both components. The mixed droplet can subsequently be split into two daughter droplets 1206 both having a similar mixed composition. Additional droplets having components from the third layer $C_{3,1}$ 1207 and $C_{3,2}$ 1208 can be introduced into the mixed droplets 1206 to form droplets 1209 and 1210 containing components from the first three layers. This process of combining, mixing and splitting of droplets can be iterated until the components used to construct the appropriate identifiers has completed. In some cases, a master mix for assembling or constructing identifiers may be introduced either with the nucleic acid inputs or in separate input droplets. For a product scheme, at least one component from each layer may be introduced into a droplet in order for a complete identifier to be assembled. In multiplex reactions, multiple components from one or more layers may be introduced into a given droplet. In embodiments utilizing droplet splitting, it may be advantageous to have components at different initial concentrations to facilitate a balanced concentration of each component. Due to the parallel nature in which droplets can be processed in different locations on the same electrode array it may be possible to process droplets at an arbitrarily high rate with thousand, millions or billions of droplet reaction conditions being setup per second.

Figure 13:
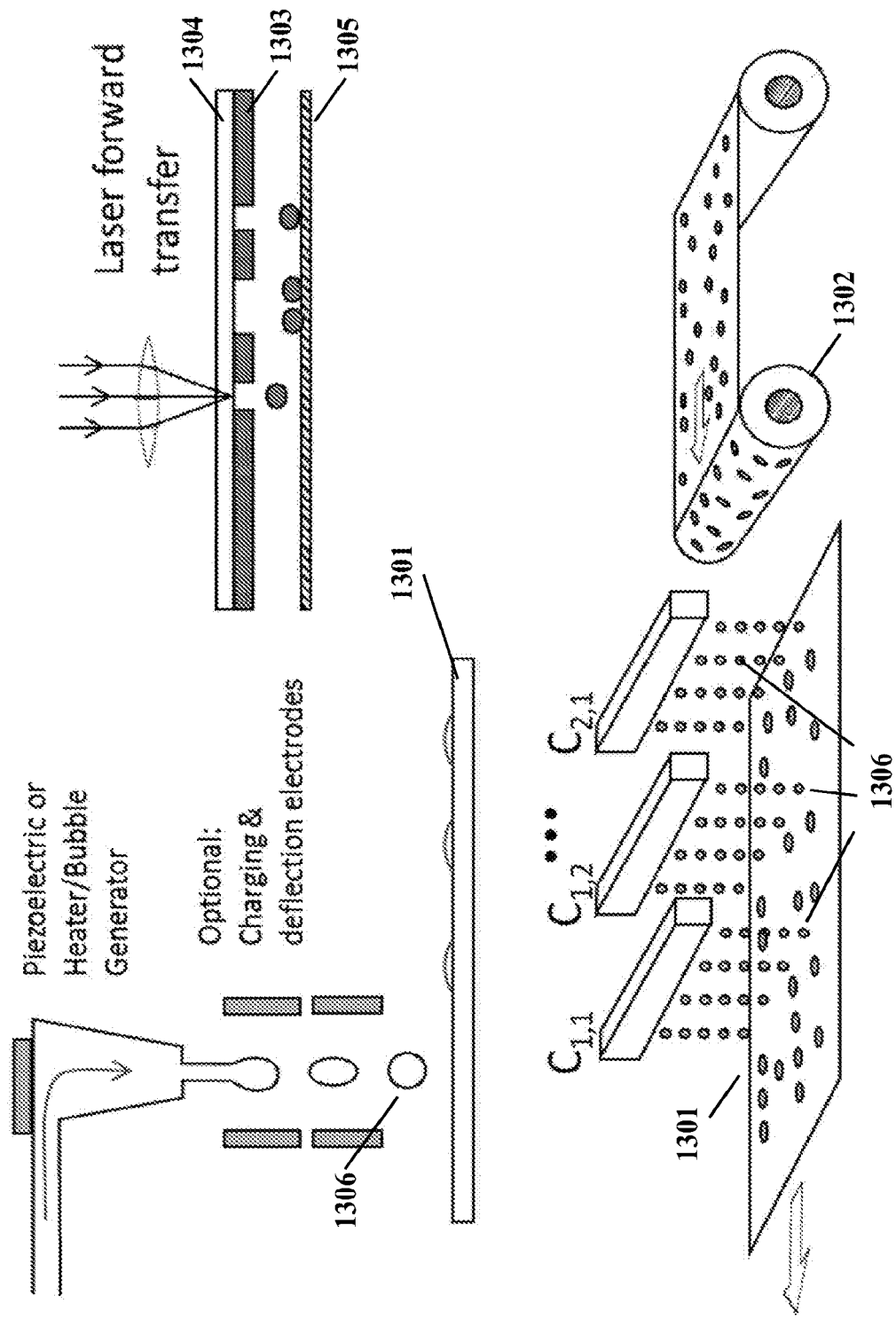
FIG. 13 shows example print-based methods for dispensing components.

Print based methods may be used to co-locate biomolecules. FIG. 13 shows example print-based methods for dispensing inputs. Inputs (e.g., nucleic acids, components, templates, enzymes, or reaction mix) may be brought together in stationary reaction regions by dispensing or printing directly in those regions. Reaction regions may be separate locations on a substrate 1301. Component inputs 1306 may be assembled into identifiers in the separate regions. The surface may be patterned with chemical modifications to create regions of varying hydrophobicity. The regions of varying hydrophobicity may be useful to inhibit the movement of inputs from one region to a neighboring region. Regions may have dimensions of greater than or equal to about 0.1 micrometers (µm), 0.5 µm, 1 µm, 2 µm, 4 µm, 6 µm, 8 µm, 10 µm, 20 µm, 40 µm, 60 µm, 80 µm, 100 µm, or more. Regions may have dimensions less than or equal to about 100 µm, 80 µm, 60 µm, 40 µm, 20 µm, 10 µm, 8 µm, 6 µm, 4 µm, 2 µm, 1 µm, 0.5 µm, 0.1 µm, or less. Reaction regions may be separated by physical barriers such as walls. Walls can be lithographically formed on an otherwise flat surface to make micro-wells. Alternatively, or in addition to, micro-wells can be molded or embossed in a plastic substrate. Micro-well volumes may be greater than or equal to about 0.1 picoliter (pL), 1 pL, 10 pL, 100 pL, 1 nanoliter (nL), 10 nL, or greater. Micro-well volumes may be less than or equal to about 10 nL, 1 nL, 100 pL, 10 pL, 1 pL, 0.1 pL, or less. Substrates may include glass, paper, or plastic films. The substrate may optionally be patterned using one or more methods, such as hydrophobicity, embossed wells, etched wells, molded features, deposited features. In a reel-to-reel system 1302 a roller may be used to directly pattern indentations in the substrate prior to dispensing. The substrate may translate under a stationary printhead or optionally the print head may translate over the surface of the substrate. Dispensing may utilize a wide variety of commercially available printing approaches. A printhead may comprise greater than or equal to 1, 10, 100, 1,000, 10,000, or more nozzles. Each nozzle of the printhead may dispense the same input or one or more nozzles may dispense distinct inputs. In some embodiments a sufficient number of printheads are utilized such that a given nozzle may dispense a single input. For example, if each printhead dispenses 4 inputs, a collection of 50 printheads can dispense 200 inputs. Such an arrangement with the printheads aligned to dispense onto a swath may optionally be combined with reel-to-reel operation of a substrate passing under all printheads to dispense all inputs to all reaction regions. Each nozzle in the printhead may dispense at a rate of 10, 100, 1,000, 20,000, 50,000, or 100,000 or more dispenses per second. Each nozzle may be configured to operate in parallel such that a printhead with 1000 nozzles operating at 50,000 dispenses per second can dispense up to 50 million times per second. Print drivers may allow for higher and lower frequencies and drop-on-demand operation and any of these can be utilized for dispensing inputs. These systems include, but are not limited, ink-jet, bubble-jet, and piezo-electric arrays. In some cases, electrostatic charge and electric fields are used to direct and control the placement of the droplets. In other cases, electrostatically neutral droplets are dispensed.

Similar in operation to a printhead, laser forward transfer is an optical technique to selectively transfer material comprising an input 1303 from one substrate 1304 to a receiving surface 1305. Precise positioning of a laser pulse selectively controls the transfer of material. By controlling the laser focus, pulse width, power, and location the amount of material transferred can be controlled to pattern the transfer of a given input onto a substrate. Sequential transfer of each input provides a robust mechanism and time efficient method to prepare the collection of reactions. In some embodiments an optically detectable marker such as a fluorescent or absorbent dye may be introduced into the input fluid to enhance imaging based inspection to confirm the inputs are distributed into reactions as intended.

Encoding and writing a $1.0 \times 10^{12}$ bit string by (1) re-coding the string into a uniform weight form where every contiguous (i.e., adjacent and disjoint) stretch of 250 bits has exactly 75 bit-values of '1', (2) using an example encoding method to encode the re-coded the bit stream into an identifier library (excluding identifiers from the library that correspond to bit-values of '0'), and (3) using the product scheme to construct the identifiers with components divided into 8 layers. In this example protocol, a codeword comprising a subset of exactly 75 identifiers from each sequential set of 250 possible identifiers may be used to encode sequential words of length 216 bits from the original information string. When using this 250-choose-75 uniform encoding approach to represent 216 bit words in a one terabit ($1 \times 10^{12}$ bit) string, a combinatorial space of at least $(250/216) \times 1.0 \times 10^{12} = 1.15 \times 10^{12}$ distinct identifiers may be used. In this example, we use 7 layers with 20 components in each layer and an 8th layer with 1000 components. The available identifiers in this example are then $1000 \times 20^7 = 1.28 \times 10^{12}$, which exceeds the minimum required number of $1.15 \times 10^{12}$. Hence it may be sufficient to uniquely represent $1.0 \times 10^{12}$ bits. Multiplexed assembly reactions can be configured by dispensing 1 component from each of the first 7 layers and $75 \times 4 = 300$ components from the 8th layer into each reaction to assemble components representing 4 codewords a single multiplex reaction volume. The 7 components from the first seven layers assemble with the 300 components from the 8th layer to generate 300 unique identifiers representing a unique $4 \times 216 = 864$ bit portion of the original $1.0 \times 10^{12}$ bit stream. An identifier library representing the entire $1.0 \times 10^{12}$ bit string can be assembled using $1.0 \times 10^{12}/864 = 1.16 \times 10^9$ reactions where each reaction has one component from each of the first seven layers and 300 components from the 8th layer (or 307 total components between all layers). Using 100 micron separation between reactions, a region of roughly 12.8 meters squared ($m^2$) may be covered with reactions in this example. Using 160 nozzles per component on a single printhead operating at 5000 dispenses per second, all $1.16 \times 10^9$ reactions can be addressed in less than 30 minutes. An assembly with 10 printheads dispensing 4 components each using 160 nozzles per component and operating at 5000 dispenses per second can distribute all 1140 components to all $1.16 \times 10^9$ reactions in roughly 12.6 hours of continuous dispense operation.

Figure 14:
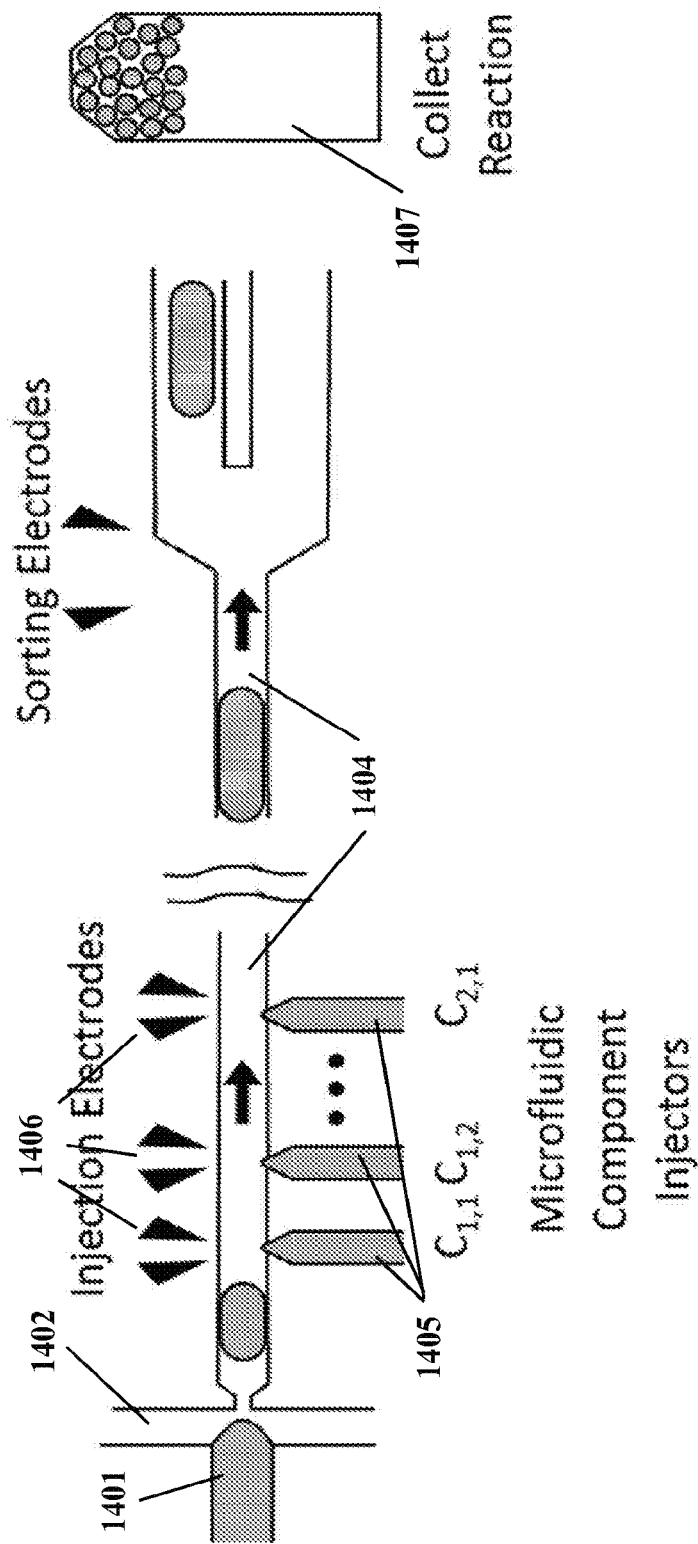
FIG. 14 shows an example of microfluidic injection of components.

Microfluidic injection may be used to co-locate biomolecules. FIG. 14 shows an example of microfluidic injection of inputs. Microfluidic devices may be constructed by any method, such as injection molding or embossing plastic substrates or etching glass channels or crossing a polymer. Fluids are introduced into the microfluidic devices through ports and can be driven by any method such as electroosmotic flow, external pressure or vacuum, or a positive displacement pump. In one embodiment, a stream of master mix 1401 is introduce into a stream of carrier oil 1402 and droplets of master-mix 1403 form the stream of oils. In some embodiments the master mix droplets may be 1 nL or larger, in other embodiments they are less than 100 pL or less than 50 pL or less than 10 pL or less than 5 pL or less than 1 pL in volume. The master-mix droplets may contact the channel walls or a layer of carrier oil may separate the droplets from the channel walls. The carrier oil may be any oil such as a hydrocarbon, fluorocarbon, silicon, or mineral oil or any combination of oil. In an example, the oil is a fluorocarbon oil. In some embodiments the oil may further comprise a surfactant or other additives. The master-mix may comprise aqueous fluids. Inputs are introduced into the microfluidic device through ports and a plurality of input streams 1405 that intersect the main channel 1404. Inputs (e.g., nucleic acids such a components or templates, enzymes, or reagent) may be selectively added to droplets as they pass by one or more injection orifices. Injection may be controlled through the selective application of an electric field through the application of a voltage to electrodes 1406 located near the main channel. The electrodes may be separated from the channel by an insulating layer. In one embodiment, all possible distinct identifier-producing reaction droplets may be generated and the targeted subpopulation of the droplets may be collected using a sorting bifurcation in the channel. Sorting may be achieved by any method, including but not limited to, using an electric field gradient, a laser pulse, a gas bubble, a piezoelectric actuator, an external valve, acoustic waves, or any other soring mechanism. In another embodiment, droplets containing the target identifier-producing reactions are generated. Reactions may go to completion either on or off of the microfluidic device where they are made. The droplet may be collected in a reaction reservoir 1407 either on or off of the microfluidic device.

Each identifier may be constructed with a product scheme by assembling components, at least one component from each layer introduced into the same droplet. Multiple identifiers may be assembled in a droplet by introducing at least two components from at least one layer. Each picoinjector comprises a component stream 1405 and a method of applying an external electric field 1406. Components are assembled enzymatically into identifiers. In some embodiments the component fluids 1405 further comprise an enzyme or a master mix. By way of example, a microfluidic device comprising ten sets of ten pico-injectors configured such that any combination of components from 10 layers of 10 components each can be introduced into a flowing droplet using a set of 100 pico-injectors. This example system may be capable of generating $10^{10}$ unique identifiers constructed with the product scheme. One can readily generalize to M layers with N pico-injectors (e.g., component inputs) in each layer such that N×M pico-injectors can construct $N^M$ identifiers. More generally, if one layer is designated as a multiplex layer with xN pico-injectors then the construction of xN identifiers can be multiplexed in each droplet. The advantage of having one layer with more components than other layers is that the layer can be used as a multiplex layer for assembling multiple identifiers in the same droplet, thus reducing the total number of droplets required write information. Each droplet receives one component from each layer except the multiplex layer from which it may receive up to all components; xN identifiers are constructed in each droplet.

There may be flexibility in how components can be divided into layers for assembling identifiers with the product scheme. For example, the inputs in a given set of 200 pico-injectors may be divided into 11 layers of components, 10 layers with 10 components each (also pico-injectors for dispensing them) and a multiplex layer with 100 components. The combinatorial space of identifiers may then have a size of $10^{10} \times 100 = 10^{12}$. Alternatively, one may use the same 200 pico-injectors and divide them into 40 layers of 4 components and a multiplex layer of 40 components. The combinatorial space size may then be $4^{40} \times 40 = 4.8 \times 10^{25}$. More layers may typically result in longer DNA identifiers.

In an example droplet microfluidic system, identifiers are assembled from 12 layers of 16 components with the product scheme. In this example, the microfluidic device is configured to have 16 pico-injectors for each layer (16× 12=192 pico-injectors). It may then be possible to assemble $16^{12} = 2.8 \times 10^{24}$ unique identifiers. An alternate organization of 11 layers of 10 and one layer with 100 (11×10+100=210 pico-injectors) creates a combinatorial space of $10^{11} \times 100 = 10^{13}$ unique identifiers. Using a uniform weight encoding with codewords comprising a subset of 18 identifiers from every block of 100 identifiers, one may encode words of length 64 bits from the original, compressed bit stream. To represent an original 1.0e12 bit string, $1.56 \times 10^{10}$ droplets can be used. At a rate of 180,845 droplets/second or 1,809 drops/s on 100 parallel devices a 1.0e12 bit string can be written into DNA in 24 hours. With an initial droplet volume of 100 pL and the addition of 10 pL at each pico-injector that is used, 100 pL+100 pL (first 10 layers)+180 pL (multiplex layer)=380 pL per droplet. $380 \times 10^{-12} \times 1.5 \times 10^{10}$ droplets=5.7 L of total droplet volume used. After enzymatic assembly of identifiers in the droplets, then the contents of each droplet can be combined and concentrated or lyophilized in preparation for storage.

Figure 15:
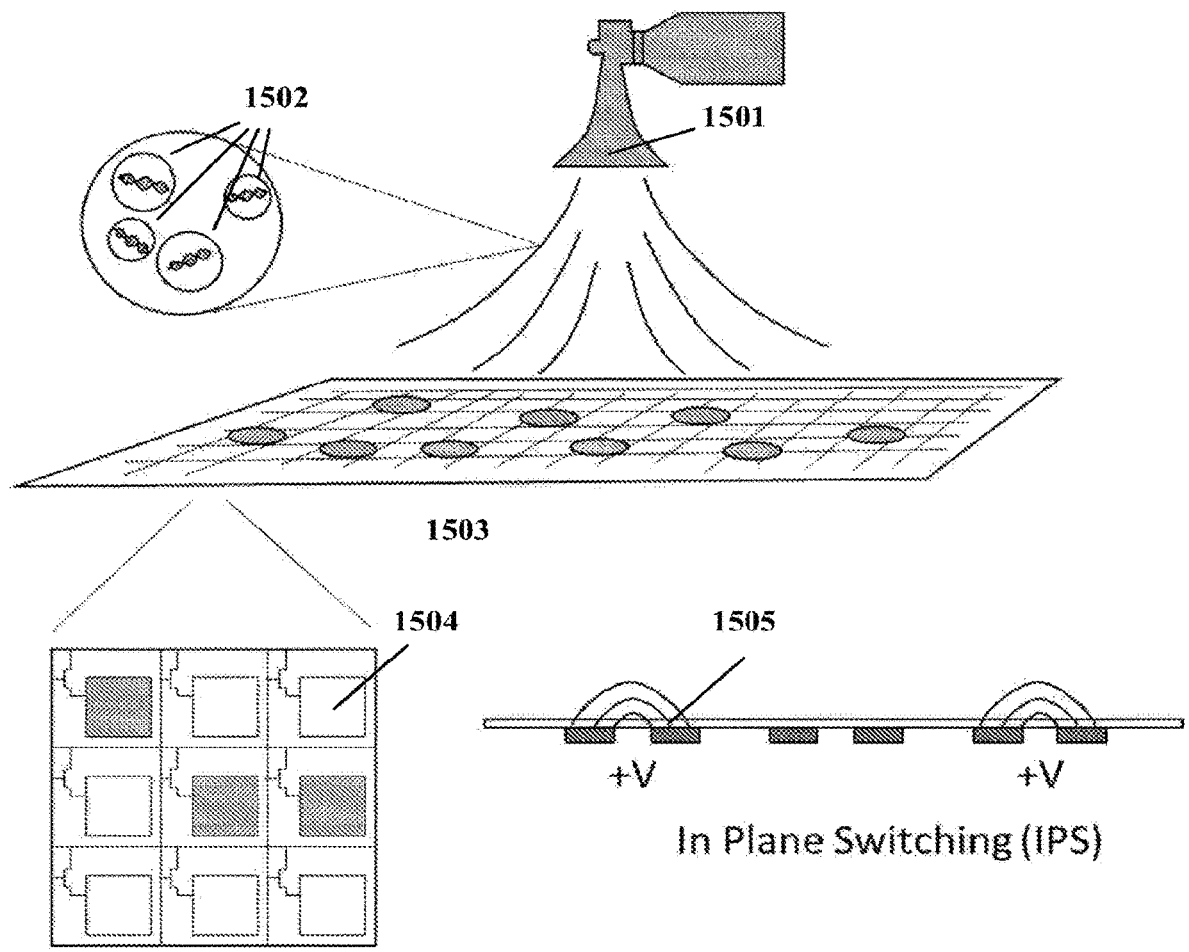
FIG. 15 shows and example of selective condensation of a component mist.

Selective condensation of a component mist may be used to co-locate biomolecules. FIG. 15 shows and example of selective condensation of a component mist for co-location of biomolecules. A mist nozzle 1501 may generate a mist or cloud of micron or sub-micron sized droplets 1502. The droplets may comprise one or more inputs (e.g., nucleic acid sequences such as components or templates, enzymes, or reagents). A mist cloud may be generated using vibrating membranes, electrospray, nebulizer, or any other method. The mist may direct droplets to a thin film transistor array 1503. The thin film transistor array may utilize individual electrodes 1504 to condense the mist or electrode pairs 1505 such as in-plane-switching configuration to selectively condense the mist droplets in specific regions of the transistor array. Inputs may be introduced onto the array 1503 one at a time or in groups of multiple inputs. The array may be dried between sequential introduction of inputs. After inputs are directed onto the array, a master mix may be introduced onto every reaction spot in the array identifiers may be constructed.

Other methods may be used to generate select libraries of identifiers such as slip-technology, microfluidic devices with elastomeric valves, and contact stamping. Slip-technology may comprise parallel input streams for parallel introduction of components into a plurality of chambers or partitions. The chambers may slide to allow access to the different compartments. In an example, components may be introduced into chambers through elastomeric valves. In another example, microfluidic channels may be places along a perimeter of tandemly places barrels such that channels of each barrel may be used to add components of one layer. The barrels may be rotated relative to each other by one channel diameter increments.

Figure 16:
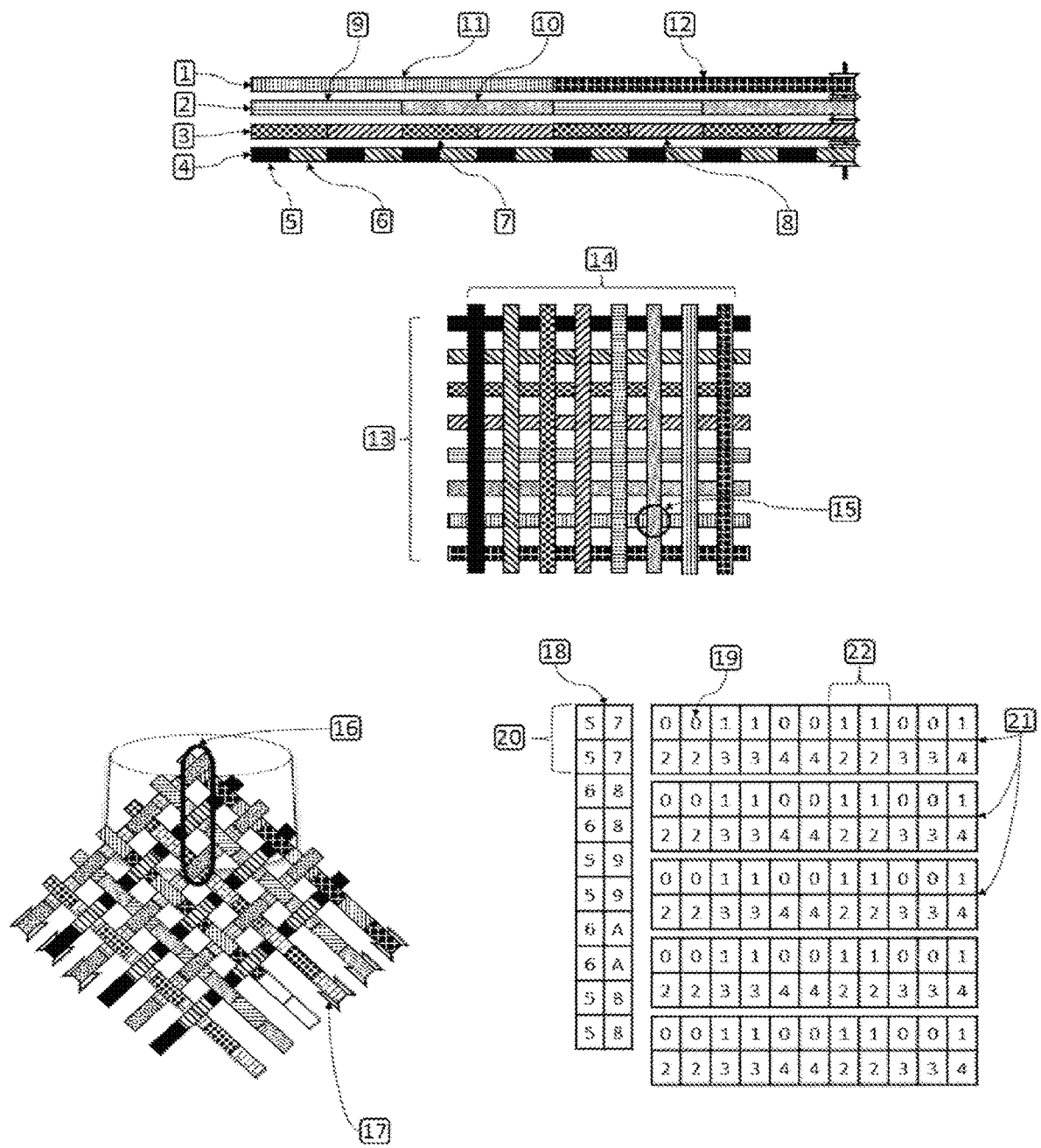
FIG. 16 schematically illustrates an example method of generating identifiers by weaving or braiding.

Various methods may be used to generate all possible identifiers from a combinatorial space. FIG. 16 schematically illustrates an example method of generating identifiers by weaving or braiding. Flexible materials may be coated in specific regions with specific components. The materials may be plastics, metals, threads, or natural materials. The flexible materials may be woven, braided, or pinched, or intertwined together to collocate components to be assembled. Segments of components may come together at the braid or weave junctions and may be separated into reaction volumes. After all identifiers have been constructed, any subset of identifiers may be deleted, including the subset that is inconsistent with a bitstream to be encoded. The family of methods where information may be encoded by deleting identifiers from a set of constructed identifiers or established identifier-producing reactions or by deleting collocated components to be assembled into an identifier is called the family of Subtractive writing methods. In one embodiment, the components may be located on threads or films. Items 1601-1604 depict an example in which four threads or films are marked in a specific pattern of components. For example, the length of the thread or film labeled 1601, is divided into two regions: region 0 is loaded with component 0 from layer 0 as shown by label 1611 and region 1 is loaded with component 1 from layer 0 as shown by label 1612. The length of the film or thread or fiber labeled 1602 is similarly divided into four regions: region 0 is loaded with component 0 (labeled 1609) of layer 1, region 1 with component 1 (labeled 1610) of layer 1, region 2 with component 0 of layer 1, and region 3 with component 1 of layer 1. In general, the film or thread or fiber corresponding to the i-th layer containing Ni components is divided into Ni-1*Ni regions, where each region is loaded with one of Ni components in the i-th layer, cycling in order through the list of Ni components repeatedly. This method of organizing regions of components on a substrate and loading them with components is called Combinatorial Marking. Other patterns, orders, and schemes may also be used for organizing components onto films and threads. In one embodiment, each thread or film or fiber may be loaded with a single component. A set of such single-component threads or fibers or films may be woven into a grid as shown in 1613 and 1614. In this example, each point of intersection between a horizontal and a vertical thread collocates two components, as depicted in 1615. In another embodiment, many threads may be caused to intersect at a single location, thus collocating a plurality of components. These intersection points may be used to construct identifiers, or the set of components so collocated may be extracted from these sites to assemble identifiers in another location. In one embodiment, each thread may have a specific pattern of regions and components as described above. These threads may be braided together to form a network as depicted in 1617. Regions of this braided network may collocate all the components used to construct an identifier, as depicted in 1616. These regions of the braided network may be used as reaction sites or the set of components so collocated at these regions may be extracted from these sites and used to assemble identifiers in another location. In another embodiment, a Product Scheme may be set up in which the number of components in each layer Ni are relatively prime to the number of components in all other layers. That is, for any pair Ni and Nj denoting the number of components in layers i and j where i is not equal to j, neither Ni divides Nj nor vice versa. An example is shown in 1618, where two threads or films or fibers are shown with thread 0 containing two components labeled 5 and 6 and thread 1 containing five components labeled 7, 8, 9, A, and B. The number of components in these layers, two and five, are relatively prime because 2 does not divide 5 and vice versa. The components are loaded onto the thread and repeated in a cyclical order. Thus, thread 0 has a repeating sequence of two components 5, 6, 5, 6, and so on as shown, and thread 1 has a repeating sequence of five components 7, 8, 9, A, B, 7, 8, 9, A, B, and so on as shown. In one embodiment, these threads may be pinched or twined or collocated together in such a way that each region loaded with a component on one thread may be aligned with the corresponding region loaded with another component on another thread. Because the number of components on each thread are relatively prime, all possible combinations of components are generated at the pinched or twined sites. The components so collocated at these sites may be used as reaction sites to construct identifiers from these components or used to extract the components so collocated for constructing identifiers in another location. In another embodiment, a similar scheme with number of components that are relatively prime may be used to generate a braided network of threads. The horizontal braiding threads are shown in 1621. The horizontal threads may be repeated as many times as the product of the number of components in the vertical threads.

Figure 17:
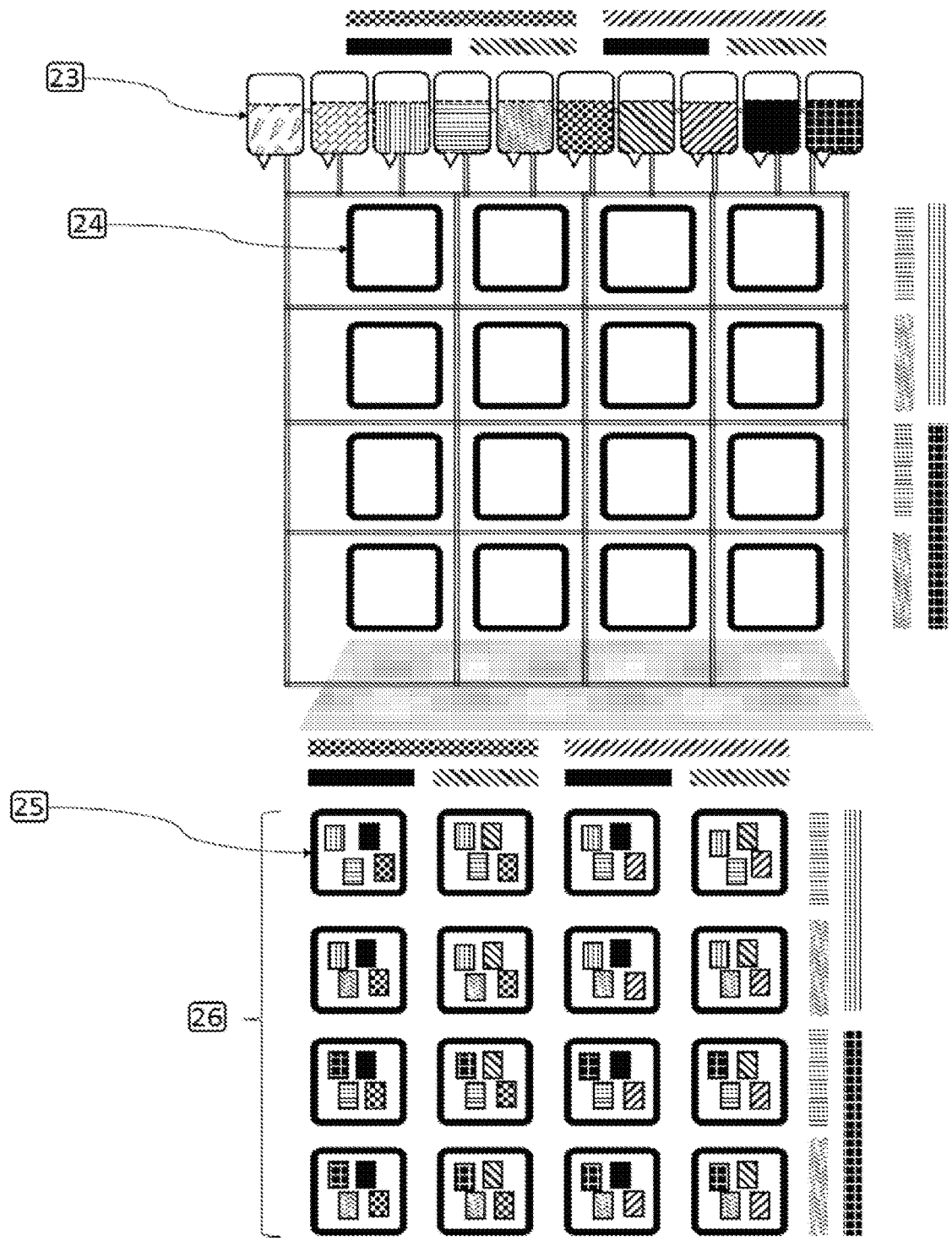
FIG. 17 schematically illustrates an example method for generating identifiers from a set of components.

FIG. 17 schematically illustrates an alternate method for generating identifiers from a set of components. The components are initially stored in separate reservoirs shown in 1723. The reservoirs may also store assembly reagents and other instruments. The components may be collocated in a set of reaction compartments, an example of which is shown in 1724. Using transport schemes such as printing or fluidic manipulation, each combination of components is collocated in an individual compartment, as shown in 1726. These compartments may now be used as sites for assembling the identifier using a plurality of biochemical processes.

Figure 18:
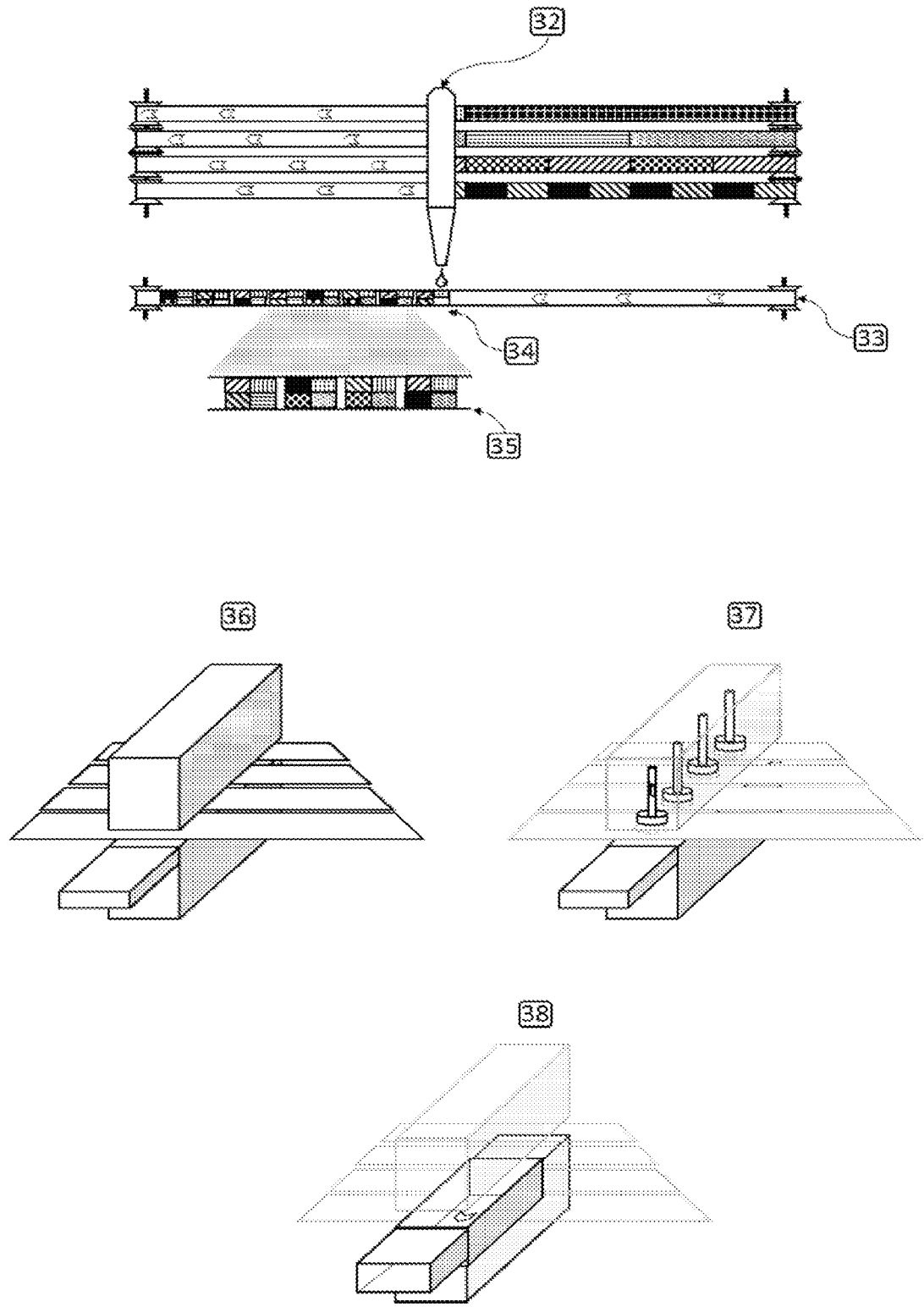
FIG. 18 schematically illustrates an example method for generating identifiers from separate films or threads.

FIG. 18 schematically illustrates an example method for generating identifiers from separate films or threads. 1832 shows a device, called a Collocator, that takes as input a rolling set of threads or films or fibers or substrates, each of which may be marked using the combinatorial marking scheme or some other marking scheme, and collects the components in each corresponding region on each individual thread or film or substrate. The collected components are collocated on an output film or thread or fiber shown in 1833. As each region on each thread or fiber passes through the Collocator, a new combination of components may be generated in a new region on the output film or thread, as depicted by 1834. Item 1835 shows a schematic of the collocated components which may be used as reaction sites to assemble identifiers. Item 1836 shows a closer view of one embodiment of the Collocator. Item 1837 shows one embodiment of the method of collecting the components. In this example, the Collocator punches holes through the passing fibers or threads or films and collects the punched-out pieces or fragments and outputs them to the output substrate. In another embodiment, the Collocator may scrape or aspirate or use other mechanical or electrical or optical or magnetic or braiding or weaving or pinching or stamping mechanisms to collocate all components from all the films or threads to the output film or thread or substrate.

A Subtractive writing method may be one in which a given digital message is encoded by deleting identifiers from a previously constructed identifier library or established library of identifier-producing reactions or by deleting collocated components prepared to be assembled into an identifier. In one embodiment, this library comprises all possible identifiers in a combinatorial space. Subtractive methods may be advantageous because they may remove the complexity of constructing a specific given set of identifiers on demand. Rather, the construction of identifiers may be independent of the specific digital message to be encoded and may be performed prior to any encoding request. Additionally, the process of encoding may require a simpler deletion operation at the point of writing, rather than biochemical assembly or construction of identifiers. In one embodiment, subtractive writing methods require methods for generating all possible identifiers. In one embodiment, when encoding is used with the product scheme, all possible identifiers may be generated by pre-loading a simple sequence of components for each layer, and then combining the pre-loaded streams of components. The pre-loaded sequence of components may be such that all possible component combinations are generated when the component streams are combined. This may be achieved using printing, threading, braiding, weaving, twining, pinching, stamping and other methods.

Figure 19:
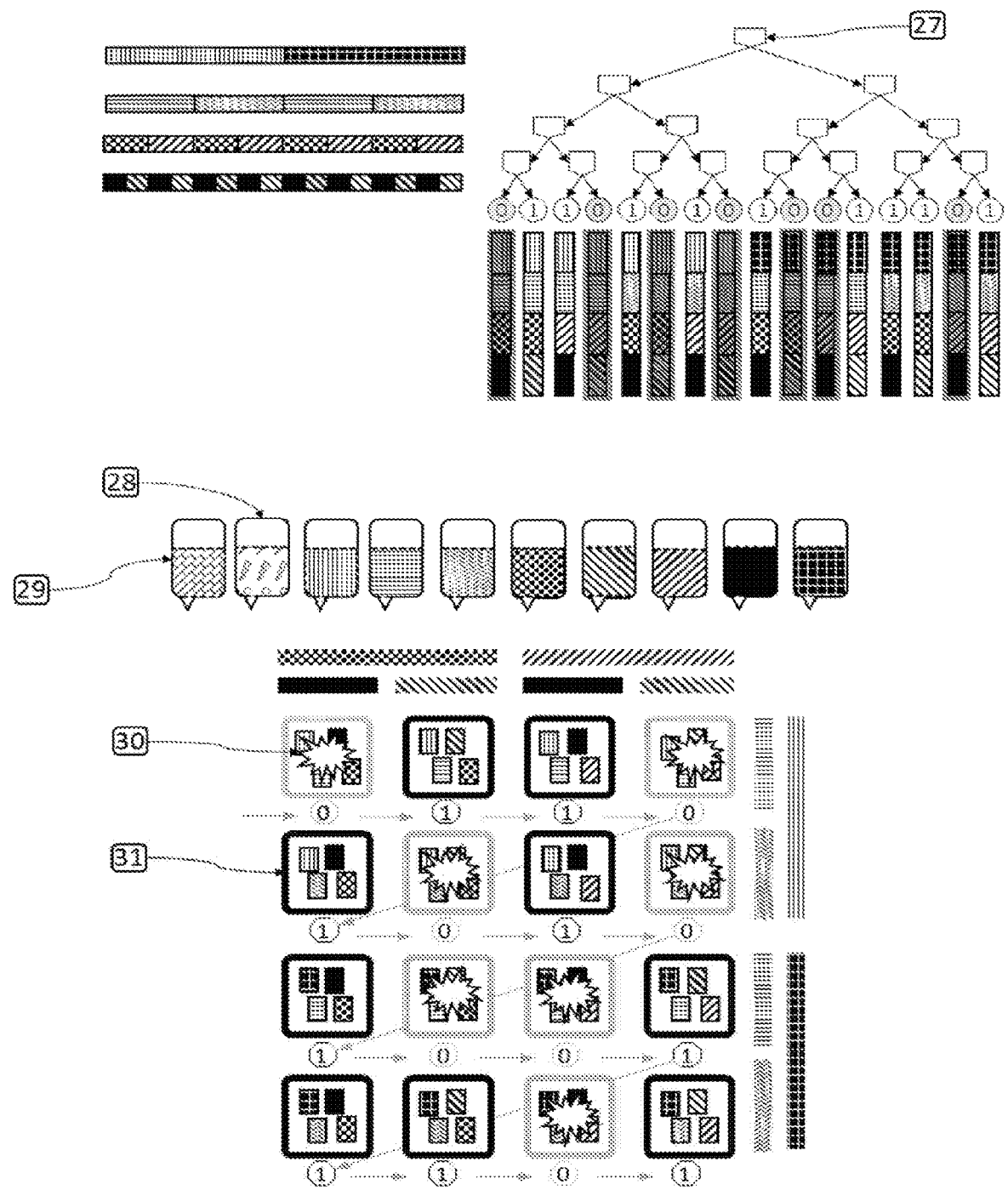
FIG. 19 schematically illustrates an example method for using subtraction to write information.

FIG. 19 illustrates an example method for using subtraction to write information. Subtraction-targeted identifiers may be removed enzymatically (e.g., using a CRISPR/Cas system) or by cleaving, optical, thermal, electronical, static or electric discharge or other charged particle beam, sorting, liquid jet, acoustic, mechanical scrape, or hole punch methods. In certain embodiments where components are collocated to form identifiers but not yet reacted, the components in each location may be assembled after the unwanted identifier-producing reaction setups are subtracted. Item 1927 shows the tree diagram for a given bitstream to be encoded using a Product scheme comprising four binary layers. In this example, the combinatorial space comprises 16 distinct identifiers. All 16 identifiers may be first collocated into individual compartments as shown in 1925. Then, these identifiers may be mapped to individual symbols in the information to be encoded, bit values in this example, as per the considerations outlined in FIG. 9. Once the correspondence between the bits and the identifiers is fixed, each compartment containing a set of components used to build an identifier may be mapped to a bit value in the bitstream. For each compartment mapped to a bit whose value is "0", the components in that compartment may be destroyed or deleted or otherwise manipulated such that no identifier is assembled in that compartment (item 1930). For each compartment mapped to a bit with bit-value "1", the components in that compartment are supplied with all the reagents used to assemble the identifier, and are not deleted or destroyed (item 1931). In another embodiment, all identifiers are assembled and the ones corresponding to bit values of "0" are deleted or destroyed after assembly. Finally, all surviving identifiers are pooled together to encode and store the given bitstream in a compact format.

The system may comprise a unit for reading the generated identifier libraries. In an example, decoding nucleic acid encoded data may be achieved by base-by-base sequencing of the nucleic acid strands, such as Illumina® Sequencing, or by utilizing a sequencing technique that indicates the presence or absence of specific nucleic acid sequences, such as fragmentation analysis by capillary electrophoresis. The sequencing may employ the use of reversible terminators. The sequencing may employ the use of natural or non-natural (e.g., engineered) nucleotides or nucleotide analogs. Alternatively or in addition, decoding nucleic acid sequences may be performed using a variety of analytical techniques, including but not limited to, any methods that generate optical, electrochemical, or chemical signals. A variety of sequencing approaches may be used including, but not limited to, polymerase chain reaction (PCR), digital PCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing.

Various read-out methods can be used to pull information from the encoded nucleic acid. In an example, microarray (or any sort of fluorescent hybridization), digital PCR, quantitative PCR (qPCR), and various sequencing platforms can be further used to read out the encoded sequences and by extension digitally encoded data. Subsets of data (e.g., data belonging to a particular barcode) can be accessed from a pool by PCR with one primer that binds to a 5' barcode in the forward direction and one primer that binds a common 3' sequence in the reverse direction.

The accessed data may be read in the same device or the accessed data may be transferred to another device. The reading device may comprise a detection unit to detect and identify the identifiers. The detection unit may be part of a sequencer, hybridization array, or other unit for identifying the presence or absence of an identifier. A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence incorporated within the nucleic acid molecule. Alternatively, the sequencing platform may be a system such as Illumina® Sequencing or fragmentation analysis by capillary electrophoresis. Alternatively or in addition to, decoding nucleic acid sequences may be performed using a variety of analytical techniques implemented by the device, including but not limited to, any methods that generate optical, electrochemical, or chemical signals.

Figure 20:
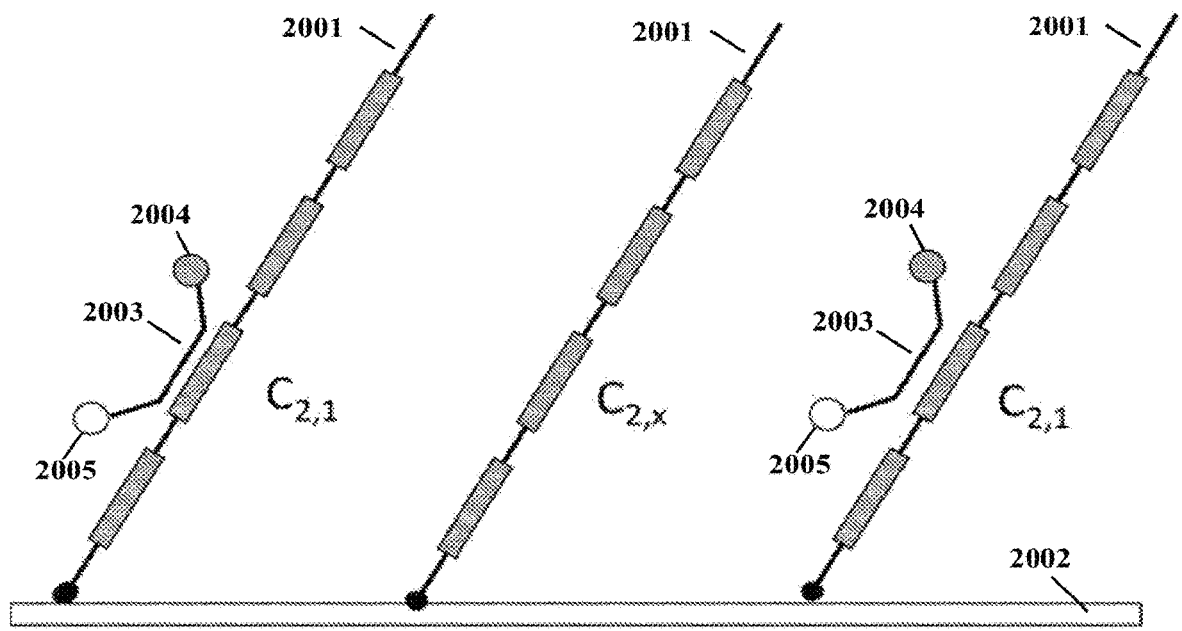
FIG. 20 schematically illustrates an example method of reading by hybridization.

Identifying identifiers in an identifier library may be performed using any identification or sequencing method. FIG. 20 illustrates an example method of reading encoded information by hybridization. A reading unit may comprise one or more hybridization arrays. A hybridization array may comprise the identifiers 2001 bound to a surface or a support 2002. The identifiers may be spatially oriented to enable single molecule resolution or resolution of a group of molecules using optical detection. Probe sequences 2003 that share complementarity with one or more components of the identifiers may be introduced to the array. The probe sequences may comprise one or more fluorophores 2004. In an example, a probe comprises a fluorophore and a quencher 2005. The quencher may be another dye or fluorophore or a quenchbody. Hybridization of the probe to an identifier may separate the fluorophore and the quencher to create a detectable signal. In other embodiments, the probe comprises a string of fluorophores that can be detected as an optical signature indicative of a specific probe or a specific set of probes. Individual components may be detected by optical imaging of the area or scanning of an area such as with confocal techniques. Sequential introduction of probes, imaging and removing of the probes may be used to identify some or all of the components on a given identifier. There may be no limit on the number of components that can be identified at once. Probes to different components may have different optical signatures or they may have the same optical signature.

Figure 21:
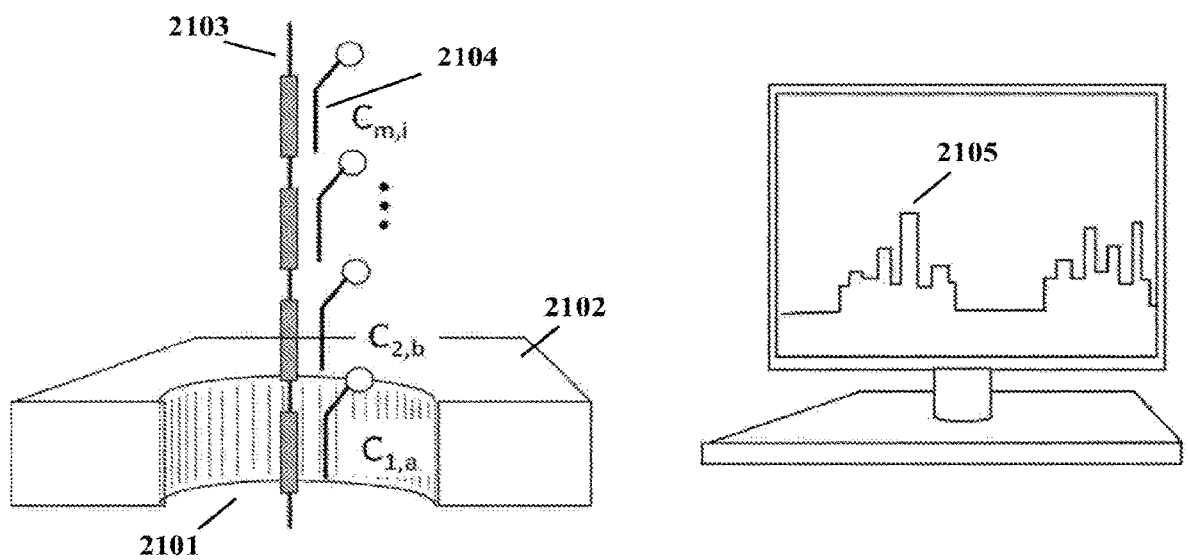
FIG. 21 schematically illustrates an example method of reading by Nanopore sequencing.

Another method for detecting identifier sequences may include Nanopore sequencing. FIG. 21 illustrates an example method of reading by Nanopore sequencing. Molecules may have a unique impedance signature when traveling through pores or channels, where a voltage is applied across the pores or channels. Several existing nucleic acid sequencing platforms use this property to determine the sequence of base pairs in nucleic acid molecules. These platforms have the advantage of being able to sequence longer molecules of nucleic acid and to detect the presence or absence of non-natural nucleotides as well as chemical moieties that can be used to decorate both natural and non-natural nucleotides. In an example, an identifier sequence 2103 is combined with probes 2104 that hybridize to the components of the identifier sequence. The probes may comprise molecules that generate unique impedance signals while traveling through the pore 2101. The pore or channel may be microfabricated to be nanometer scale in a substrate 2102 wherein the substrate may comprise a biological membrane or a crystalline material. Alternatively, or in addition to, each component within each layer may comprise unique molecules that generate a unique impedance signature. The unique molecules may include sequence-based nucleotide/protein/hybrid tags, chemical modification of nucleotides, fluorescent probes, or any combinations thereof. In some embodiments, the signal may be an electrical current through the pore or channel in other embodiments the detectable signal is detected by impedance detectors adjacent to the pore or channel. Bursts of signal 2105 provide signatures indicative of individual identifiers.

Systems for encoding, writing, and reading data stored in nucleic acid molecules may be automated or may not be automated. Systems may be networked to allow for cloud based accesses to data or the systems may not be networked. The systems may be able to operate in zero or low-gravity environments and/or under high or low atmospheric pressure or vacuum. The system may be shielded from electromagnetic waves and other radiation to prevent degeneration of the identifiers as well as other internal electronics, chemicals, and enzyme. The system may use an external power source or may comprise a power source. The system may comprise a power generation method. One or more of the units of the system may be modular and may be a mobile device. The modules or mobiles devices may be installed or built into third party vehicles. One or more of the units or modules of the system may physically or digitally interact with external machines. For example, the system may take physical or digital input from an external machine or the system may output physical material or digital information to an external machine.

Information storage in nucleic acid molecules may have various applications including, but not limited to, long term information storage, sensitive information storage, and storage of medical information. In an example, a person's medical information (e.g., medical history and records) may be stored in nucleic acid molecules and carried on his or her person. The information may be stored external to the body (e.g., in a wearable device) or internal to the body (e.g., in a subcutaneous capsule). When a patient is brought into a medical office or hospital, a sample may be taken from the device or capsule and the information may be decoded with the use of a nucleic acid sequencer. Personal storage of medical records in nucleic acid molecules may provide an alternative to computer and cloud based storage systems. Personal storage of medical records in nucleic acid molecules may reduce the instance or prevalence of medical records being hacked. Nucleic acid molecules used for capsule-based storage of medical records may be derived from human genomic sequences. The use of human genomic sequences may decrease the immunogenicity of the nucleic acid sequences in the event of capsule failure and leakage.

Combinatorial assembly methods described herein may be used to create DNA libraries that encode for amino acid chains. Amino acid chains may be peptides or proteins. The DNA components may form junctions along functionally or structurally inert codons that may be common to all members of the combinatorial library. The DNA components may form junctions along introns such that the processed peptide or protein does not have scars between variable amino acid chains. Each combinatorial DNA molecule may be assembled in a separate reaction chamber. An in vivo expression assay may be performed to detect expression. Each combinatorial DNA molecule may be pooled together and individual in vitro expression assays may be performed by encapsulating the molecules in droplets. In vivo expression assays may be performed by transforming the molecules into cells. DNA may act as a barcode so that the cells and droplets that comprise specific amino acid chain variants are identified. Assays can have fluorescent output, so that the cells/droplets can be sorted into bins by fluorescent strength and sequenced for the purpose of correlating each combinatorial DNA sequence with a particular output. The combinatorial DNA molecules may encode for RNA. Pooled assays may be done outside of droplets or cells if the output itself is RNA abundance (e.g., RNA aptamer screening and testing). The combinatorial DNA may encode combinations of CRISPR gRNAs or micro RNAs that upregulate or downregulate genes inside of a cell. The combinatorial DNA library may be transformed into cells to test how the combinatorial gene regulation affects cellular properties during cellular perturbations. Combinatorial DNA libraries may encode for combinations of genes in a pathway. Each DNA component may contain a gene expression construct and the DNA components may form junctions along the inert DNA sequence in between genes. The DNA sequences may be transformed into cells and how different combinations of gene overexpression affects cellular properties during different cellular perturbation may be investigated.

Computer Control Systems

Figure 22:
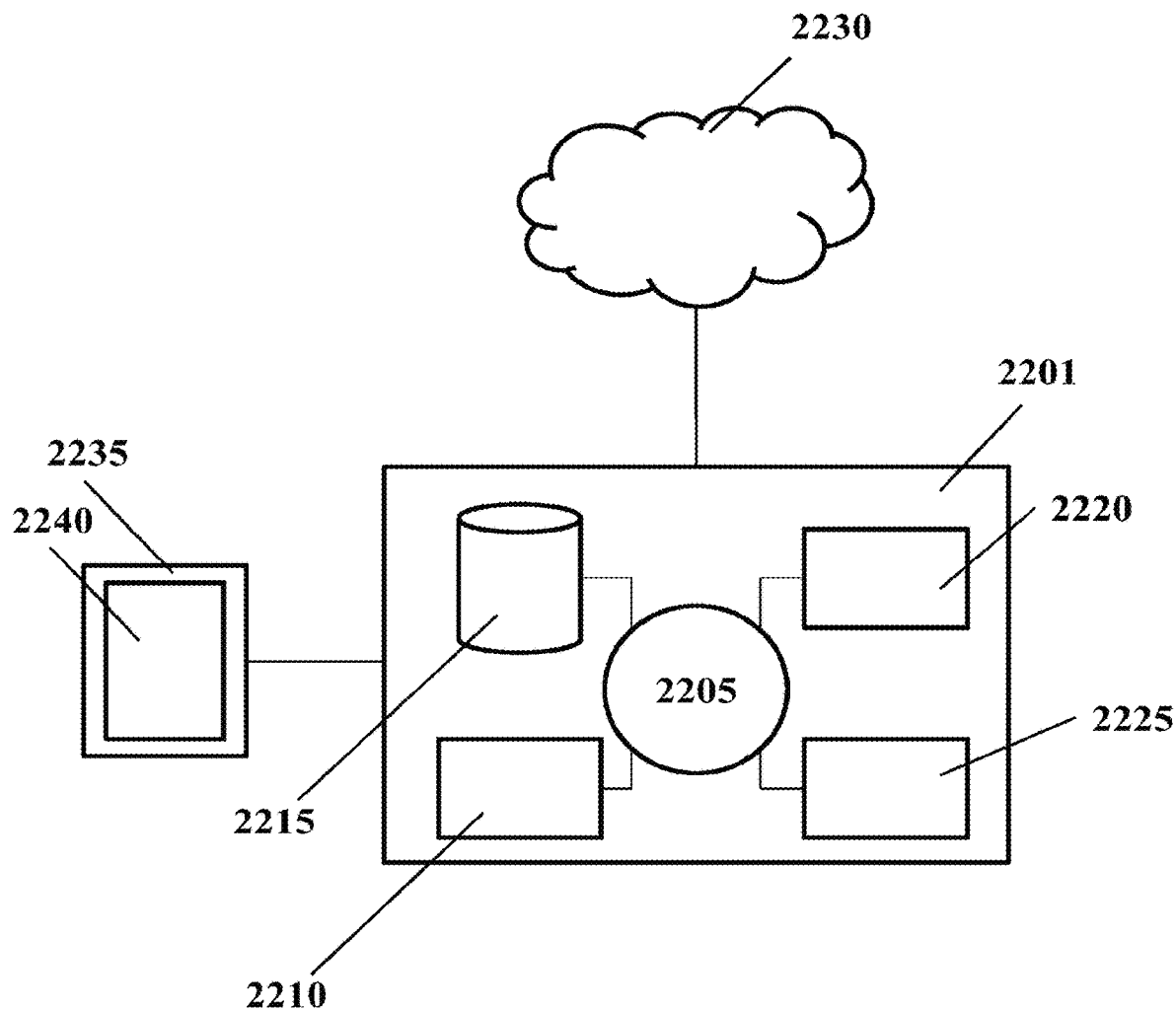
FIG. 22 shows a computer control system that is programmed or otherwise configured to implement methods provided herein.

The present disclosure provides computer systems that are programmed to implement methods of the disclosure. FIG. 22 shows a computer system 2201 that is programmed or otherwise configured to encode digital information into nucleic acid sequences and/or read (e.g., decode) information derived from nucleic acid sequences. The computer system 2201 can regulate various aspects of the encoding and decoding procedures of the present disclosure, such as, for example, the bit-values and bit location information for a given bit or byte from an encoded bitstream or byte stream.

The computer system 2201 includes a central processing unit (CPU, also "processor" and "computer processor" herein) 2205, which can be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 can be a data storage unit (or data repository) for storing data. The computer system 2201 can be operatively coupled to a computer network ("network") 2230 with the aid of the communication interface 2220. The network 2230 can be the Internet, an internet and/or extranet, or an intranet and/or extranet that is in communication with the Internet. The network 2230 in some cases is a telecommunication and/or data network. The network 2230 can include one or more computer servers, which can enable distributed computing, such as cloud computing. The network 2230, in some cases with the aid of the computer system 2201, can implement a peer-to-peer network, which may enable devices coupled to the computer system 2201 to behave as a client or a server.

The CPU 2205 can execute a sequence of machine-readable instructions, which can be embodied in a program or software. The instructions may be stored in a memory location, such as the memory 2210. The instructions can be directed to the CPU 2205, which can subsequently program or otherwise configure the CPU 2205 to implement methods of the present disclosure. Examples of operations performed by the CPU 2205 can include fetch, decode, execute, and writeback.

The CPU 2205 can be part of a circuit, such as an integrated circuit. One or more other components of the system 2201 can be included in the circuit. In some cases, the circuit is an application specific integrated circuit (ASIC).

The storage unit 2215 can store files, such as drivers, libraries and saved programs. The storage unit 2215 can store user data, e.g., user preferences and user programs. The computer system 2201 in some cases can include one or more additional data storage units that are external to the computer system 2201, such as located on a remote server that is in communication with the computer system 2201 through an intranet or the Internet.

The computer system 2201 can communicate with one or more remote computer systems through the network 2230. For instance, the computer system 2201 can communicate with a remote computer system of a user or other devices and or machinery that may be used by the user in the course of analyzing data encoded or decoded in a sequence of nucleic acids (e.g., a sequencer or other system for chemically determining the order of nitrogenous bases in a nucleic acid sequence). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2201 via the network 2230.

Methods as described herein can be implemented by way of machine (e.g., computer processor) executable code stored on an electronic storage location of the computer system 2201, such as, for example, on the memory 2210 or electronic storage unit 2215. The machine executable or machine-readable code can be provided in the form of software. During use, the code can be executed by the processor 2205. In some cases, the code can be retrieved from the storage unit 2215 and stored on the memory 2210 for ready access by the processor 2205. In some situations, the electronic storage unit 2215 can be precluded, and machine-executable instructions are stored on memory 2210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 can include or be in communication with an electronic display 2235 that comprises a user interface (UI) 2240 for providing, for example, sequence output data including chromatographs, sequences as well as bits, bytes, or bit streams encoded by or read by a machine or computer system that is encoding or decoding nucleic acids, raw data, files and compressed or decompressed zip files to be encoded or decoded into DNA stored data. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2205. The algorithm can, for example, be used with a DNA index and raw data or zip file compressed or decompressed data, to determine a customized method for coding digital information from the raw data or zip file compressed data, prior to encoding the digital information.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for coding digital information into nucleic acid sequence(s), comprising:
   an assembly unit configured to generate a nucleic acid library encoding a sequence of symbols using electrowetting, wherein said nucleic acid library comprises at least a subset of a plurality of nucleic acid molecules, the assembly unit comprising a plurality of electrode patches configured to make, combine, mix, and/or split droplets by selectively applying voltage to the electrode patches; and
   one or more computer processors operatively coupled to said assembly unit, wherein said one or more computer processors are individually or collectively programmed to (i) code said digital information into a sequence of symbols and convert said sequence of symbols into codewords using one or more codebooks, (ii) parse said codewords into a coded sequence of symbols, (iii) map said coded sequence of symbols to said plurality of nucleic acid molecules, wherein an individual nucleic acid molecule of said plurality of nucleic acid molecules comprises one or more nucleic acid sequences, and (iv) direct said assembly unit to generate an nucleic acid library, wherein each symbol of said coded sequence of symbols is encoded by one or more nucleic acid molecules.

2. The system of claim 1, wherein said one or more nucleic acid molecules are assembled in one or more assembly reactions.

3. The system of claim 2, wherein one or more products of said one or more assembly reactions are combined to generate said nucleic acid library.

4. The system of claim 1, wherein said assembly unit comprises one or more vessels.

5. The system of claim 4, wherein said one or more vessels are partitions.

6. The system of claim 1, wherein said assembly unit comprises reagents, one or more layers of components, one or more templates, or any combination thereof.

7. The system of claim 1, wherein said assembly unit is configured to receive reagents, one or more layer of components, one or more templates, or any combination thereof.

8. The system of claim 1, wherein said assembly unit is configured to output said nucleic acid library.

9. The system of claim 1, wherein said assembly unit comprises a reaction module.

10. The system of claim 9, wherein said reaction module is configured to collect reagents, one or more layers, one or more templates, or any combination thereof.

11. The system of claim 10, wherein said reagents comprise enzymes, one or more nucleic acid sequences, buffers, co-factors, or any combination thereof.

12. The system of claim 11, wherein said reagents are combined into a master mix prior to entering said reaction module.

13. The system of claim 9, wherein said reaction module is configured to incubate or agitate an assembly reaction and wherein said assembly reaction generates said one or more nucleic acid molecules.

14. The system of claim 9, wherein said reaction module comprises a detector unit and wherein said detector unit monitors assembly of said one or more nucleic acid molecules.

15. The system of claim 1, further comprising a storage unit and wherein said assembly unit transfers said generated nucleic acid library to said storage unit.

16. The system of claim 15, wherein said storage unit comprises one or more pools, vessels, or partitions.

17. The system of claim 16, wherein said storage unit combines one or more nucleic acid libraries into said one or more pools, said one or more vessels, or said one or more partitions.

18. The system of claim 1, further comprising a selection unit configured to select said one or more nucleic acid molecules.

19. The system of claim 18, wherein said selection unit comprises a size selection module, an affinity capture module, a nuclease cleavage module, or any combination thereof.

20. The system of claim 1, wherein said assembly unit generates a plurality of reactions for assembling said one or more nucleic acid molecules.

21. The system of claim 20, wherein said assembly unit selectively removes individual reactions from said plurality of reactions that do not generate said at least said subset of said plurality of nucleic acid molecules in said nucleic acid library.

22. The system of claim 1, wherein said one or more computer processors are individually or collectively programmed to use heuristic techniques to minimize a number of reactions to generate said nucleic acid library or to minimize the time it takes to set up a number of reaction to generate said nucleic acid library.

23. The system of claim 22, wherein said heuristic techniques comprise on-set covering heuristics or heuristics that minimize the traveling path of an apparatus.

24. The system of claim 1, wherein said one or more computer processors are individually or collectively programmed to direct said assembly unit to generate a plurality of droplets using electrowetting and combine two or more of the plurality of droplets to bring together selected inputs for assembling the nucleic acid molecules.

25. The system of claim 1, wherein the patches are configured so as to be separated from the droplets by an insulating coating with a low electrical conductivity.

26. The system of claim 1, wherein said one or more computer processors are individually or collectively programmed to (v) direct said assembly unit to append a description of said one or more codebooks and said plurality of nucleic acid molecules to said nucleic acid library.

27. The system of claim 1, wherein said nucleic acid library is an identifier library comprising at least a subset of a plurality of identifiers.

\* \* \* \* \*